US012570615B2

(12) United States Patent
Dolente et al.

(10) Patent No.: US 12,570,615 B2
(45) Date of Patent: Mar. 10, 2026

(54) QUINAZOLINONE DERIVATIVES

(71) Applicant: Hoffmann-La Roche Inc., Little Falls, NJ (US)

(72) Inventors: Cosimo Dolente, Allschwil (CH); David Stephen Hewings, Abingdon (GB); Daniel Hunziker, Moehlin (CH); Daniela Krummenacher, Zurich (CH); Piergiorgio Francesco Tommaso Pettazzoni, Regensdorf (CH); Fabienne Ricklin, Hombourg (FR); Claus Riemer, Freiburg (DE); Juergen Wichmann, Steinen (DE)

(73) Assignee: Hoffmann-La Roche Inc.

( * ) Notice: Subject to any disclaimer, the term of this patent is extended or adjusted under 35 U.S.C. 154(b) by 407 days.

(21) Appl. No.: 18/210,934

(22) Filed: Jun. 16, 2023

(65) Prior Publication Data

US 2023/0331682 A1 Oct. 19, 2023

Related U.S. Application Data

(63) Continuation of application No. PCT/EP2021/086049, filed on Dec. 16, 2021.

(51) Int. Cl.

*C07D 239/88* (2006.01)
*C07D 401/12* (2006.01)
*C07D 401/14* (2006.01)

(52) U.S. Cl.

CPC ......... *C07D 239/88* (2013.01); *C07D 401/12* (2013.01); *C07D 401/14* (2013.01)

(58) Field of Classification Search

CPC ... C07D 239/88; C07D 401/12; C07D 401/14
See application file for complete search history.

(56) References Cited

FOREIGN PATENT DOCUMENTS

WO WO 2009/012283 A1 1/2009
WO WO2012/118492 * 9/2012
WO WO 2012/118492 A1 9/2012
WO WO 2020/142612 A1 7/2020
WO WO 2020/261156 A1 12/2020
WO WO 2021/250521 A1 12/2021
WO WO 2022/261250 A1 12/2022
WO WO 2023/105371 A1 6/2023

OTHER PUBLICATIONS

International search report and written opinion for PCT/EP2021/086049, mailed on Mar. 14, 2022, 9 pages.

Li, Ren et al. "The discovery of potent and selective pyridopyrimidine-7-one based inhibitors of B-RafV600E kinase" Biorganic & Medicinal Chemistry Letters, Elsevier, Amsterdam, vol. 22, No. 10 10, Apr. 3, 2012, pp. 3387-3391.

Wang, Xiaolun et al. "Conformation-Specific Effects of Raf Kinase Inhibitors" J. Med. Chem. 55, Jul. 18, 2012, pp. 7332-7341.

Wenglowsky, Steve et al. "Highly potent and selective 3-N-methylquinazoline-4 (3H)-one based inhibitors of B-RafV600Ekinase", Bioorganic & Medicinal Chemistry Letters, Elsevier, Amsterdam, NL, vol. 24, No. 8, Mar. 13, 2014, pp. 1923-1927.

* cited by examiner

*Primary Examiner* — Brandon J Fetterolf

(74) *Attorney, Agent, or Firm* — Knowles Intellectual Property Strategies, LLC

(57) ABSTRACT

The invention relates to a compound of formula (I)

(I)

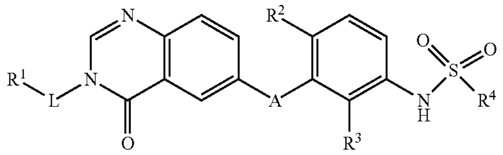

Wherein A, L, R1, R2, R3 and R4 are as defined in the description and in the claims. The compound of formula (I) can be used as a medicament.

18 Claims, No Drawings

QUINAZOLINONE DERIVATIVES

CROSS-REFERENCE TO RELATED APPLICATIONS

This application is a continuation of International Application No. PCT/EP2021/086049, filed in the European Receiving Office on Dec. 16, 2021, which claims the benefit of European Patent Application No. 20215302.9, filed Dec. 18, 2020. The entirety of each of these applications is hereby incorporated by reference herein for all purposes.

SUMMARY OF THE INVENTION

The present invention relates to organic compounds useful for therapy and/or prophylaxis in a mamal, and in particular to compounds that modulate BRAF activity.

The invention relates in particular to a novel compound of formula (I)

(I)

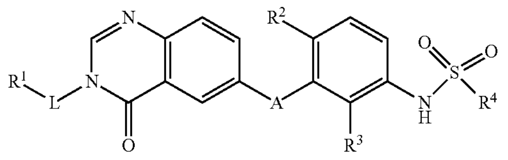

wherein

A is —O— or —NH—;

L is —$(CH_2)$n-, with n=1, 2, 3 or 4;

$R^1$ is alkoxycarbonyl, alkoxycarbonylheterocycloalkyl, alkoxycarbonylamino, phenyl, alkoxycarbonyl(alkylamino), alkylcarbonyl(alkylamino), alkoxycarbonyl (alkylamino)alkylphenyl, alkoxyalkylaminocarbonyl, alkylcarbonylheterocycloalkyl, alkoxycarbonylaminoalkoxyalkoxy, phenylalkoxy, aminoalkoxyalkoxy, hydroxycarbonyl, alkoxycarbonylheterocycloalkylcarbonyl, alkoxycarbonylheterocycloalkylaminocarbonyl or alkoxycarbonyl(alkylamino)alkylaminocarbonyl;

$R^2$ and $R^3$ are independently selected from hydrogen, halogen and cyano;

$R^4$ is dialkylamino, haloheterocycloalkyl, heterocycloalkyl, cycloalkyl or alkyl;

or a pharmaceutically acceptable salt thereof.

The Rapidly Accelerated Fibrosarcoma (RAF) class of serine-threonine kinases comprise three members (ARAF, BRAF, RAF1) that compose the first node of the MAP kinase signalling pathway. Despite the apparent redundancy of the three RAF isoforms in signalling propagation through phosphorylation of MEK1 and 2, frequent oncogenic activating mutations are commonly found only for BRAF. In particular, substitution of V600 with glutamic acid or lysine renders the kinase highly activated with consequent hyperstimulation of the MAPK pathway, independently from external stimulations (Cell. 2015 Jun. 18; 161(7): 1681-1696.)

Mutant BRAF is a targetable oncogenic driver and three BRAF inhibitors (vemurafenib, dabrafenib and encorafenib) reached the market up to now showing efficacy in BRAFV600E-positive melanoma. However rapid acquisition of drug resistance is almost universally observed and the duration of the therapeutic benefits for the targeted therapy remains limited.

Moreover, the developed BRAF inhibitors revealed an unexpected and "paradoxical" ability to repress MAPK signalling in BRAFV600E-driven tumours while the same inhibitors presented MAPK stimulatory activities in BRAF wild type (WT) models (N Engl J Med 2012; 366:271-273; and British Journal of Cancer volume 111, pages 640-645 (2014)).

Mechanistic studies on the RAF paradox then clarified that oncogenic BRAFV600E phosphorylates MEK 1/2 in its monomeric cytosolic form while WT BRAF and RAF1 activation requires a complex step of events including cell membrane translocation and homo and/or heterodimerization promoted by activated RAS (KRAS, NRAS, HRAS) (Nature Reviews Cancer volume 14, pages 455-467(2014)).

The binding of inhibitors like vemurafenib, dabrafenib or encorafenib to a WT BRAF or RAF1 protomer, quickly induces RAF homo and/or hetero dimerization and membrane association of the newly formed RAF dimer. In the dimeric conformation, one RAF protomer allosterically induces conformational changes of the second resulting in a kinase active status and, importantly, in a conformation unfavourable for the binding of the inhibitor. The dimer induced by drug treatment, as a result, promotes MEK phosphorylation by the catalysis operated by the unbound protomer with hyperactivation of the pathway.

The RAF paradox results in two clinically relevant consequences: 1) accelerated growth of secondary tumours upon BRAFi monotherapy (mainly keratochantoma and squamous-cell carcinomas) (N Engl J Med 2012; 366:271-273) and 2) the acquisition of drug resistance in the setting of BRAFi monotherapy as well as in combinations of BRAFi+MEKi presents activation of dimer-mediated RAF signalling by genetically driven events including RAS mutations, BRAF amplifications, expression of dimeric-acting BRAF splice variants (Nature Reviews Cancer volume 14, pages 455-467(2014)).

The present invention relates to the surprising finding that the BRAF inhibitor of formula (I) shows considerably less paradoxial activation of the MAPK signalling pathway while retaining high potency. This compound can also be referred to as a paradox breaker or RAF paradox breaker, compared to compounds inducing the RAF paradox (and which could be referred to as paradox inducers or RAF paradox inducers).

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C1-C8 alkyl groups are methyl, ethyl, propyl, isopropyl, butyl, isobutyl, tert-butyl, the isomeric pentyls, the isomeric hexyls, the isomeric heptyls and the isomeric octyls. Particular examples of alkyl are methyl, ethyl, propyl, butyl, isobutyl, tert-butyl and pentyl. Methyl, ethyl and propyl are more particular examples of "alkyl" in the compound of formula (I).

The term "cycloalkyl", alone or in combination, signifies a cycloalkyl ring with 3 to 8 carbon atoms and particularly a cycloalkyl ring with 3 to 6 carbon atoms. Examples of "cycloalkyl" are cyclopropyl, cyclobutyl, cyclopentyl and cyclohexyl. A particular example of "cycloalkyl" is cyclopentyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having one or two ring atoms in common. Examples of "heterocycloalkyl" are morpholinyl, pyridinyl, pyrrolidinyl, piperidinyl, piperidyl, azetidinyl and piperazinyl. Particular examples of "heterocycloalkyl" are pyrrolidinyl, piperidinyl, piperidyl and piperazinyl.

The term "alkoxy" or "alkyloxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy. Particular examples of "alkoxy" are methoxy, ethoxy and tert-butyloxy.

The term "oxy", alone or in combination, signifies the —O— group.

The term "oxo", alone or in combination, signifies the —O group.

The term "sulfonyl", alone or in combination, signifies the —SO2- group.

The term "cyano", alone or in combination, signifies the —CN group.

The terms "halogen" or "halo", alone or in combination, signifies fluorine, chlorine, bromine or iodine and particularly fluorine, chlorine or bromine, more particularly fluorine. The term "halo", in combination with another group, denotes the substitution of said group with at least one halogen, particularly substituted with one to five halogens, particularly one to four halogens, i.e. one, two, three or four halogens.

The terms "hydroxyl" and "hydroxy", alone or in combination, signify the —OH group.

The term "carbonyl", alone or in combination, signifies the —C(O)— group.

The term "amino", alone or in combination, signifies the primary amino group (—NH2), the secondary amino group (—NH—), or the tertiary amino group (—N—).

The term "alkylamino", alone or in combination, signifies an alkyl group linked to a —NH— group. The term "dialkylamino", alone or in combination, signifies two alkyl groups linked to a —N— atom.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared from addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of the compound of formula (I) are the salts of trifluoroacetic acid, hydrochloric acid, hydrobromic acid, sulfuric acid, phosphoric acid and methanesulfonic acid.

If one of the starting materials or the compound of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention thus relates to:

A compound according to formula (I) or a pharmaceutically acceptable salt thereof, wherein R1-L is alkoxycarbonyl alkyl, alkoxycarbonylheterocycloalkylalkyl, alkoxycarbonylaminoalkyl, phenylalkyl, alkoxycarbonyl(alkylamino)alkyl, alkylcarbonyl(alkylamino)alkyl, alkoxycarbonyl(alkylamino)alkylphenylalkyl, alkoxyalkylaminocarbonylalkyl, alkylcarbonylheterocycloalkylalkyl, alkoxycarbonylaminoalkoxyalkoxyalkyl, phenylalkoxyalkyl, aminoalkoxyalkoxyalkyl, hydroxycarbonylalkyl, alkoxycarbonylheterocycloalkylcarbonylalkyl, alkoxycarbonylheterocycloalkylaminocarbonylalkyl or alkoxycarbonyl(alkylamino)alkylaminocarbonylalkyl;

A compound according to formula (I) or a pharmaceutically acceptable salt thereof, wherein R1-L is alkoxycarbonylalkyl, alkoxycarbonylpiperidinylalkyl, alkoxycarbonylpiperazinylalkyl, alkoxycarbonylaminoalkyl, phenylalkyl, alkoxycarbonyl(alkylamino)alkyl, alkylcarbonyl(alkyl amino)alkyl, alkoxycarbonyl (alkylamino)alkylphenylalkyl, alkoxyalkylaminocarbonylalkyl, alkylcarbonylpiperidinylalkyl, alkoxycarbonylaminoalkoxyalkoxyalkyl, phenylalkoxyalkyl, aminoalkoxyalkoxyalkyl, hydroxycarboylalkyl, alkoxycarbonylpiperazinylcarbonylalkyl, alkoxycarbonylpiperidinylaminocarbonylalkyl, or alkoxycarbonyl (alkylamino)alkylaminocarbonylalkyl;

A compound according to formula (I) or a pharmaceutically acceptable salt thereof, wherein R1-L is tert-butyloxycarbonylpropyl, tert-butyloxycarbonylpiperidinylethyl, tert-butyloxycarbonylpiperidinylmethyl, tert-butyloxycarbonylpiperazinylethyl, tert-butyloxycarbonylaminopropyl, phenylpropyl, tert-butyloxycarbonyl(methylamino)propyl, methylcarbonyl(methylamino)propyl, tert-butyloxycarbonyl(methylamino) methylphenylpropyl, methoxyethylaminocarbonylmethyl, methylcarbonylpiperidinylmethyl, tert-butyloxycarbonyl aminoethoxy ethoxy ethyl, phenylmethyloxyethyl, aminoethoxyethoxyethyl, hydroxycarbonylpropyl, tert-butyloxycarbonylpiperazinylcarbonylpropyl, tert-butyloxycarbonylpiperidinylaminocarbonylpropyl or tert-butyloxycarbonyl (methylamino)ethylaminocarbonylpropyl;

A compound according to formula (I) or a pharmaceutically acceptable salt thereof, wherein R1-L is alkoxycarbonylheterocycloalkylalkyl, alkoxycarbonylaminoalkyl, alkoxycarbonyl(alkylamino)alkyl, alkylcarbonyl(alkylamino)alkyl, alkoxycarbonylaminoalkoxyalkoxyalkyl, alkoxycarbonylheterocycloalkylcarbonylalkyl, alkoxycarbonylheterocycloalkylaminocarbonylalkyl or alkoxycarbonyl(alkylamino)alkylaminocarbonylalkyl;

A compound according to formula (I) or a pharmaceutically acceptable salt thereof, wherein R1-L is alkoxycarbonylpiperazinylalkyl, alkoxycarbonylaminoalkyl, alkoxycarbonyl(alkylamino)alkyl, alkylcarbonyl(alkylamino)alkyl, alkoxycarbonylaminoalkoxyalkoxyalkyl, alkoxycarbonylpiperazinylcarbonylalkyl, alkoxycarbonylpiperidinylaminocarbonylalkyl or alkoxycarbonyl(alkylamino)alkylaminocarbonylalkyl;

A compound according to formula (I) or a pharmaceutically acceptable salt thereof, wherein R1-L is tert-butyloxycarbonylpiperazinylethyl, tert-butyloxycarbonylaminopropyl, tert-butyloxycarbonyl(methylamino)propyl, methylcarbonyl(methylamino)propyl, tert-butyloxycarbonylaminoethoxyethoxyethyl, tert-butyloxycarbonylpiperazinylcarbonylpropyl, tert-butyloxycarbonylpiperidinylaminocarbonylpropyl or tert-butyloxycarbonyl(methylamino)ethylaminocarbonylethyl;

A compound according to formula (I) or a pharmaceutically acceptable salt thereof, wherein R1 is alkoxycarbonyl, alkoxycarbonylheterocycloalkyl, alkoxycarbonyl amino, phenyl, alkoxycarbonyl(alkylamino), alkylcarbonyl(alkylamino), alkoxycarbonyl(alkylamino)alkylphenyl, alkoxyalkylaminocarbonyl, alkylcarbonylheterocycloalkyl, alkoxycarbonylaminoalkoxyalkoxy, phenylalkoxy, aminoalkoxyalkoxy, hydroxycarbonyl, alkoxycarbonylheterocycloalkylcarbonyl, alkoxycarbonylheterocycloalkylaminocarbonyl or alkoxycarbonyl(alkylamino)alkylaminocarbonyl;

A compound according to formula (I) or a pharmaceutically acceptable salt thereof, wherein R1 is alkoxycarbonyl, alkoxycarbonylpiperidinyl, alkoxycarbonylpiperazinyl, alkoxycarbonylamino, phenyl, alkoxycarbonyl(alkylamino), alkylcarbonyl(alkylamino), alkoxycarbonyl(alkylamino)alkylphenyl, alkoxyalkylaminocarbonyl, alkylcarbonylpiperidinyl, alkoxycarbonylaminoalkoxyalkoxy, phenylalkoxy, aminoalkoxyalkoxy, hydroxycarbonyl, alkoxycarbonylpiperazinylcarbonyl, alkoxycarbonylpiperidinylaminocarbonyl, or alkoxycarbonyl(alkylamino)alkylaminocarbonyl;

A compound according to formula (I) or a pharmaceutically acceptable salt thereof, wherein R1 is alkoxycarbonylheterocycloalkyl, alkoxycarbonylamino, alkoxycarbonyl(alkylamino), alkylcarbonyl(alkylamino), alkoxycarbonylaminoalkoxyalkoxy, alkoxycarbonylheterocycloalkylcarbonyl, alkoxycarbonylheterocycloalkylaminocarbonyl or alkoxycarbonyl(alkylamino)alkylaminocarbonyl;

A compound according to formula (I) or a pharmaceutically acceptable salt thereof, wherein R1 is tert-butyloxycarbonyl, tert-butyloxycarbonylpiperidinyl, tert-butyloxycarbonylpiperidinyl, tert-butyloxycarbonylpiperazinyl, tert-butyloxycarbonylamino, phenyl, tert-butyloxycarbonyl(methylamino), methylcarbonyl(methylamino), tert-butyloxycarbonyl(methylamino)methylphenyl, methoxyethylaminocarbonyl, methylcarbonylpiperidinyl, tert-butyloxycarbonylaminoethoxyethoxy, phenylmethyloxy, aminoethoxyethoxy, hydroxycarbonyl, tert-butyloxycarbonylpiperazinylcarbonyl, tert-butyloxycarbonylpiperidinylaminocarbonyl or tert-butyloxycarbonyl(methylamino)ethylaminocarbonyl;

A compound according to formula (I) or a pharmaceutically acceptable salt thereof, wherein R1 is tert-butyloxycarbonylpiperazinyl, tert-butyloxycarbonylamino, tert-butyloxycarbonyl(methylamino), methylcarbonyl(methylamino), tert-butyloxycarbonylaminoethoxyethoxy, tert-butyloxycarbonylpiperazinylcarbonyl, tert-butyloxycarbonylpiperidinylaminocarbonyl or tert-butyloxycarbonyl(methylamino)ethylaminocarbonyl;

A compound according to formula (I) or a pharmaceutically acceptable salt thereof, wherein R1 is phenyl;

A compound according to formula (I) or a pharmaceutically acceptable salt thereof, wherein L is $-(CH_2)n-$, with n=1, 2 or 3;

A compound according to formula (I) or a pharmaceutically acceptable salt thereof, wherein L is $-(CH_2)n-$, with n=2 or 3;

A compound according to formula (I) or a pharmaceutically acceptable salt thereof, wherein R2 and R3 are independently selected from hydrogen, fluorine and cyano;

A compound according to formula (I) or a pharmaceutically acceptable salt thereof, wherein R2 and R3 are independently selected from fluorine and cyano;

A compound according to formula (I) or a pharmaceutically acceptable salt thereof, wherein R2 and R3 are independently selected from hydrogen and cyano;

A compound according to formula (I) or a pharmaceutically acceptable salt thereof, wherein R2 and R3 are independently selected from halogen and cyano;

A compound according to formula (I) or a pharmaceutically acceptable salt thereof, wherein R2 is hydrogen or halogen, and wherein R3 is cyano;

A compound according to formula (I) or a pharmaceutically acceptable salt thereof, wherein R2 is hydrogen or fluoro, and wherein R3 is cyano;

A compound according to formula (I) or a pharmaceutically acceptable salt thereof, wherein R4 is ethyl(methylamino), (cyclopropyl)(methyl)amino, fluoropyrrolidinyl, pyrrolidinyl, cyclobutyl, cyclopentyl, cyclohexyl, azetidinyl, butyl or piperidinyl;

A compound according to formula (I) or a pharmaceutically acceptable salt thereof, wherein R4 is dialkylamino, (cycloalkyl)(alkyl)amino, halopyrrolidinyl, pyrrolidinyl, cycloalkyl, azetidinyl, alkyl, piperidinyl;

A compound according to formula (I) or a pharmaceutically acceptable salt thereof, wherein R4 is dialkylamino, haloheterocycloalkyl, heterocycloalkyl or cycloalkyl;

A compound according to formula (I) or a pharmaceutically acceptable salt thereof, wherein R4 is dialkylamino, halopyrrolidinyl, pyrrolidinyl, azetidinyl or cycloalkyl;

A compound according to formula (I) or a pharmaceutically acceptable salt thereof, wherein R4 is ethyl(methylamino), fluoropyrrolidinyl, pyrrolidinyl, azetidinyl or cyclopentyl;

A compound according to formula (I) or a pharmaceutically acceptable salt thereof, wherein R4 is fluoropyrrolidinyl;

A compound according to formula (I) or a pharmaceutically acceptable salt thereof, wherein A is —O—; and A compound according to formula (I) or a pharmaceutically acceptable salt thereof, wherein A is —NH—.

The invention further relates to a compound of formula (I) selected from tert-butyl 4-[6-[2-cyano-3-[[ethyl(methyl)sulfamoyl]amino]-6-fluoro-phenoxy]-4-oxo-quinazolin-3-yl]butanoate;

tert-butyl 4-[2-[6-[2-cyano-6-fluoro-3-[[(3R)-3-fluoropyrrolidin-1-yl]sulfonylamino]phenoxy]-4-oxo-quinazolin-3-yl]ethyl]piperidine-1-carboxylate;

tert-butyl 4-[2-[6-[2-cyano-3-[[ethyl(methyl)sulfamoyl]amino]-6-fluoro-phenoxy]-4-oxo-quinazolin-3-yl]ethyl]piperidine-1-carboxylate;

tert-butyl N-[3-[6-[2-cyano-6-fluoro-3-[[(3R)-3-fluoropyrrolidin-1-yl]sulfonylamino]phenoxy]-4-oxo-quinazolin-3-yl]propyl]carbamate;

tert-butyl N-[3-[6-[2-cyano-6-fluoro-3-(pyrrolidin-1-ylsulfonylamino)phenoxy]-4-oxo-quinazolin-3-yl]propyl]carbamate;

tert-butyl N-[3-[6-[2-cyano-3-[[ethyl(methyl)sulfamoyl]amino]-6-fluoro-phenoxy]-4-oxo-quinazolin-3-yl]propyl]carbamate;

tert-butyl 4-[2-[6-[2-cyano-6-fluoro-3-(pyrrolidin-1-ylsulfonylamino)phenoxy]-4-oxo-quinazolin-3-yl]ethyl]piperidine-1-carboxylate;

tert-butyl N-[3-[6-[2-cyano-3-(cyclopentylsulfonylamino)-6-fluoro-phenoxy]-4-oxo-quinazolin-3-yl]propyl]carbamate;

tert-butyl N-[3-[6-[3-(azetidin-1-ylsulfonylamino)-2-cyano-6-fluoro-phenoxy]-4-oxo-quinazolin-3-yl]propyl]carbamate;

tert-butyl 4-[2-[6-[2-cyano-6-fluoro-3-[[(3R)-3-fluoropyrrolidin-1-yl]sulfonylamino]phenoxy]-4-oxo-quinazolin-3-yl]ethyl]piperazine-1-carboxylate;

N-[2-cyano-4-fluoro-3-[4-oxo-3-(3-phenylpropyl)quinazolin-6-yl]oxy-phenyl]cyclopentanesulfonamide;

tert-butyl N-[3-[6-[2-cyano-3-(cyclohexylsulfonylamino)-6-fluoro-phenoxy]-4-oxo-quinazolin-3-yl]propyl]carbamate;

tert-butyl N-[3-[6-[2-cyano-6-fluoro-3-(sec-butyl sulfonylamino)phenoxy]-4-oxo-quinazolin-3-yl]propyl]carbamate;

tert-butyl 4-[2-[6-[2-cyano-3-(cyclohexylsulfonylamino)-6-fluoro-phenoxy]-4-oxo-quinazolin-3-yl]ethyl]piperidine-1-carboxylate;

tert-butyl 4-[2-[6-[2-cyano-6-fluoro-3-(sec-butyl sulfonylamino)phenoxy]-4-oxo-quinazolin-3-yl]ethyl]piperidine-1-carboxylate;

tert-butyl 4-[2-[6-[2-cyano-6-fluoro-3-(pyrrolidin-1-ylsulfonylamino)phenoxy]-4-oxo-quinazolin-3-yl]ethyl]piperazine-1-carboxylate;

tert-butyl 4-[2-[6-[2-cyano-3-(cyclopentylsulfonylamino)-6-fluoro-phenoxy]-4-oxo-quinazolin-3-yl]ethyl]piperidine-1-carboxylate;

tert-butyl 4-[2-[6-[2-cyano-6-fluoro-3-(1-piperidylsulfonylamino)phenoxy]-4-oxo-quinazolin-3-yl]ethyl]piperidine-1-carboxylate;

tert-butyl N-[3-[6-[2-cyano-6-fluoro-3-(pyrrolidin-1-ylsulfonylamino)phenoxy]-4-oxo-quinazolin-3-yl]propyl]-N-methyl-carbamate;

tert-butyl N-[3-[6-[2-cyano-3-(cyclopentylsulfonylamino)-6-fluoro-phenoxy]-4-oxo-quinazolin-3-yl]propyl]-N-methyl-carbamate;

tert-butyl 4-[2-[6-[2-cyano-3-(cyclobutylsulfonylamino)-6-fluoro-phenoxy]-4-oxo-quinazolin-3-yl]ethyl]piperidine-1-carboxylate;

tert-butyl 3-[2-[6-[2-cyano-3-(cyclopentylsulfonylamino)-6-fluoro-phenoxy]-4-oxo-quinazolin-3-yl]ethyl]piperidine-1-carboxylate;

tert-butyl 3-[2-[6-[2-cyano-6-fluoro-3-(pyrrolidin-1-ylsulfonylamino)phenoxy]-4-oxo-quinazolin-3-yl]ethyl]piperidine-1-carboxylate;

N-[3-[6-[2-cyano-3-(cyclopentylsulfonylamino)-6-fluoro-phenoxy]-4-oxo-quinazolin-3-yl]propyl]-N-methyl-acetamide;

tert-butyl 4-[2-[6-[2-cyano-3-(cyclopentylsulfonylamino)-6-fluoro-phenoxy]-4-oxo-quinazolin-3-yl]ethyl]piperazine-1-carboxylate;

N-[3-[6-[2-cyano-6-fluoro-3-(pyrrolidin-1-ylsulfonylamino)phenoxy]-4-oxo-quinazolin-3-yl]propyl]-N-methyl-acetamide;

tert-butyl 4-[2-[6-[2-cyano-3-[[ethyl(methyl)sulfamoyl]amino]-6-fluoro-phenoxy]-4-oxo-quinazolin-3-yl]ethyl]piperazine-1-carboxylate;

tert-butyl N-[[4-[3-[6-[2-cyano-3-(cyclopentylsulfonylamino)-6-fluoro-phenoxy]-4-oxo-quinazolin-3-yl]propyl]phenyl]methyl]-N-methyl-carbamate;

tert-butyl 4-[2-[6-[2-cyano-6-fluoro-3-(sec-butyl sulfonylamino)phenoxy]-4-oxo-quinazolin-3-yl]ethyl]piperazine-1-carboxylate;

tert-butyl N-[[4-[3-[6-[2-cyano-6-fluoro-3-(pyrrolidin-1-ylsulfonylamino)phenoxy]-4-oxo-quinazolin-3-yl]propyl]phenyl]methyl]-N-methyl-carbamate;

2-[6-[2-cyano-3-[[ethyl(methyl)sulfamoyl]amino]anilino]-4-oxo-quinazolin-3-yl]-N-(2-methoxyethyl)acetamide;

tert-butyl 4-[[6-[2-cyano-3-[[ethyl(methyl)sulfamoyl]amino]anilino]-4-oxo-quinazolin-3-yl]methyl]piperidine-1-carboxylate;

3-[(1-acetyl-4-piperidyl)methyl]-6-[2-cyano-3-[[ethyl(methyl)sulfamoyl]amino]anilino]-4-oxo-quinazoline;

tert-butyl N-[2-[2-[2-[6-[2-cyano-3-[[ethyl(methyl)sulfamoyl]amino]anilino]-4-oxo-quinazolin-3-yl]ethoxy]ethoxy]ethyl]carbamate;

tert-butyl 4-[6-[2-cyano-3-[[(3R)-3-fluoropyrrolidin-1-yl]sulfonylamino]anilino]-4-oxo-quinazolin-3-yl]butanoate;

(3R)—N-[3-[[3-(2-benzyloxyethyl)-4-oxo-quinazolin-6-yl]amino]-2-cyano-phenyl]-3-fluoro-pyrrolidine-1-sulfonamide;

tert-butyl 4-[2-[6-[2-cyano-3-[[(3R)-3-fluoropyrrolidin-1-yl]sulfonylamino]anilino]-4-oxo-quinazolin-3-yl]ethyl]piperidine-1-carboxylate;

3-[2-[2-(2-aminoethoxy)ethoxy]ethyl]-6-[2-cyano-3-[[ethyl(methyl)sulfamoyl]amino]anilino]-4-oxo-quinazoline;

4-[6-[2-cyano-3-[[(3R)-3-fluoropyrrolidin-1-yl]sulfonylamino]anilino]-4-oxo-quinazolin-3-yl]butanoic acid;

tert-butyl 4-[4-[6-[2-cyano-3-[[(3R)-3-fluoropyrrolidin-1-yl]sulfonylamino]anilino]-4-oxo-quinazolin-3-yl]butanoyl]piperazine-1-carboxylate;

tert-butyl 4-[4-[6-[2-cyano-3-[[(3R)-3-fluoropyrrolidin-1-yl]sulfonylamino]anilino]-4-oxo-quinazolin-3-yl]butanoylamino]piperidine-1-carboxylate;

tert-butyl 4-[6-[2-cyano-3-[[cyclopropyl(methyl)sulfamoyl]amino]anilino]-4-oxo-quinazolin-3-yl]butanoate;

tert-butyl N-[3-[6-[2-cyano-3-[[(3R)-3-fluoropyrrolidin-1-yl]sulfonylamino]anilino]-4-oxo-quinazolin-3-yl]propyl]carbamate;

(3R)—N-[2-cyano-3-[[4-oxo-3-(3-phenylpropyl)quinazolin-6-yl]amino]phenyl]-3-fluoro-pyrrolidine-1-sulfonamide;

tert-butyl N-[2-[4-[6-[2-cyano-3-[[(3R)-3-fluoropyrrolidin-1-yl]sulfonylamino]anilino]-4-oxo-quinazolin-3-yl]butanoylamino]ethyl]-N-methyl-carbamate; and tert-butyl 4-[2-[6-[2-cyano-3-(pyrrolidin-1-ylsulfonylamino)anilino]-4-oxo-quinazolin-3-yl]ethyl]piperidine-1-carboxylate;

or a pharmaceutically acceptable salt thereof.

The invention further relates to a compound of formula (I) selected from tert-butyl N-[3-[6-[2-cyano-6-fluoro-3-[[(3R)-3-fluoropyrrolidin-1-yl]sulfonylamino]phenoxy]-4-oxo-quinazolin-3-yl]propyl]carbamate;

tert-butyl N-[3-[6-[2-cyano-6-fluoro-3-(pyrrolidin-1-ylsulfonylamino)phenoxy]-4-oxo-quinazolin-3-yl]propyl]carbamate;

tert-butyl N-[3-[6-[2-cyano-3-(cyclopentylsulfonylamino)-6-fluoro-phenoxy]-4-oxo-quinazolin-3-yl]propyl]carbamate;

tert-butyl N-[3-[6-[3-(azetidin-1-ylsulfonylamino)-2-cyano-6-fluoro-phenoxy]-4-oxo-quinazolin-3-yl]propyl]carbamate;

tert-butyl 4-[2-[6-[2-cyano-6-fluoro-3-[[(3R)-3-fluoropyrrolidin-1-yl]sulfonylamino]phenoxy]-4-oxo-quinazolin-3-yl]ethyl]piperazine-1-carboxylate;

tert-butyl 4-[2-[6-[2-cyano-6-fluoro-3-(pyrrolidin-1-ylsulfonylamino)phenoxy]-4-oxo-quinazolin-3-yl]ethyl]piperazine-1-carboxylate;

tert-butyl N-[3-[6-[2-cyano-6-fluoro-3-(pyrrolidin-1-ylsulfonylamino)phenoxy]-4-oxo-quinazolin-3-yl]propyl]-N-methyl-carbamate;

tert-butyl N-[3-[6-[2-cyano-3-(cyclopentylsulfonylamino)-6-fluoro-phenoxy]-4-oxo-quinazolin-3-yl]propyl]-N-methyl-carbamate;

N-[3-[6-[2-cyano-3-(cyclopentyl sulfonylamino)-6-fluoro-phenoxy]-4-oxo-quinazolin-3-yl]propyl]-N-methyl-acetamide;

tert-butyl 4-[2-[6-[2-cyano-3-(cyclopentylsulfonylamino)-6-fluoro-phenoxy]-4-oxo-quinazolin-3-yl]ethyl]piperazine-1-carboxylate;

N-[3-[6-[2-cyano-6-fluoro-3-(pyrrolidin-1-ylsulfonylamino)phenoxy]-4-oxo-quinazolin-3-yl]propyl]-N-methyl-acetamide;

tert-butyl 4-[2-[6-[2-cyano-3-[[ethyl(methyl)sulfamoyl]amino]-6-fluoro-phenoxy]-4-oxo-quinazolin-3-yl]ethyl]piperazine-1-carboxylate;

tert-butyl N-[2-[2-[2-[6-[2-cyano-3-[[ethyl(methyl)sulfamoyl]amino]anilino]-4-oxo-quinazolin-3-yl]ethoxy]ethoxy]ethyl]carbamate;

tert-butyl 4-[4-[6-[2-cyano-3-[[(3R)-3-fluoropyrrolidin-1-yl]sulfonylamino]anilino]-4-oxo-quinazolin-3-yl]butanoyl]piperazine-1-carboxylate;

tert-butyl 4-[4-[6-[2-cyano-3-[[(3R)-3-fluoropyrrolidin-1-yl]sulfonylamino]anilino]-4-oxo-quinazolin-3-yl]butanoylamino]piperidine-1-carboxylate;

tert-butyl N-[3-[6-[2-cyano-3-[[(3R)-3-fluoropyrrolidin-1-yl]sulfonylamino]anilino]-4-oxo-quinazolin-3-yl]propyl]carbamate; and tert-butyl N-[2-[4-[6-[2-cyano-3-[[(3R)-3-fluoropyrrolidin-1-yl]sulfonylamino]anilino]-4-oxo-quinazolin-3-yl]butanoylamino]ethyl]-N-methyl-carbamate;

or a pharmaceutically acceptable salt thereof.

The invention further relates to a compound of formula (I), wherein the compound is (3R)—N-[2-cyano-3-[[4-oxo-3-(3-phenylpropyl)quinazolin-6-yl]amino]phenyl]-3-fluoro-pyrrolidine-1-sulfonamide;

or a pharmaceutically acceptable salt thereof.

The invention further relates to a compound of formula (I) selected from tert-butyl 4-[6-[2-cyano-3-[[ethyl(methyl)sulfamoyl]amino]-6-fluoro-phenoxy]-4-oxo-quinazolin-3-yl]butanoate;

tert-butyl 4-[2-[6-[2-cyano-6-fluoro-3-[[(3R)-3-fluoropyrrolidin-1-yl]sulfonylamino]phenoxy]-4-oxo-quinazolin-3-yl]ethyl]piperidine-1-carboxylate;

tert-butyl 4-[2-[6-[2-cyano-3-[[ethyl(methyl)sulfamoyl]amino]-6-fluoro-phenoxy]-4-oxo-quinazolin-3-yl]ethyl]piperidine-1-carboxylate;

tert-butyl N-[3-[6-[2-cyano-6-fluoro-3-[[(3R)-3-fluoropyrrolidin-1-yl]sulfonylamino]phenoxy]-4-oxo-quinazolin-3-yl]propyl]carbamate;

tert-butyl N-[3-[6-[2-cyano-6-fluoro-3-(pyrrolidin-1-ylsulfonylamino)phenoxy]-4-oxo-quinazolin-3-yl]propyl]carbamate;

tert-butyl N-[3-[6-[2-cyano-3-[[ethyl(methyl)sulfamoyl]amino]-6-fluoro-phenoxy]-4-oxo-quinazolin-3-yl]propyl]carbamate;

tert-butyl 4-[2-[6-[2-cyano-6-fluoro-3-(pyrrolidin-1-ylsulfonylamino)phenoxy]-4-oxo-quinazolin-3-yl]ethyl]piperidine-1-carboxylate;

tert-butyl N-[3-[6-[2-cyano-3-(cyclopentylsulfonylamino)-6-fluoro-phenoxy]-4-oxo-quinazolin-3-yl]propyl]carbamate;

tert-butyl N-[3-[6-[3-(azetidin-1-ylsulfonylamino)-2-cyano-6-fluoro-phenoxy]-4-oxo-quinazolin-3-yl]propyl]carbamate;

tert-butyl 4-[2-[6-[2-cyano-6-fluoro-3-[[(3R)-3-fluoropyrrolidin-1-yl]sulfonylamino]phenoxy]-4-oxo-quinazolin-3-yl]ethyl]piperazine-1-carboxylate;

N-[2-cyano-4-fluoro-3-[4-oxo-3-(3-phenylpropyl)quinazolin-6-yl]oxy-phenyl]cyclopentanesulfonamide;

tert-butyl N-[3-[6-[2-cyano-3-(cyclohexylsulfonylamino)-6-fluoro-phenoxy]-4-oxo-quinazolin-3-yl]propyl]carbamate;

tert-butyl N-[3-[6-[2-cyano-6-fluoro-3-(sec-butyl sulfonylamino)phenoxy]-4-oxo-quinazolin-3-yl]propyl]carbamate;

tert-butyl 4-[2-[6-[2-cyano-3-(cyclohexylsulfonylamino)-6-fluoro-phenoxy]-4-oxo-quinazolin-3-yl]ethyl]piperidine-1-carboxylate;

tert-butyl 4-[2-[6-[2-cyano-6-fluoro-3-(sec-butyl sulfonylamino)phenoxy]-4-oxo-quinazolin-3-yl]ethyl]piperidine-1-carboxylate;

tert-butyl 4-[2-[6-[2-cyano-6-fluoro-3-(pyrrolidin-1-ylsulfonylamino)phenoxy]-4-oxo-quinazolin-3-yl]ethyl]piperazine-1-carboxylate;

tert-butyl 4-[2-[6-[2-cyano-3-(cyclopentylsulfonylamino)-6-fluoro-phenoxy]-4-oxo-quinazolin-3-yl]ethyl]piperidine-1-carboxylate;

tert-butyl 4-[2-[6-[2-cyano-6-fluoro-3-(1-piperidylsulfonylamino)phenoxy]-4-oxo-quinazolin-3-yl]ethyl]piperidine-1-carboxylate;

tert-butyl N-[3-[6-[2-cyano-6-fluoro-3-(pyrrolidin-1-ylsulfonylamino)phenoxy]-4-oxo-quinazolin-3-yl]propyl]-N-methyl-carbamate;

tert-butyl N-[3-[6-[2-cyano-3-(cyclopentylsulfonylamino)-6-fluoro-phenoxy]-4-oxo-quinazolin-3-yl]propyl]-N-methyl-carbamate;

tert-butyl 4-[2-[6-[2-cyano-3-(cyclobutyl sulfonylamino)-6-fluoro-phenoxy]-4-oxo-quinazolin-3-yl]ethyl]piperidine-1-carboxylate;

tert-butyl 3-[2-[6-[2-cyano-3-(cyclopentylsulfonylamino)-6-fluoro-phenoxy]-4-oxo-quinazolin-3-yl]ethyl]piperidine-1-carboxylate;

tert-butyl 3-[2-[6-[2-cyano-6-fluoro-3-(pyrrolidin-1-ylsulfonylamino)phenoxy]-4-oxo-quinazolin-3-yl]ethyl]piperidine-1-carboxylate;

N-[3-[6-[2-cyano-3-(cyclopentyl sulfonylamino)-6-fluoro-phenoxy]-4-oxo-quinazolin-3-yl]propyl]-N-methyl-acetamide;

tert-butyl 4-[2-[6-[2-cyano-3-(cyclopentylsulfonylamino)-6-fluoro-phenoxy]-4-oxo-quinazolin-3-yl]ethyl]piperazine-1-carboxylate;

N-[3-[6-[2-cyano-6-fluoro-3-(pyrrolidin-1-ylsulfonylamino)phenoxy]-4-oxo-quinazolin-3-yl]propyl]-N-methyl-acetamide;

tert-butyl 4-[2-[6-[2-cyano-3-[[ethyl(methyl)sulfamoyl]amino]-6-fluoro-phenoxy]-4-oxo-quinazolin-3-yl]ethyl]piperazine-1-carboxylate;

tert-butyl N-[[4-[3-[6-[2-cyano-3-(cyclopentylsulfonylamino)-6-fluoro-phenoxy]-4-oxo-quinazolin-3-yl]propyl]phenyl]methyl]-N-methyl-carbamate;

tert-butyl 4-[2-[6-[2-cyano-6-fluoro-3-(sec-butyl sulfonylamino)phenoxy]-4-oxo-quinazolin-3-yl]ethyl]piperazine-1-carboxylate;

tert-butyl N-[[4-[3-[6-[2-cyano-6-fluoro-3-(pyrrolidin-1-ylsulfonylamino)phenoxy]-4-oxo-quinazolin-3-yl]propyl]phenyl]methyl]-N-methyl-carbamate;

tert-butyl 4-[[6-[2-cyano-3-[[ethyl(methyl)sulfamoyl]amino]anilino]-4-oxo-quinazolin-3-yl]methyl]piperidine-1-carboxylate;

3-[(1-acetyl-4-piperidyl)methyl]-6-[2-cyano-3-[[ethyl(methyl)sulfamoyl]amino]anilino]-4-oxo-quinazoline;

tert-butyl N-[2-[2-[2-[6-[2-cyano-3-[[ethyl(methyl)sulfamoyl]amino]anilino]-4-oxo-quinazolin-3-yl]ethoxy]ethoxy]ethyl]carbamate;

tert-butyl 4-[6-[2-cyano-3-[[(3R)-3-fluoropyrrolidin-1-yl]sulfonylamino]anilino]-4-oxo-quinazolin-3-yl]butanoate;

(3R)—N-[3-[[3-(2-benzyloxyethyl)-4-oxo-quinazolin-6-yl]amino]-2-cyano-phenyl]-3-fluoro-pyrrolidine-1-sulfonamide;

tert-butyl 4-[2-[6-[2-cyano-3-[[(3R)-3-fluoropyrrolidin-1-yl]sulfonylamino]anilino]-4-oxo-quinazolin-3-yl]ethyl]piperidine-1-carboxylate;

tert-butyl 4-[4-[6-[2-cyano-3-[[(3R)-3-fluoropyrrolidin-1-yl]sulfonylamino]anilino]-4-oxo-quinazolin-3-yl]butanoyl]piperazine-1-carboxylate;

tert-butyl 4-[6-[2-cyano-3-[[cyclopropyl(methyl)sulfamoyl]amino]anilino]-4-oxo-quinazolin-3-yl]butanoate;

tert-butyl N-[3-[6-[2-cyano-3-[[(3R)-3-fluoropyrrolidin-1-yl]sulfonylamino]anilino]-4-oxo-quinazolin-3-yl]propyl]carbamate;

(3R)—N-[2-cyano-3-[[4-oxo-3-(3-phenylpropyl)quinazolin-6-yl]amino]phenyl]-3-fluoro-pyrrolidine-1-sulfonamide;

tert-butyl N-[2-[4-[6-[2-cyano-3-[[(3R)-3-fluoropyrrolidin-1-yl]sulfonylamino]anilino]-4-oxo-quinazolin-3-yl]butanoylamino]ethyl]-N-methyl-carbamate; and tert-butyl 4-[2-[6-[2-cyano-3-(pyrrolidin-1-ylsulfonylamino)anilino]-4-oxo-quinazolin-3-yl]ethyl]piperidine-1-carboxylate;

or a pharmaceutically acceptable salt thereof.

The preparation of the compound of formula (I) of the present invention may be carried out in sequential or convergent synthetic routes. Syntheses of the invention are shown in the following general schemes. The skills required for carrying out the reactions and purifications of the resulting products are known to those persons familiar with the art. In case a mixture of enantiomers or diastereoisomers is produced during a reaction, these enantiomers or diastereoisomers can be separated by methods described herein or known to those skilled in the art such as e.g. (chiral) chromatography or crystallization. The substituents and indices used in the following description of the processes have the significance given herein.

The compound of formula (I) wherein A is —O— can be prepared by the reaction of aryl fluorides A with sulfonamides or sulfamides B in the presence of a base such as Cs2CO3 or NaH in a solvent such as DMF or NMP (Scheme 1).

Scheme 1

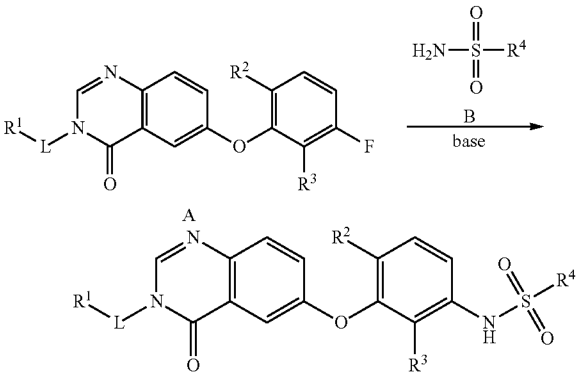

(I)

In scheme 1, L, R1, R2, R3 and R4 are as defined above.

The compound of formula (I) wherein A is —NH— can be prepared by the reaction of bromides of formula C with anilines D in the presence of a base such as Cs2CO3, a palladium catalyst such as tris(dibenzylideneacetone)dipalladium (0) and a ligand such as BippyPhos in a solvent such as dioxane (Scheme 2).

Scheme 2

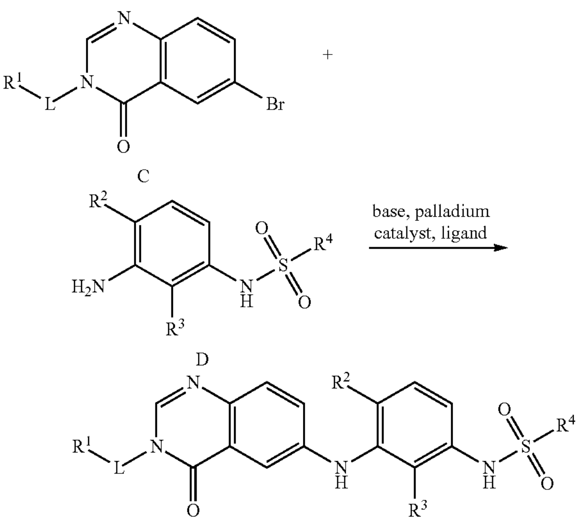

(I)

In scheme 2, L, R1, R2, R3 and R4 are as defined above.

The compound of formula (I) wherein A is —NH— can also be prepared by the reaction of amines of formula E with sulfonyl or sulfamoyl chlorides F in the presence of a base such as pyridine, in a solvent such as DCM (Scheme 3).

Scheme 3

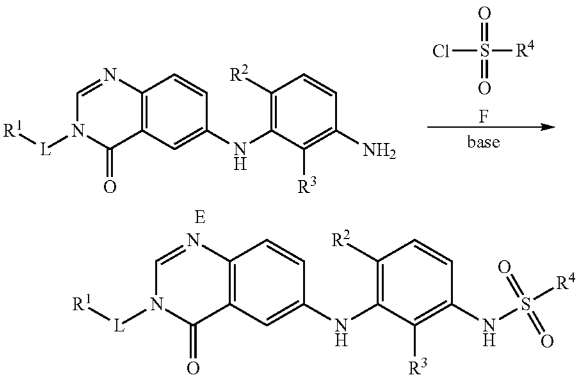

(I)

In scheme 3, L, R1, R2, R3 and R4 are as defined above.

In some cases the compound of formula (I) can be prepared by further modification of the compounds prepared as described in Schemes 1-3. In particular, in compound G where R1 contains a protecting group (PG) bound to a carboxylic ester, which is further linked to the quinazolinone by an alkyl linker L, hydrolysis gives the corresponding acid H, which may be coupled with an amine to provide a compound of formula (Ia) containing an amide (Scheme 4). Reagents and conditions for hydrolysis of carboxylic esters are well described, for example in "Protective Groups in Organic Chemistry" by T. W. Greene and P. G. M. Wutts, 5th Ed., 2014, John Wiley & Sons, N.Y. Reagents and conditions for amide coupling are well described, for example in A. El-Faham and F. Albericio, Chem. Rev. 2011, 111 (11), 6557-6602.

Scheme 4

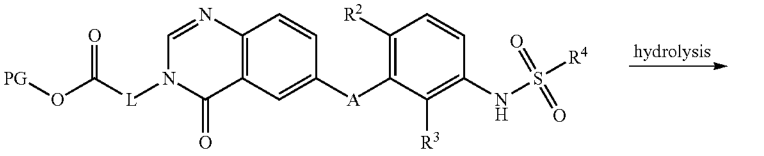

G

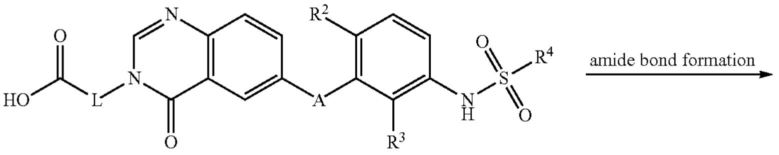

H

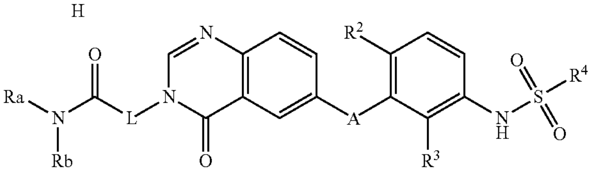

(Ia)

In scheme 4, L, A, R2, R3 and R4 are as defined above; Ra is alkoxyalkyl, alkoxycarbonylheterocycloalkyl or alkoxycarbonyl(alkylamino)alkyl; Rb is hydrogen.

Alternatively in compound I where R1 contains a protected amine linked to the quinazolinone by a linker L, deprotection gives the free amine or salt thereof J, which can be transformed into an amide compound of formula (Ib) by standard procedures (for example by reaction with an acid anhydride, or with a carboxylic acid and an activating agent) (Scheme 5).

Scheme 5

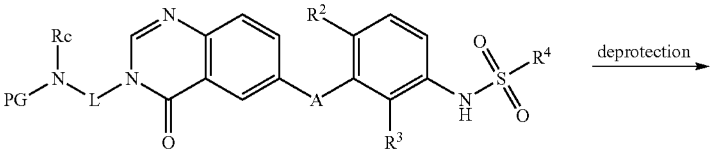

I

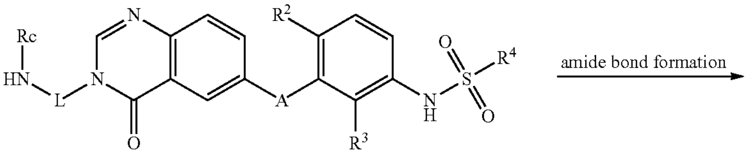

J

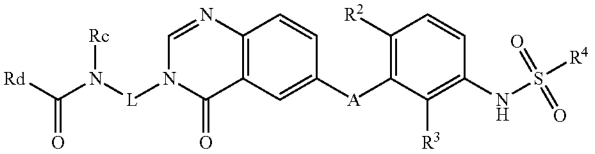

(Ib)

In scheme 5, L, A, R2, R3 and R4 are as defined above; Rc is hydrogen or alkyl; and Rd is alkoxy or alkyl.

General Synthesis of Intermediates

Intermediates A can be prepared by the reaction of 6-hydroxy-quinazolin-4-ones K with fluorobenzonitriles L in the presence of a base such as NaH or Cs2CO3 in a solvent such as DMF or NMP (Scheme 6).

Scheme 6

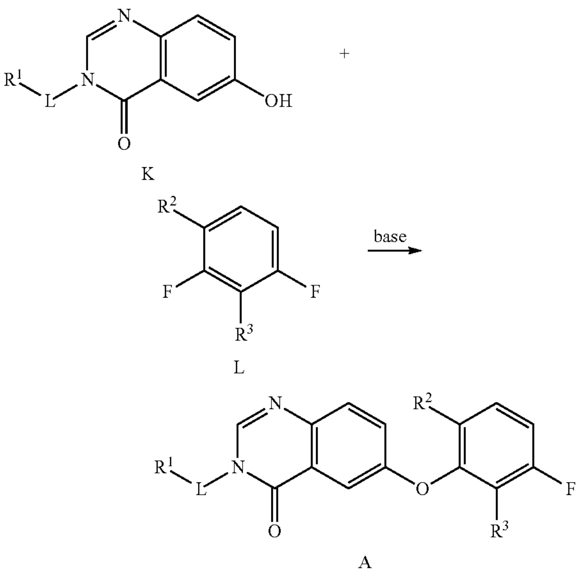

In scheme 6, L, R1, R2 and R3 are as defined above.

6-Hydroxy-quinazolin-4-one intermediates K (if not commercially available) can be prepared by a variety of routes. In some examples (Scheme 7), 6-hydroxyquinazolin-4-ones K can be prepared from 2-amino-5-hydroxy-benzoic acid and formamide, for example by heating in the absence of solvent. This intermediate M may be further derivatized by protection of the hydroxyl group as an acetate ester N under standard conditions, such as the use of acetic anhydride, DMAP and triethylamine in DCM. Subsequent alkylation on nitrogen using a suitable alkyl halide with a base such as Cs2CO3 in a solvent such as DMF to give O, followed by deprotection by aqueous base, gives the desired intermediates K.

Scheme 7

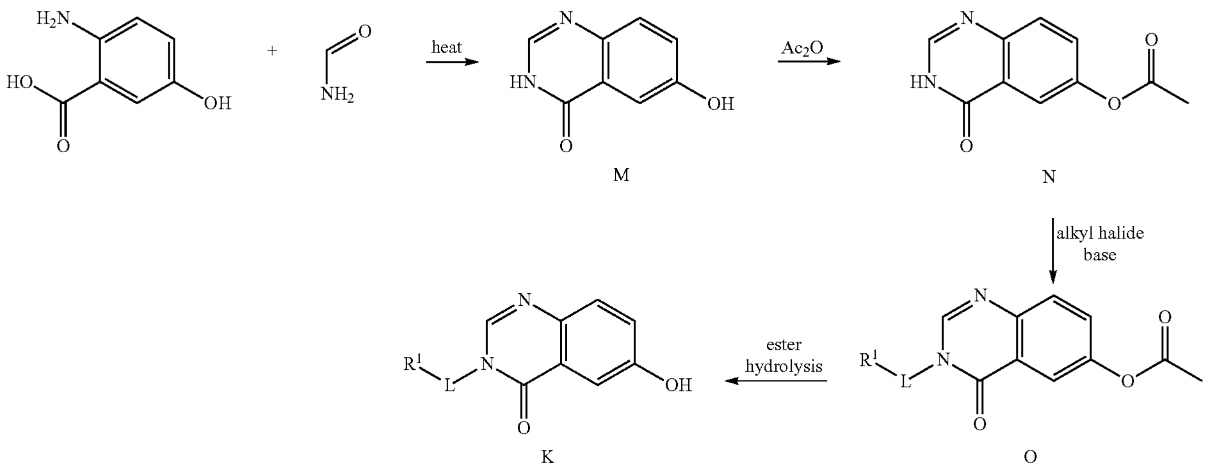

In scheme 7, L and R1 are as defined above.

Intermediates C can be prepared by alkylation of commercially-available 6-bromo-3H-quinazolin-4-one in the presence of a base such as Cs2CO3 in a solvent such as DMF. Bromides C can subsequently be converted to alcohols K by treatment with a palladium catalyst such as tris(dibenzylideneacetone)dipalladium (0), a ligand such as tBuXPhos, aqueous base such as aqueous KOH and a solvent such as dioxane (Scheme 8).

Scheme 8

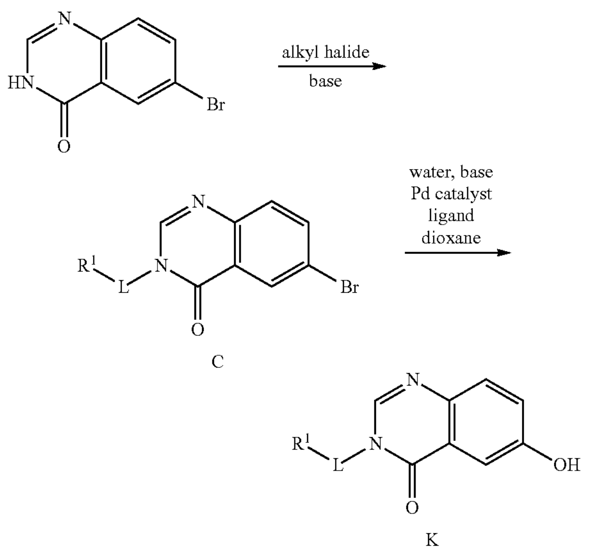

In scheme 8, L and R1 are as defined above.

In the case that the desired alkyl halide as shown in Scheme 8 is not commercially available, it can be prepared by a variety of methods known to those skilled in the art. In one example (Scheme 9), commercially-available tert-butyl 3-(4-cyanophenyl)propanoate is reduced to the corresponding amine with hydrogen and a palladium catalyst, followed by protection with a protecting group such as Boc under standard conditions, such as di-tert-butyl dicarbonate in a solvent such as DCM. The nitrogen can be alkylated by treatment with an alkyl halide such as methyl iodide in the presence of a base such as NaH in a solvent such as DMF. Reduction of the ester to the alcohol using a reducing agent such as LiBH4 in a solvent such as THF, followed by bromination of the alcohol using, for example, triphenyl phosphine and carbon tetrabromide in a solvent such as DCM, gives the intermediate P.

-continued

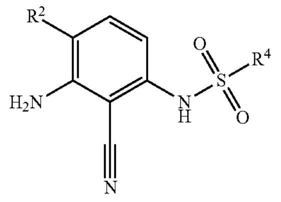

D

In scheme 10, R2 and R4 are as defined above.

Scheme 9

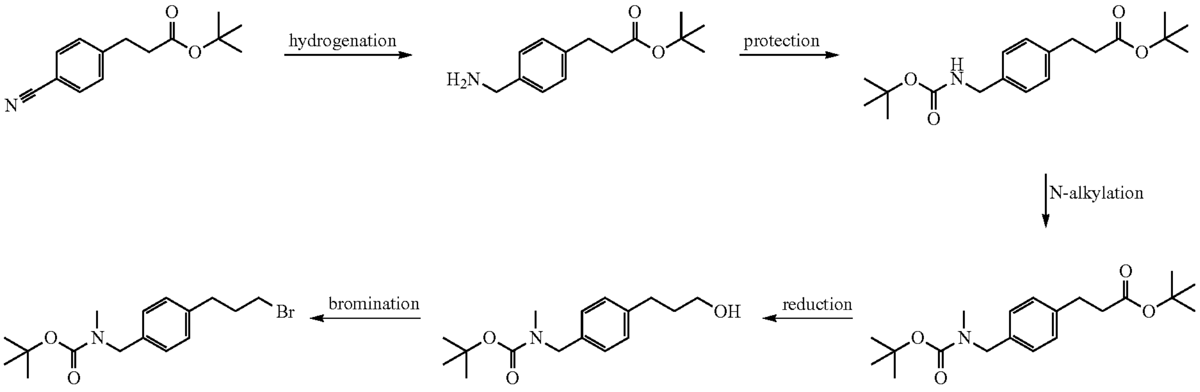

Intermediates D can be prepared by reaction of 2,6-dinitrobenzonitrile Q with sulfamides B in the presence of a base such as Cs2CO3 in a solvent such as DMF, to afford R, which can subsequently be reduced to D by catalytic hydrogenation, using a catalyst such as Pearlman's catalyst (Scheme 10).

Intermediates E where A is —NH— can also be prepared by the reaction of bromides C with 2,6-diaminobenzonitrile S in the a presence of a base such as Cs2CO3, a palladium catalyst such as tris(dibenzylideneacetone)dipalladium (0) and a ligand such as BippyPhos in a solvent such as dioxane (Scheme 11).

Scheme 10

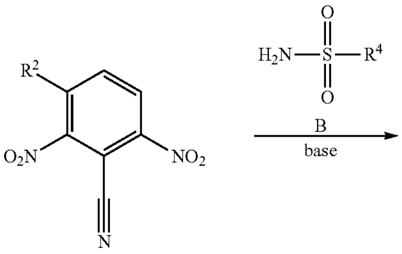

Q

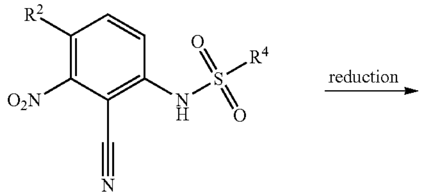

R

Scheme 11

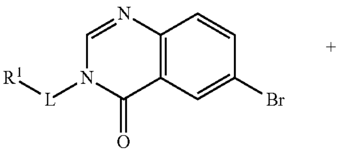

C

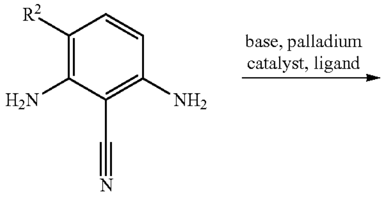

S

-continued

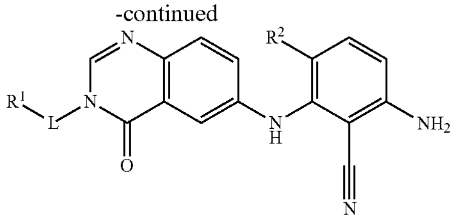

E

In scheme 11, L, R1 and R2 are as defined above.

Intermediates B, where R4 is of the type NReRf (i.e. sulfamides), where not commercially available, can be prepared from the reaction of sulfuric diamide with an amine T in dioxane, in the presence of absence of a base such as triethylamine (Scheme 12).

Scheme 12

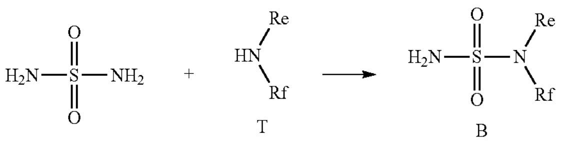

T B

In scheme 12, Re is alky or cycloalkyl, and Rf is alkyl; or Re and Rf together with the N atom to which they are attached to form an heterocycloalkyl, wherein the heterocycloalkyl is optionally substituted with halogen.

Intermediates B, where R4 is of the type CHRgRh (i.e. sulfonamides), where not commercially available, can be prepared from the corresponding sulfonyl chlorides U by reaction with aqueous ammonia (Scheme 13).

Scheme 13

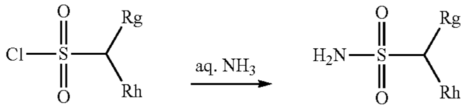

U B

In scheme 13, Rg is alky or cycloalkyl, and Rh is alkyl; or Rg and Rh together with the carbon atom to which they are attached form a cycloalkyl.

The invention thus also relates to a process for the preparation of a compound of formula (I) or a pharmaceutically acceptable salt thereof, comprising one of the following steps:

(a) the reaction of a compound of formula (A1)

(A1)

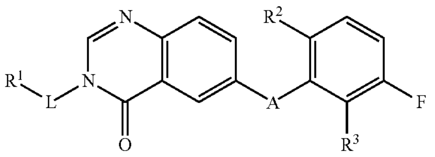

with a compound of formula (A2)

(A2)

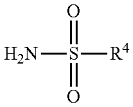

in the presence of a base;

(b) the reaction of a compound of formula (B1)

(B1)

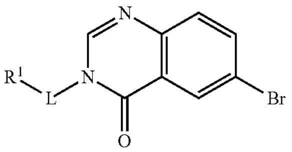

with a compound of formula (B2)

(B2)

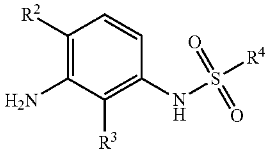

in the presence of a base, a palladium catalyst and a suitable ligand; or (c) the reaction of a compound of formula (C1)

(C1)

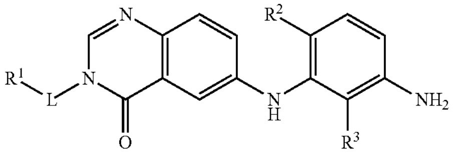

with a compound of formula (C2)

(C2)

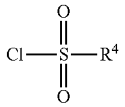

in the presence of a base;

wherein L, R1, R2, R3 and R4 are as defined above.

The reaction of step (a) can conveniently be carried out in a solvent. The solvent can be for example DMF, NMP, or a mixture thereof.

In the reaction of step (a) the base can be for example triethylamine, DIPEA, Cs2CO3 or NaH. Conveniently the base is Cs2CO3 or NaH.

Convenient conditions for the reaction of step (a) can be between around 0° C.-100° C., particularly between around 20° C. and around 80° C., more particularly between around 40° C. and around 60° C.

Preferred conditions for the reaction of step (a) are the use of DMF and Cs2CO3 or of NMP and NaH at around 50° C. for between around 10 minutes and around 5 hrs, in particular between around 15 minutes and around 1 h.

The reaction of step (b) can conveniently be carried out in a solvent. The solvent can be for example dioxane.

In the reaction of step (b) the base can be for example Cs2CO3.

Convenient conditions for the reaction of step (b) can be between around 60° C. and around 160° C., particularly between around 80° C.-140° C., more particularly between around 100° C. and around 120° C.

Preferred conditions for the reaction of step (b) are the use of dioxane NMP and Cs2CO3 at around 110° C. for between around 30 minutes and around 10 hrs, in particular between around 1 h and around 4 hrs.

The reaction of step (c) can conveniently be carried out in a solvent. The solvent can be for example DCM.

In the reaction of step (c) the base can be for example triethylamine, DIPEA, or pyridine. Conveniently the base is pyridine.

Convenient conditions for the reaction of step (c) can be between around 10° C.-130° C., particularly between around 30° C. and around 110° C., more particularly between around 50° C. and around 90° C.

Preferred conditions for the reaction of step (c) are the use of DCM and pyridine at around 70° C. for between around 1 h and around 30 hrs, in particular between around 12 hrs and around 22 hrs.

The invention also relates to a compound according to the invention when manufactured according to a process of the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such a composition may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention also relates in particular to:

A compound of formula (I) or a pharmaceutically acceptable salt thereof, for use as therapeutically active substance;

A pharmaceutical composition comprising a compound of formula (I) or a pharmaceutically acceptable salt thereof, and a therapeutically inert carrier;

The use of a compound of formula (I) or a pharmaceutically acceptable salt thereof, for the treatment or prophylaxis of cancer, in particular melanoma or non-small cell lung cancer (NSCLC);

The use of a compound of formula (I) or a pharmaceutically acceptable salt thereof, for the preparation of a medicament for the treatment or prophylaxis of cancer, in particular melanoma or non-small cell lung cancer (NSCLC);

A compound of formula (I) or a pharmaceutically acceptable salt thereof, for use in the treatment or prophylaxis of cancer, in particular melanoma or non-small cell lung cancer (NSCLC); and A method for the treatment cancer, in particular melanoma or non-small cell lung cancer (NSCLC), which method comprises administering an effective amount of a compound of formula (I) or a pharmaceutically acceptable salt thereof, to a patient in need thereof.

A certain embodiment of the invention relates to the compound of formula (I) as described herein, or a pharmaceutically acceptable salt thereof, for the use in the treatment or prophylaxis of cancer, in particular melanoma or NSCLC, characterized by a BRAF mutation selected from V600E and V600K.

A certain embodiment of the invention relates to a method for the treatment or prophylaxis of cancer, in particular melanoma or NSCLC, wherein a BRAF mutation selected from V600E and V600K is present in the cancer, which method comprises administering an effective amount of a compound of formula (I) as described herein, or a pharmaceutically acceptable salt thereof, to a patient in need thereof.

Furthermore, the invention includes all substituents in its corresponding deuterated form, wherever applicable, of the compound of formula (I).

Furthermore, the invention includes the corresponding carboxylic acid of the ester form, wherever applicable, of the compound of formula (I).

Furthermore, the invention includes all optical isomers, i.e. diastereoisomers, diastereomeric mixtures, racemic mixtures, all their corresponding enantiomers and/or tautomers as well as their solvates, wherever applicable, of the compound of formula (I).

The invention will now be illustrated by the following examples which have no limiting character.

EXAMPLES

Abbreviations

BOC=tert-butyloxycarbonyl; CAS=chemical abstract service; DCM=dichloromethane; DIPEA=diisopropylethylamine; DMF=dimethylformamide; DMAP=dimethylaminopyridine; DMSO=dimethyl sulfoxide; ESI=electrospray ionization; EtOAc=ethyl acetate; HATU=hexafluorophosphate azabenzotriazole tetramethyl uronium; HPLC=high performance liquid chromatography; MeOH=methanol; MS=mass spectrometry; NMP=N-Methyl-2-pyrrolidone; NMR=nuclear magnetic resonance; rt=room temperature; SFC=supercritical fluid chromatography; THF= tetrahydrofuran.

Intermediates A (IAs)

IA1: tert-butyl 4-(6-hydroxy-4-oxo-quinazolin-3-yl)butanoate

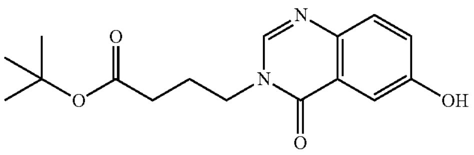 [SMILES: CC(C)(C)OC(=O)CCCn1cnc2ccc(O)cc2c1=O]

Step 1: 6-hydroxy-3H-quinazolin-4-one

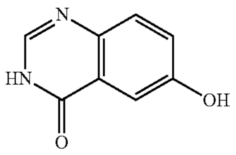 [SMILES: O=c1[nH]cnc2ccc(O)cc12]

2-Amino-5-hydroxybenzoic acid (5.0 g, 32.7 mmol, Eq: 1.0) and formamide (11.3 g, 10 mL, 251 mmol, Eq: 7.7) were heated in a sealed tube at 165° C. for 1 h, then cooled to rt. The reaction was diluted with 35 mL water and stirred at rt for about 30 min. The resulting precipitate was collected by filtration, the grey solid was washed 3× with 10 mL water and 2× with 6 mL diethyl ether. The solid was taken up in toluene and evaporated (3×), then dried in vacuo at 40° C. overnight under high vacuum to give the title compound as a grey solid (4.92 g, 93% yield). MS (ESI): 163.1 [M+H]+.

Step 2: (4-oxo-3H-quinazolin-6-yl)acetate

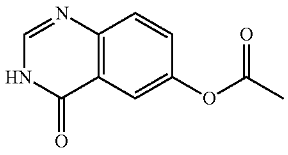

To a suspension of 6-hydroxyquinazolin-4(3H)-one (1.0 g, 6.17 mmol, Eq: 1.0) and triethylamine (125 mg, 172 µL, 1.23 mmol, Eq: 0.2) in DCM (40 mL) were added acetic anhydride (1.84 g, 1.7 mL, 18 mmol, Eq: 2.92) and DMAP (23.1 mg, 185 µmol, Eq: 0.03) at 0° C. The reaction mixture was allowed to warm to rt and stirred for 20 h 45 min, then concentrated in vacuo. The residue was diluted with DCM, evaporated with silica gel to dryness and transferred to a column. Purification by flash chromatography (40 g silica, 0-60% EtOAc in heptane, then with 0-11% MeOH in DCM) gave the title compound as a white solid (711 mg, 57% yield). MS (ESI): 205.1 [M+H]+.

Step 3: tert-butyl 4-(6-acetoxy-4-oxo-quinazolin-3-yl)butanoate

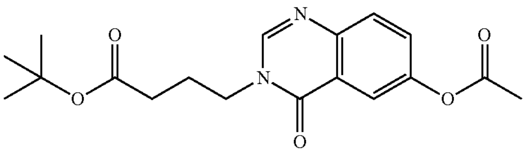 [SMILES: CC(=O)Oc1ccc2ncn(CCCC(=O)OC(C)(C)C)c(=O)c2c1]

In a three-necked flask, (4-oxo-3H-quinazolin-6-yl)acetate (200 mg, 980 µmol, Eq: 1.0) and Cs2CO3 (479 mg, 1.47 mmol, Eq: 1.5) were combined with DMF (5 mL) to give a brown suspension. Then tert-butyl 4-bromobutanoate (334 mg, 1.47 mmol, Eq: 1.5) was added at rt. The reaction was stirred at rt for 14.5 h, then concentrated in vacuo. The residue was diluted with DCM and evaporated with silica gel to dryness and transferred to a column. Purification by flash chromatography (40 g silica, 0-90% EtOAc in heptane) gave the title compound as a colourless viscous oil (250 mg, 74% yield). MS (ESI): 347.2 [M+H]+.

Step 4: tert-butyl 4-(6-hydroxy-4-oxo-quinazolin-3-yl)butanoate

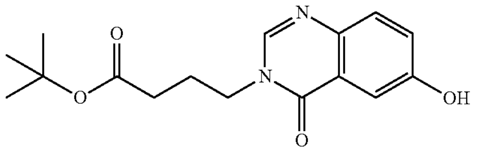 [SMILES: CC(C)(C)OC(=O)CCCn1cnc2ccc(O)cc2c1=O]

LiOH (1 M aq. solution, 617 µL, 617 µmol, Eq: 1.8) was added dropwise to a solution of tert-butyl 4-(6-acetoxy-4-oxoquinazolin-3(4H)-yl)butanoate (118.8 mg, 343 µmol, Eq: 1.0) in THF (2 mL) at room temperature under an argon atmosphere. The mixture was stirred at room temperature for 1.5 h, then further LiOH (1 M aq. solution, 137 μL, 137 μmol, Eq: 0.4) was added. The mixture was stirred at room temperature for 1 h 50 min, then further LiOH (1 M aq. solution, 137 μL, 137 μmol Eq: 0.4) was added. The mixture was stirred at room temperature for 1 h, then diluted with mL water and 15 mL EtOAc. HCl (0.5 M aq. solution, 1.78 mL, 892 μmol, Eq: 2.6) was added, the aq. layer was extracted once again with 15 mL EtOAc, the combined organic layers were washed 1× with brine, dried over Na2SO4, filtered and the solvent was evaporated. The residue was dried at high vacuum to give the title compound as a white solid (104 mg, 97% yield). MS (ESI): 305.2 [M+H]+.

IA2: tert-butyl 4-[2-(6-hydroxy-4-oxo-quinazolin-3-yl)ethyl]piperidine-1-carboxylate

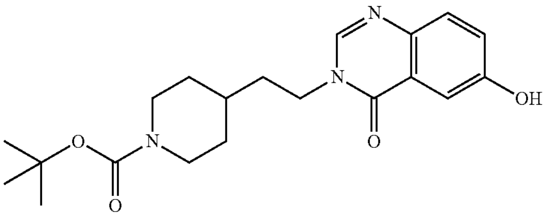 [SMILES: CC(C)(C)OC(=O)N1CCC(CCn2cnc3ccc(O)cc3c2=O)CC1]

Step 1: tert-butyl 4-[2-(6-bromo-4-oxo-quinazolin-3-yl)ethyl]piperidine-1-carboxylate

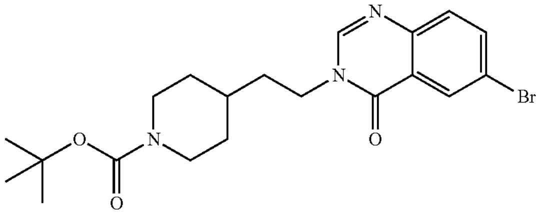 [SMILES: CC(C)(C)OC(=O)N1CCC(CCn2cnc3ccc(Br)cc3c2=O)CC1]

6-Bromoquinazolin-4(3H)-one (1.0 g, 4.44 mmol, Eq: 1.0) and Cs2CO3 (1.74 g, 5.33 mmol, Eq: 1.2) were combined with DMF (20 mL), then tert-butyl 4-(2-bromoethyl) piperidine-1-carboxylate (1.61 g, 5.33 mmol, Eq: 1.2) was added at rt. The reaction was stirred at rt for 15 h 40 min, then concentrated in vacuo. The residue was diluted with DCM, evaporated with silica gel to dryness and transferred to a column. Purification by flash chromatography (80 g silica, 0-100% EtOAc in heptane) gave the title compound as a colourless viscous oil (1.83 g, 94% yield). MS (ESI) m/z: 336.1 [M+H-Boc]+.

Step 2: tert-butyl 4-[2-(6-hydroxy-4-oxo-quinazolin-3-yl)ethyl]piperidine-1-carboxylate

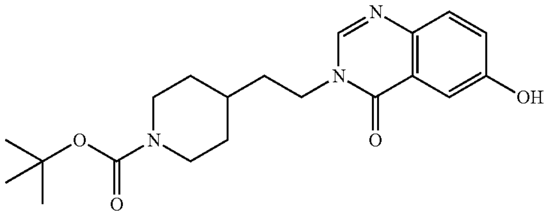 [SMILES: CC(C)(C)OC(=O)N1CCC(CCn2cnc3ccc(O)cc3c2=O)CC1]

Under argon in a microwave vial, KOH (637 mg, 9.76 mmol, Eq: 4.0) was dissolved in water (15 mL) then dioxane (20 mL) was added. The mixture was flushed with argon, then tBuXPhos (64.1 mg, 146 μmol, Eq: 0.06), tris(dibenzylideneacetone)dipalladium (0) chloroform adduct (75.8 mg, 73.2 μmol, Eq: 0.03) and tert-butyl 4-[2-(6-bromo-4-oxo-quinazolin-3-yl)ethyl]piperidine-1-carboxylate (1065 mg, 2.44 mmol, Eq: 1.0) were added. The reaction was sparged with argon, and the vial was closed. The reaction mixture was heated to 105° C. for 1 h 30 min, then cooled to rt. The reaction mixture was diluted with 25 mL water and extracted 3× with diethyl ether. The combined organic layers were washed with 25 mL water. The combined aq. layers were acidified with HCl (0.5 M aq. solution, 19.5 mL, 9.76 mmol, Eq: 4.0) and extracted 2× with EtOAc. The combined EtOAc layers were washed 1× with brine, dried over Na2SO4, filtered and the solvent was evaporated. The residue was dried at high vacuum to give the title compound as a light brown solid (880 mg, 97% yield). MS (ESI) m/z: 372.3 [M−H]−.

The following intermediates A (IAs) were prepared by analogy to intermediate IA3 using the appropriate bromide reagent in Step 1:

| IA | Systematic name | Structure | Bromide reagent | MS (ESI) |
|---|---|---|---|---|
| IA3 | tert-butyl N-[3-(6-hydroxy-4-oxo-quinazolin-3-yl)propyl] carbamate | 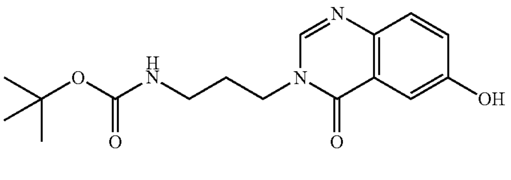 | tert-butyl N-(3-bromopropyl) carbamate (CAS 83948-53-2) | 318.3 [M − H]− |
| IA4 | tert-butyl 4-[2-(6-hydroxy-4-oxo-quinazolin-3-yl)ethyl]piperazine-1-carboxylate | 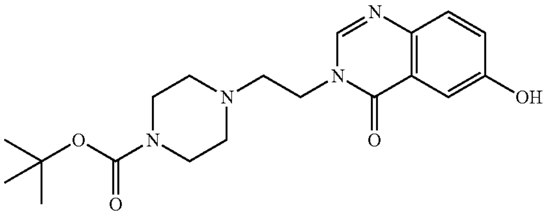 | tert-butyl 4-(2-bromoethyl) piperazine-1-carboxylate (CAS 655225-01-7) | 373.3 [M − H]− |

-continued

| IA | Systematic name | Structure | Bromide reagent | MS (ESI) |
|---|---|---|---|---|
| IA5 | 6-hydroxy-3-(3-phenylpropyl) quinazolin-4-one | 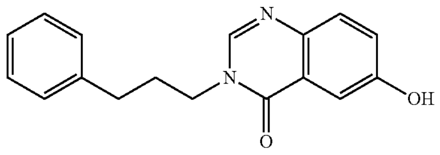 [SMILES: O=c1c2cc(O)ccc2ncn1CCCc1ccccc1] | 3-bromopropyl-benzene (CAS 637-59-2) | 281.2 [M + H]+ |
| IA6 | tert-butyl N-[3-(6-hydroxy-4-oxo-quinazolin-3-yl)propyl]-N-methyl-carbamate | 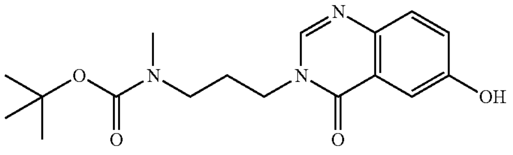 [SMILES: CN(CCCn1cnc2ccc(O)cc2c1=O)C(=O)OC(C)(C)C] | tert-butyl N-(3-bromopropyl)-N-methyl-carbamate (CAS 828272-19-1) | 332.3 [M − H]− |
| IA7 | tert-butyl 3-[2-(6-hydroxy-4-oxo-quinazolin-3-yl)ethyl]piperidine-1-carboxylate | 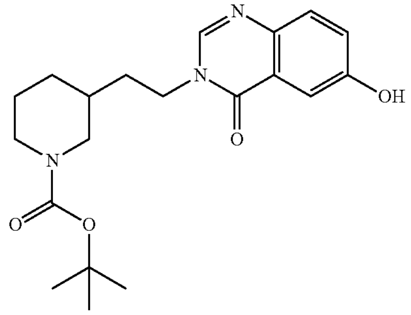 [SMILES: CC(C)(C)OC(=O)N1CCCC(CCn2cnc3ccc(O)cc3c2=O)C1] | tert-butyl 3-(2-bromoethyl) piperidine-1-carboxylate (CAS 210564-54-8) | 372.4 [M − H]− |

IA8: tert-butyl N-[[4-[3-(6-hydroxy-4-oxo-quinazolin-3-yl)propyl]phenyl]methyl]-N-methyl-carbamate

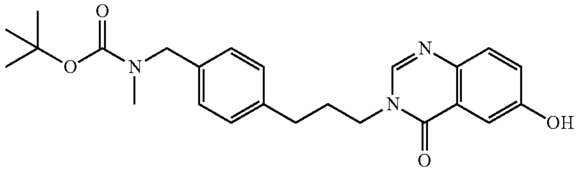 [SMILES: CN(Cc1ccc(CCCn2cnc3ccc(O)cc3c2=O)cc1)C(=O)OC(C)(C)C]

Step 1: tert-butyl 3-[4-[(tert-butoxycarbonylamino)methyl]phenyl]propanoate

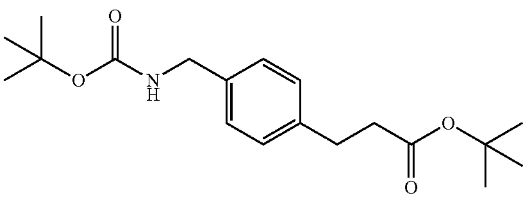 [SMILES: CC(C)(C)OC(=O)CCc1ccc(CNC(=O)OC(C)(C)C)cc1]

tert-Butyl 3-(4-cyanophenyl)propanoate (2.43 g, 10.5 mmol, Eq: 1.0) was dissolved in methanol (104 mL), THF (43.4 mL) and acetic acid (8.7 mL) in an autoclave. Palladium on carbon (10% loading, Degussa type E101, 782 mg, 735 μmol, Eq: 0.07) was added, and the reaction mixture was stirred under a hydrogen atmosphere (3 bar) for 1 h at rt. The reaction mixture was filtered (dicalite), the solvent was evaporated, and the crude product was dried. The residue was dissolved in EtOAc and washed with sat. aq. $NaHCO_3$, the aqueous layer (pH 7) was extracted 2× with EtOAc, the combined organic layers were washed with brine, dried over Na2SO4, filtered and concentrated in vacuo to give a light yellow viscous oil (2.24 g) which was used in without purification in the next step. 1H NMR (300 MHz, CHLOROFORM-d) δ ppm 1.42 (s, 9H) 2.46-2.60 (m, 2H) 2.83-2.97 (m, 2H) 3.84 (s, 2H) 7.06-7.26 (m, 4H).

To a solution of presumed tert-butyl 3-[4-(aminomethyl)phenyl]propanoate (2.24 g) in DCM (45 mL) was added di-tert-butyl dicarbonate (2.24 g, 10.3 mmol, Eq: 1.35) at rt. The reaction mixture was stirred at rt for 16 h 45 min, then washed with sat. aq. $NaHCO_3$. The organic layer was dried over Na2SO4, filtrated and evaporated. The residue was diluted with EtOAc purified by flash chromatography (Isco CombiFlash Companion, SILICYCLE FLH-R10017B-IS080, SiliaSep TM, HP 80 g, with 0% to 15% EtOAc in heptane) to give the title compound as a colourless viscous oil (2.21 g, 63% yield). 1H NMR (300 MHz, CHLOROFORM-d) δ ppm 1.42 (s, 9H) 1.46 (s, 9H) 2.42-2.64 (m, 2H) 2.78-3.01 (m, 2H) 4.28 (br d, J=5.6 Hz, 2H) 4.59-5.02 (m, 1H) 7.12-7.24 (m, 4H).

Step 2: tert-butyl 3-[4-[[tert-butoxycarbonyl(methyl)amino]methyl]phenyl]propanoate

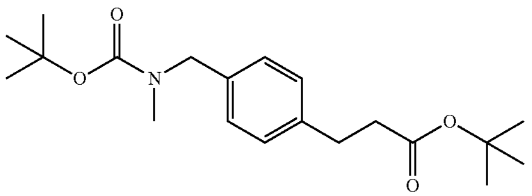 [SMILES: CN(Cc1ccc(CCC(=O)OC(C)(C)C)cc1)C(=O)OC(C)(C)C]

NaH (60% in mineral oil, 238 mg, 5.96 mmol, Eq: 2.5) was added to a clear solution of tert-butyl 3-[4-[(tert-butoxycarbonylamino)methyl]phenyl]propanoate (800 mg, 2.38 mmol, Eq: 1.0) in DMF (16 mL) at 0° C. The reaction was stirred at rt for 30 min before it was cooled down to 0° C. again and methyl iodide (1.35 g, 596 μL, 9.54 mmol, Eq: 4.0) was added. The reaction was stirred 15 min at 0° C. then allowed to warm up to rt. After 30 min, the reaction was cooled to 0° C. and sat. aq. NH4Cl solution was added carefully (dropwise) to the reaction mixture, which was then extracted with EtOAc. The organic layer was dried over Na2SO4, filtered and concentrated in vacuo to give the title compound as a light yellow oil (889 mg, 94% purity, 100% yield). MS (ESI) m/z: 292.2 [M−H−C4H8]−.

Step 3: tert-butyl N-[[4-(3-hydroxypropyl)phenyl]methyl]-N-methyl-carbamate

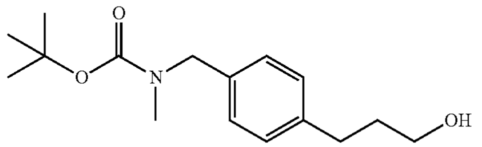 [SMILES: CN(Cc1ccc(CCCO)cc1)C(=O)OC(C)(C)C]

tert-butyl 3-[4-[[tert-butoxycarbonyl(methyl)amino]methyl]phenyl]propanoate (597 mg, 1.71 mmol, Eq: 1.0) was dissolved in THF (11 mL). LiBH4 (2 M in THF, 2.56 mL, 5.12 mmol, Eq: 3.0) was added dropwise at 0° C. The reaction mixture was stirred for 20 min at rt, the reaction was cooled to 0° C. then ethanol (472 mg, 598 μL, 10.2 mmol, Eq: 6.0) was added dropwise. The reaction was stirred for 30 min at 0° C. and after then at rt for 4.5 h. The reaction mixture was cooled to 0° C. and LiBH4 (2 M in THF, 427 μL, 854 μmol, Eq: 0.5) was added dropwise. The reaction was stirred at rt for 16 h 15 min, then cooled to 0° C. and carefully quenched with sat. aq. NH4Cl. The mixture was extracted 2× with EtOAc. The combined organic layers were washed 1× with brine and then dried with Na2SO4, filtered and concentrated in vacuo. The residue was diluted with DCM, evaporated with silica gel to dryness and transferred to a column. Purification by flash chromatography (40 g silica, 0-75% EtOAc in heptane) gave the title compound as a colourless viscous oil (437 mg, 92% yield). MS (ESI) m/z: 224.2 [M+H−C4H8]+.

Step 4: tert-butyl N-[[4-(3-bromopropyl)phenyl]methyl]-N-methyl-carbamate

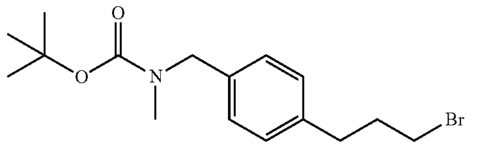 [SMILES: CN(Cc1ccc(CCCBr)cc1)C(=O)OC(C)(C)C]

In a three-necked flask, triphenylphosphine (883 mg, 3.27 mmol, Eq: 2.1) was dissolved in DCM (3 mL). At 0° C. a solution of carbon tetrabromide (1.11 g, 3.27 mmol, Eq: 2.1) in DCM (3 mL) was added dropwise then a solution of tert-butyl N-[[4-(3-hydroxypropyl)phenyl]methyl]-N-methyl-carbamate (435 mg, 1.56 mmol, Eq: 1.0) in DCM (6 mL) was added. The reaction mixture was warmed to rt over 17 h, then diluted with DCM, evaporated with silica gel to dryness and transferred to a column. Purification by flash chromatography (40 g silica, with 0-20% EtOAc in heptane) gave the title compound as a colourless viscous oil (256 mg, 48% yield). MS (ESI) m/z: 286.1, 288.1 [M+H−C4H8]+.

Step 5: tert-butyl N-[[4-[3-(6-bromo-4-oxo-quinazolin-3-yl)propyl]phenyl]methyl]-N-methyl-carbamate

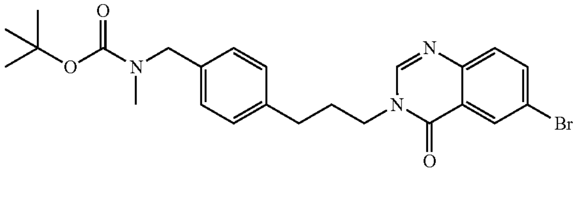 [SMILES: CN(Cc1ccc(CCCn2cnc3ccc(Br)cc3c2=O)cc1)C(=O)OC(C)(C)C]

tert-butyl N-[[4-(3-bromopropyl)phenyl]methyl]-N-methyl-carbamate (253 mg, 740 μmol, Eq: 1.2), 6-bromoquinazolin-4(3H)-one (146 mg, 616 μmol, Eq: 1.0) and Cs2CO3 (241 mg, 740 μmol, Eq: 1.2) were combined with DMF (7 mL) to give a white suspension. The reaction was stirred at rt for 15 h 45 min, then concentrated in vacuo. The residue was diluted with DCM, evaporated with silica gel to dryness and transferred to a column. Purification by flash chromatography (40 g silica, 0-67% EtOAc in heptane) gave the title compound as a white foam (289 mg, 97% yield). MS (ESI) m/z: 486.3, 488.3 [M+H]+.

Step 6: tert-butyl N-[[4-[3-(6-hydroxy-4-oxo-quinazolin-3-yl)propyl]phenyl]methyl]-N-methyl-carbamate

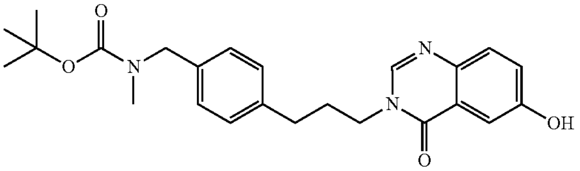 [SMILES: CN(Cc1ccc(CCCn2cnc3ccc(O)cc3c2=O)cc1)C(=O)OC(C)(C)C]

Under argon in a microwave vial, KOH (152 mg, 2.33 mmol, Eq: 4.0) was dissolved in water (3.5 mL) then dioxane (5 mL) was added. The mixture was flushed with argon, then tBuXPhos (15.3 mg, 35 μmol, Eq: 0.06), tris(dibenzylideneacetone)dipalladium (0) chloroform adduct (18.1 mg, 17.5 μmol, Eq: 0.03) and tert-butyl N-[[4-[3-(6-bromo-4-oxo-quinazolin-3-yl)propyl]phenyl]methyl]-N-methyl-carbamate (283.7 mg, 583 μmol, Eq: 1.0) were added. The reaction was flushed with argon again, and the vial was closed. The reaction mixture was heated to 105° C. and stirred for 1 h, then cooled to rt. The reaction mixture was diluted with 5 mL water and extracted 3× with diethyl ether. The organic layers were washed with 5 mL water, then the combined aq. layers was acidified with HCl (0.5 M aq. solution, 4.67 mL, 2.33 mmol, Eq: 4.0) and extracted 2× with EtOAc. The combined organic layers were washed 1× with brine, dried over Na2SO4, filtered and the solvent was evaporated. The residue was dried at high vacuum to give the title compound as a light brown solid (226 mg, 91%). MS (ESI) m/z 424.4 [M+H]+.

IA9: tert-butyl 4-[6-(2-cyano-3,6-difluoro-phenoxy)-4-oxo-quinazolin-3-yl]butanoate

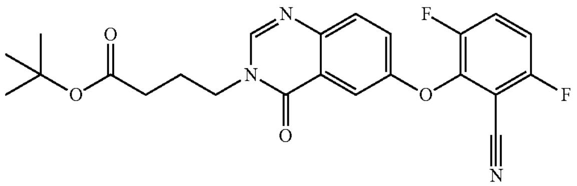 [SMILES: CC(C)(C)OC(=O)CCCn1cnc2ccc(Oc3c(F)ccc(F)c3C#N)cc2c1=O]

NaH (60% in mineral oil, 16.5 mg, 378 μmol, Eq: 1.15) was added at 0° C. to a solution of IA1 [tert-butyl 4-(6-hydroxy-4-oxoquinazolin-3(4H)-yl)butanoate] (100 mg, 329 μmol, Eq: 1.0) in DMF (2 mL). The cooling bath was removed and the reaction mixture was stirred at rt for 15 min. The reaction mixture was cooled again to 0° C. and a solution of 2,3,6-trifluorobenzonitrile (52.7 mg, 329 μmol, Eq: 1.0) in DMF (500 μL) was added. The mixture was allowed to stir at rt for 45 min, then concentrated in vacuo. The residue was diluted with DCM, evaporated with silica gel to dryness and transferred to a column. Purification by flash chromatography (40 g silica, 0-100% EtOAc in heptane) gave the title compound as a white foam (114 mg, 79% yield). MS (ESI) m/z: 442.3 [M+H]+.

IA10: tert-butyl 4-[2-[6-(2-cyano-3,6-difluoro-phenoxy)-4-oxo-quinazolin-3-yl]ethyl]piperidine-1-carboxylate

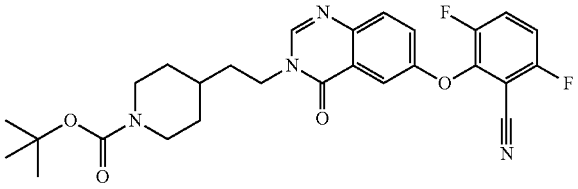 [SMILES: CC(C)(C)OC(=O)N1CCC(CCn2cnc3ccc(Oc4c(F)ccc(F)c4C#N)cc3c2=O)CC1]

Cs2CO3 (892 mg, 2.71 mmol, Eq: 1.15) was added at rt to a solution of IA2 [tert-butyl 4-(2-(6-hydroxy-4-oxoquinazolin-3(4H)-yl)ethyl)piperidine-1-carboxylate] (880 mg, 2.36 mmol, Eq: 1.0) in DMF (20 mL). The mixture was stirred for 30 min at rt then a solution of 2,3,6-trifluorobenzonitrile (416 mg, 2.59 mmol, Eq: 1.1) in DMF (6 mL) was added. The reaction mixture was stirred at rt for 2.5 h, then concentrated in vacuo. The residue was diluted with DCM, evaporated with silica gel to dryness and transferred to a column. Purification by flash chromatography (40 g silica, 0-100% EtOAc in heptane) gave the title compound as a viscous colourless oil (1.13 g, 94% yield). MS (ESI) m/z: 411.3 [M+H−Boc]+.

The following intermediates were prepared by analogy to intermediate IA10 using the appropriate phenol reagent (yields from 76% to 85%):

| IA | Systematic name | Structure | Phenol reagent | MS (ESI) |
|---|---|---|---|---|
| IA11 | tert-butyl N-[3-[6-(2-cyano-3,6-difluoro-phenoxy)-4-oxo-quinazolin-3-yl]propyl] carbamate | 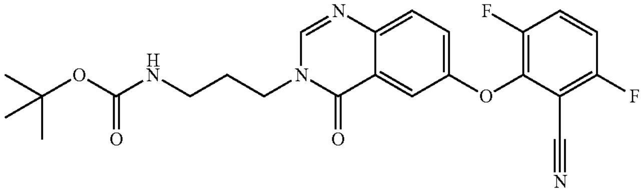 [SMILES: CC(C)(C)OC(=O)NCCCn1cnc2ccc(Oc3c(F)ccc(F)c3C#N)cc2c1=O] | IA3 | 401.2 [M + H − C4H8]+ |
| IA12 | tert-butyl 4-[2-[6-(2-cyano-3,6-difluoro-phenoxy)-4-oxo-quinazolin-3-yl]ethyl]piperazine-1-carboxylate | 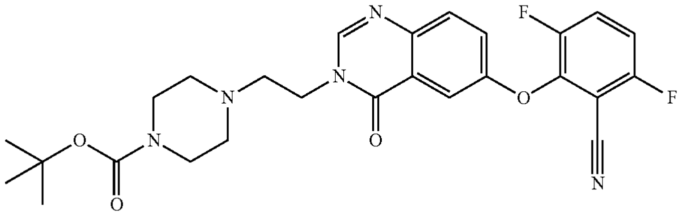 [SMILES: CC(C)(C)OC(=O)N1CCN(CCn2cnc3ccc(Oc4c(F)ccc(F)c4C#N)cc3c2=O)CC1] | IA4 | 512.4 [M + H]+ |
| IA13 | 3,6-difluoro-2-[4-oxo-3-(3-phenylpropyl) quinazolin-6-yl]oxy-benzonitrile | 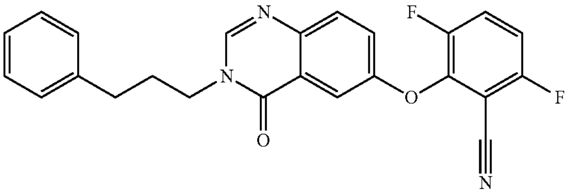 [SMILES: N#Cc1c(F)ccc(F)c1Oc1ccc2ncn(CCCc3ccccc3)c(=O)c2c1] | IA5 | 418.3 [M + H]+ |
| IA14 | tert-butyl N-[3-[6-(2-cyano-3,6-difluoro-phenoxy)-4-oxo-quinazolin-3-yl]propyl]-N-methyl-carbamate | 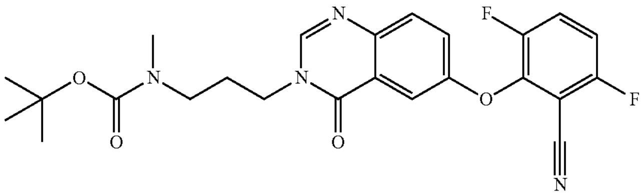 [SMILES: CN(CCCn1cnc2ccc(Oc3c(F)ccc(F)c3C#N)cc2c1=O)C(=O)OC(C)(C)C] | IA6 | 371.3 [M + H − Boc]+ |

-continued

| IA | Systematic name | Structure | Phenol reagent | MS (ESI) |
|---|---|---|---|---|
| IA15 | tert-butyl 3-[2-[6-(2-cyano-3,6-difluoro-phenoxy)-4-oxo-quinazolin-3-yl]ethyl]piperidine-1-carboxylate | 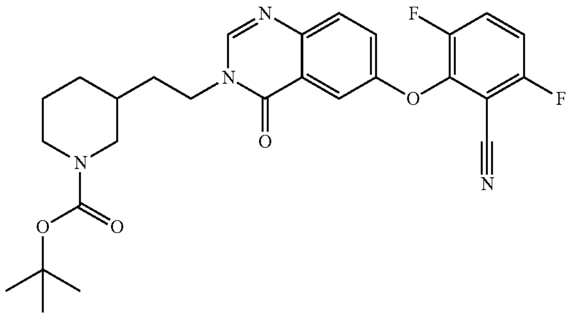 [SMILES: CC(C)(C)OC(=O)N1CCCC(CCn2cnc3ccc(Oc4c(F)ccc(F)c4C#N)cc3c2=O)C1] | IA7 | 455.3 [M + H − C4H8]+ |
| IA16 | tert-butyl N-[[4-[3-[6-(2-cyano-3,6-difluoro-phenoxy)-4-oxo-quinazolin-3-yl]propyl]phenyl]methyl]-N-methyl-carbamate | 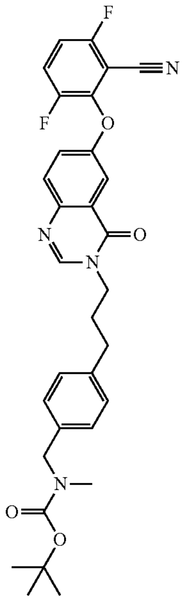 [SMILES: CN(Cc1ccc(CCCn2cnc3ccc(Oc4c(F)ccc(F)c4C#N)cc3c2=O)cc1)C(=O)OC(C)(C)C] | IA8 | 561.4 [M + H]+ |

Intermediates B (IBs)

IB1: 1-amino-2-cyano-3-[[ethyl(methyl)sulfamoyl]amino]benzene

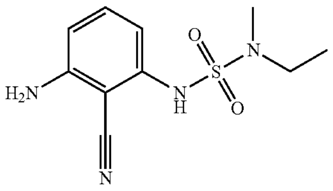 [SMILES: CCN(C)S(=O)(=O)Nc1cccc(N)c1C#N]

Step 1: 2-cyano-1-[[ethyl(methyl)sulfamoyl]amino]-3-nitro-benzene

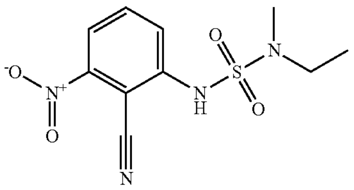

2,6-Dinitrobenzonitrile (1.46 g, 7.56 mmol, Eq: 1.1) was dissolved in DMF (15 mL). Cs2CO3 (2.46 g, 7.56 mmol, Eq: 1.1) and [methyl(sulfamoyl)amino]ethane (1 g, 6.87 mmol, Eq: 1.0) were added. The reaction mixture was stirred for 2 h at 65° C., then concentrated in vacuo. The residue was taken up in 2-methyl-THF and washed with water-brine solution, and the aqueous layer was extracted 2× with 2-methyl-THF. The organic layers were combined, dried with Na2SO4, filtered and concentrated in vacuo. The residue was diluted with DCM, evaporated with silica gel to dryness and transferred to a column. Purification by flash chromatography (40 g silica, 0-100% EtOAc in DCM) gave the title compound as a light red viscous oil (720 mg, 77% purity) which was used without further purification. MS (ESI) m/z: 285.1 [M+H]+.

Step 2: 1-amino-2-cyano-3-[[ethyl(methyl)sulfamoyl]amino]benzene

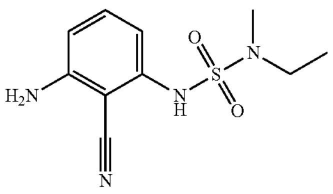 [SMILES: CCN(C)S(=O)(=O)Nc1cccc(N)c1C#N]

2-Cyano-1-[[ethyl(methyl)sulfamoyl]amino]-3-nitrobenzene (703 mg, 1.9 mmol, Eq: 1.0) was dissolved in MeOH (17 mL) and THF (7 mL), then Pd(OH)2 (Pearlman's catalyst, 26.7 mg, 190 μmol, Eq: 0.1) was added and the reaction mixture was stirred under a balloon of hydrogen at rt. After 1 h, the reaction mixture was filtered over a Whatman Spartan 30/0.45RC filter, and the filtrate was evaporated. The residue was diluted with EtOAc and transferred to a column. Purification by flash chromatography (80 g silica, 0-68% EtOAc in heptane) gave the title compound as a viscous orange oil (457 mg, 100% purity, 27% yield over two steps). MS (ESI) m/z: 255.1 [M+H]+.

IB2: (3R)—N-(3-amino-2-cyano-phenyl)-3-fluoro-pyrrolidine-1-sulfonamide

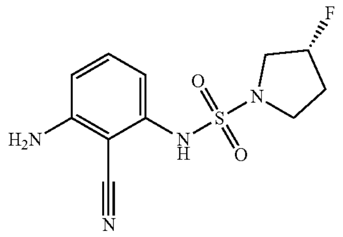 [SMILES: N#Cc1c(N)cccc1NS(=O)(=O)N1CC[C@@H](F)C1]

Step 1: (3R)—N-(2-cyano-3-nitro-phenyl)-3-fluoro-pyrrolidine-1-sulfonamide

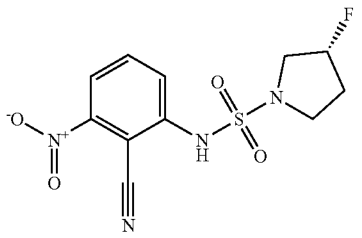

2,6-Dinitrobenzonitrile (900 mg, 4.66 mmol, Eq: 1.0) was dissolved in DMF (10 mL). Cs2CO3 (2.28 g, 6.99 mmol, Eq: 1.5) and Intermediate IC1 (1.18 g, 6.99 mmol, Eq: 1.5) were added. The reaction mixture was stirred for 1 h at 60° C., then concentrated in vacuo. The residue was taken up in 2-methyl-THF and washed with aq. NH4Cl solution, and the aqueous layer was extracted 1× with 2-methyl-THF. The organic layers were combined, dried with Na2SO4, filtrated and concentrated in vacuo. The residue was diluted with DCM, evaporated with silica gel to dryness and transferred to a column. Purification by flash chromatography (40 g silica, 0-100% EtOAc in DCM) gave the title compound as a light red viscous oil (795 mg). MS (ESI) m/z: 315.1 [M+H]+.

Step 2: (3R)—N-(3-amino-2-cyano-phenyl)-3-fluoro-pyrrolidine-1-sulfonamide

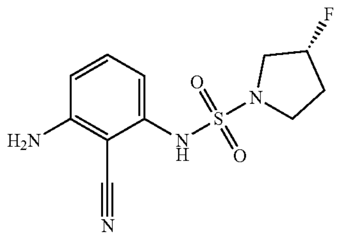 [SMILES: N#Cc1c(N)cccc1NS(=O)(=O)N1CC[C@@H](F)C1]

(3R)—N-(2-Cyano-3-nitro-phenyl)-3-fluoro-pyrrolidine-1-sulfonamide (751 mg, 2.39 mmol, Eq: 1.0) was dissolved in MeOH (13 mL) and THF (6 mL), then Pd(OH)2 (Pearlman's catalyst, 33.6 mg, 239 μmol, Eq: 0.1) was added and the reaction mixture was stirred under a balloon of hydrogen at rt. After 1 h, the reaction mixture was filtered over a Whatman Spartan 30/0.45RC filter, and the filtrate was evaporated. The residue was diluted with EtOAc and transferred to a column. Purification by flash chromatography (80 g silica, 0-79% EtOAc in heptane) gave the title compound as a viscous orange oil (560 mg, 100% purity, 42% yield over two steps). MS (ESI) m/z: 285.1 [M+H]+.

IB3: 1-amino-2-cyano-3-[[cyclopropyl(methyl)sulfamoyl]amino]benzene

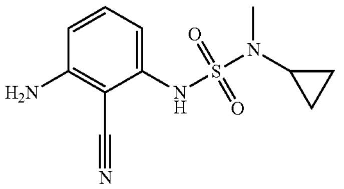 [SMILES: CN(C1CC1)S(=O)(=O)Nc1cccc(N)c1C#N]

Step 1: 2-cyano-1-[[cyclopropyl(methyl)sulfamoyl]amino]-3-nitro-benzene

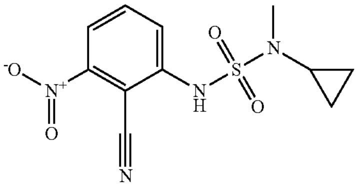

2,6-Dinitrobenzonitrile (167 mg, 865 μmol, Eq: 1.0) was dissolved in DMF (2 mL). Cs2CO3 (423 g, 1.3 mmol, Eq: 1.5) and Intermediate IC5 (195 mg, 1.3 mmol, Eq: 1.5) were added. The reaction mixture was stirred for 1 h at 60° C., then concentrated in vacuo. The residue was taken up in 2-methyl-THF and washed with water-brine solution, and the aqueous layer was extracted 2× with 2-methyl-THF. The organic layers were combined, dried with Na2SO4, filtrated and concentrated in vacuo. The residue was diluted with DCM, evaporated with silica gel to dryness and transferred to a column. Purification by flash chromatography (40 g silica, 0-100% EtOAc in DCM) gave the title compound as a light red solid (255 mg, ~65% purity). MS (ESI) m/z: 297.0 [M+H]+.

Step 2: 1-amino-2-cyano-3-[[cyclopropyl(methyl)sulfamoyl]amino]benzene

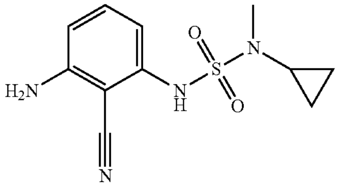 [SMILES: CN(C1CC1)S(=O)(=O)Nc1cccc(N)c1C#N]

2-Cyano-1-[[cyclopropyl(methyl)sulfamoyl]amino]-3-nitro-benzene (253 mg, 555 μmol, Eq: 1.0) was dissolved in MeOH (4 mL) and THF (2 mL), then Pd(OH)2 (Pearlman's catalyst, 7.8 mg, 56 μmol, Eq: 0.1) was added and the reaction mixture was stirred under a balloon of hydrogen at rt. After 2 h 10 min, the reaction mixture was filtered over a Whatman Spartan 30/0.45RC filter, and the filtrate was evaporated. The residue was diluted with EtOAc and transferred to a column. Purification by flash chromatography (40 g silica, 0-69% EtOAc in heptane) gave the title compound as an off-white solid (101 mg, 100% purity, 44% yield over two steps). MS (ESI) m/z: 267.1 [M+H]+.

IB4: N-(3-amino-2-cyano-phenyl)pyrrolidine-1-sulfonamide

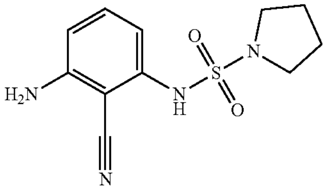 [SMILES: N#Cc1c(N)cccc1NS(=O)(=O)N1CCCC1]

Step 1: N-(2-cyano-3-nitro-phenyl)pyrrolidine-1-sulfonamide

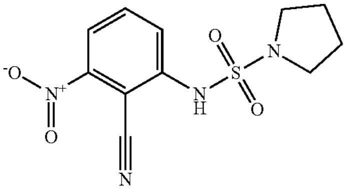

2,6-Dinitrobenzonitrile (1.00 g mg, 5.18 mmol, Eq: 1.0) was dissolved in DMF (10 mL). Cs2CO3 (2.53 g, 7.77 mmol, Eq: 1.5) and Intermediate IC2 (1.17 mg, 7.77 mmol, Eq: 1.5) were added. The reaction mixture was stirred for 1 h at 60° C., then concentrated in vacuo. The residue was taken up in 2-methyl-THF and washed with aq. NH4Cl solution, and the aqueous layer was extracted 1× with 2-methyl-THF. The organic layers were combined, dried with Na2SO4, filtered and concentrated in vacuo. The residue was suspended in 25 mL EtOAc and stirred for 15 min at rt, then filtered. The filter cake was washed with 3×8 mL Et2O and dried under vacuum to give the title compound as a red solid (380 mg). The filtrate was concentrated in vacuo, diluted with DCM, evaporated with silica gel to dryness and transferred to a column. Purification by flash chromatography (40 g silica, 0-100% EtOAc in DCM) gave the title compound as a red solid (642 mg, 67% combined yield). MS (ESI) m/z: 297.1 [M+H]+.

Step 2: N-(3-amino-2-cyano-phenyl)pyrrolidine-1-sulfonamide

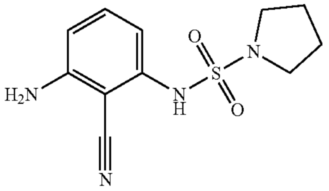 [SMILES: N#Cc1c(N)cccc1NS(=O)(=O)N1CCCC1]

N-(2-Cyano-3-nitro-phenyl)pyrrolidine-1-sulfonamide (614 mg, 2.07 mmol, Eq: 1.0) was dissolved in MeOH (10 mL) and THF (5 mL), then Pd(OH)2 (Pearlman's catalyst, 29.1 mg, 207 μmol Eq: 0.1) was added and the reaction mixture was stirred under a balloon of hydrogen at rt. After 1 h 7 min, the reaction mixture was filtered over a Whatman Spartan 30/0.45RC filter, and the filtrate was evaporated. The residue was diluted with EtOAc and transferred to a column. Purification by flash chromatography (40 g silica, 0-67% EtOAc in heptane) gave the title compound as a light yellow solid (374 mg, 100% purity, 68% yield). MS (ESI) m/z: 267.1 [M+H]+.

IB5: 2-[6-[2-cyano-3-[[ethyl(methyl)sulfamoyl]amino]anilino]-4-oxo-quinazolin-3-yl]acetic acid

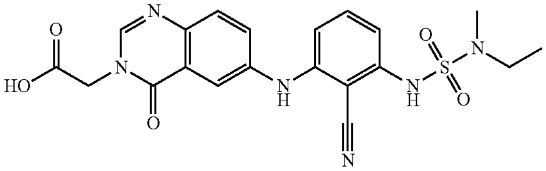 [SMILES: CCN(C)S(=O)(=O)Nc1cccc(Nc2ccc3ncn(CC(=O)O)c(=O)c3c2)c1C#N]

Step 1: tert-butyl 2-(6-bromo-4-oxo-quinazolin-3-yl)acetate

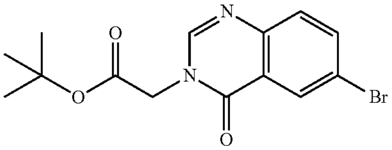 [SMILES: CC(C)(C)OC(=O)Cn1cnc2ccc(Br)cc2c1=O]

6-bromoquinazolin-4(3H)-one (1.0 g, 4.44 mmol, Eq: 1.0) and Cs2CO3 (2.17 g, 6.67 mmol, Eq: 1.5) were combined with DMF (12 mL). Then tert-butyl 2-bromoacetate (1.33 g, 997 μL, 6.67 mmol, Eq: 1.5) was added at rt. The reaction mixture was stirred at rt for 15 min, then concentrated in vacuo. The residue was diluted with DCM, evaporated with silica gel to dryness and transferred to a column. Purification by flash chromatography (40 g silica, 0-60% EtOAc in heptane) gave the title compound as a white solid (1.26 g, 100% purity, 83% yield). MS (ESI) m/z: 339.1, 341.1 [M+H]+.

Step 2: tert-butyl 2-[6-(3-amino-2-cyano-anilino)-4-oxo-quinazolin-3-yl]acetate

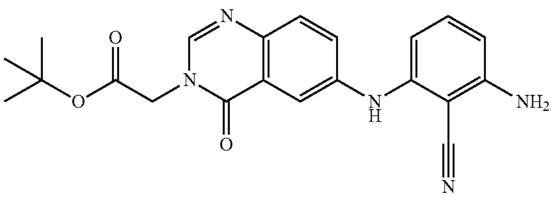 [SMILES: CC(C)(C)OC(=O)Cn1cnc2ccc(Nc3cccc(N)c3C#N)cc2c1=O]

In a vial, tert-butyl 2-(6-bromo-4-oxo-quinazolin-3-yl) acetate (100 mg, 295 μmol, Eq: 1.0) and 2,6-diaminobenzonitrile (39.3 mg, 295 μmol, Eq: 1.0) were dissolved in dioxane (10 mL) then Cs2CO3 (291 mg, 884 μmol, Eq: 3.0) was added. The reaction mixture was flushed with argon, then BippyPhos (9.23 mg, 17.7 μmol, Eq: 0.06) and tris (dibenzylideneacetone)dipalladium (0) chloroform adduct (9.34 mg, 8.84 μmol, Eq: 0.03) were added. The reaction was flushed with argon again, and the vial was closed. The reaction mixture was stirred at 110° C. for 2.5 h. The reaction mixture was taken up in 2-methyl-THF and ice, and washed with 1% aq. citric acid. The aqueous layer was back-extracted with 2-methyl-THF. The organic layers were combined, washed with brine, dried over Na2SO4 and concentrated in vacuo. The residue was diluted with EtOAc and transferred to a column. Purification by flash chromatography (40 g silica, gradient of EtOAc in heptane) gave the title compound as a light yellow solid (42 mg, 92% purity, 34% yield). MS (ESI) m/z: 392.3 [M+H]+.

Step 3: tert-butyl 2-[6-[2-cyano-3-[[ethyl(methyl)sulfamoyl]amino]anilino]-4-oxo-quinazolin-3-yl]acetate

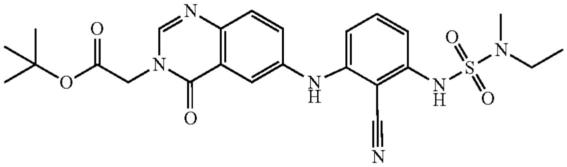 [SMILES: CCN(C)S(=O)(=O)Nc1cccc(Nc2ccc3ncn(CC(=O)OC(C)(C)C)c(=O)c3c2)c1C#N]

tert-Butyl 2-[6-(3-amino-2-cyano-anilino)-4-oxo-quinazolin-3-yl]acetate (40.3 mg, 94.7 μmol, Eq: 1.0) was suspended in DCM (600 μL). At rt, pyridine (345 mg, 351 μL, 4.36 mmol, Eq: 46), DMAP (590 μg, 4.74 μmol, Eq: 0.05) and N-ethyl-N-methyl-sulfamoyl chloride (29.9 mg, 23.4 μL 189 μmol, Eq: 2.0) were added. The reaction mixture was stirred at 70° C. for 17 h. The reaction mixture was taken up in 2-methyl-THF, ice and sat. aq. NaHCO3. The phases were separated, and the aqueous layer was back-extracted 2× with 2-methyl-THF. The organic layers were combined, washed with brine, dried over Na2SO4 and concentrated in vacuo. The residue was diluted with DCM and transferred to a column. Purification by flash chromatography (80 g silica, 0-100% EtOAc in heptane) gave the title compound as a light yellow foam (15 mg, 28% yield) containing ~10% starting material (tert-butyl 2-[6-(3-amino-2-cyano-anilino)-4-oxo-quinazolin-3-yl]acetate). MS (ESI) m/z: 513.3 [M+H]+.

Step 4: 2-[6-[2-cyano-3-[[ethyl(methyl)sulfamoyl]amino]anilino]-4-oxo-quinazolin-3-yl]acetic acid

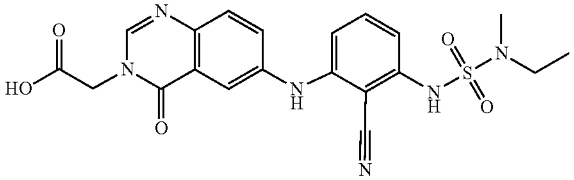 [SMILES: CCN(C)S(=O)(=O)Nc1cccc(Nc2ccc3ncn(CC(=O)O)c(=O)c3c2)c1C#N]

tert-Butyl 2-[6-[2-cyano-3-[[ethyl(methyl)sulfamoyl]amino]anilino]-4-oxo-quinazolin-3-yl]acetate was suspended in DCM (850 μL) and then trifluoroacetic acid (90.1 mg, 60.5 μL, 790 μmol, Eq: 30) was added at rt. The reaction mixture was stirred for 46 h, then concentrated in vacuo to give the title compound as a light brown semisolid (16.5 mg, 63% purity, 87% yield). MS (ESI) m/z: 457.2 [M+H]+.

IB6: tert-butyl 4-[(6-bromo-4-oxo-quinazolin-3-yl)methyl]piperidine-1-carboxylate

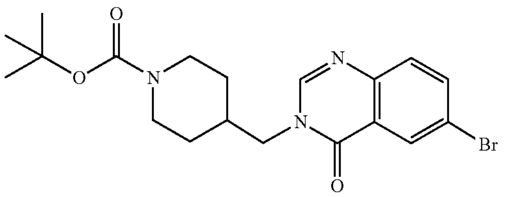 [SMILES: CC(C)(C)OC(=O)N1CCC(Cn2cnc3ccc(Br)cc3c2=O)CC1]

6-Bromoquinazolin-4(3H)-one (1.08 g, 4.8 mmol, Eq: 1.0) and Cs2CO3 (2.35 mg, 7.2 mmol, Eq: 1.5) were combined with DMF (15 mL) to give a brown suspension. tert-butyl 4-(bromomethyl)piperidine-1-carboxylate (2.0 g, 7.2 mmol, Eq: 1.5) was added at rt and the reaction mixture was stirred for 68 h at rt, then concentrated in vacuo. The residue was diluted with DCM, evaporated with silica gel to dryness and transferred to a column. Purification by flash chromatography (40 g silica, 0-100% EtOAc in heptane) gave the title compound as a white solid (1.82 mg, 90% yield). MS (ESI) m/z: 366.1, 368.1 [M+H–C4H8]+.

IB7: tert-butyl N-[2-[2-[2-(6-bromo-4-oxo-quinazolin-3-yl)ethoxy]ethoxy]ethyl]carbamate

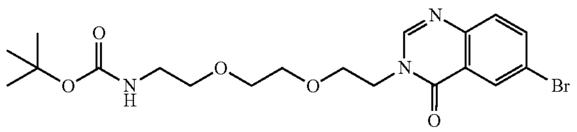 [SMILES: CC(C)(C)OC(=O)NCCOCCOCCn1cnc2ccc(Br)cc2c1=O]

Following the procedure described for Intermediate IB6, the title compound was obtained from 6-bromo-3H-quinazolin-4-one (75 mg, 333 μmol, Eq: 1.0) and tert-butyl N-[2-[2-(2-bromoethoxy)ethoxy]ethyl]carbamate (114 mg, 367 μmol, Eq: 1.1) as a light yellow viscous oil after flash chromatography (eluent EtOAc) (136 mg, 100% purity, 89% yield). MS (ESI) m/z: 456.2, 458.2 [M+H]+.

IB8: tert-butyl 4-(6-bromo-4-oxo-quinazolin-3-yl)butanoate

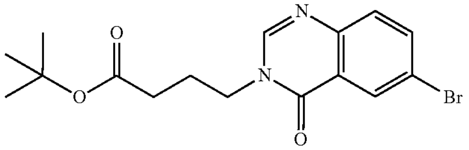 [SMILES: CC(C)(C)OC(=O)CCCn1cnc2ccc(Br)cc2c1=O]

Following the procedure described for Intermediate IB6, the title compound was obtained from 6-bromo-3H-quinazolin-4-one (1.0 g mg, 4.44 mmol, Eq: 1.0) and tert-butyl 4-bromobutanoate (1.52 g, 6.67 mmol, Eq: 1.5) as a white solid after flash chromatography (eluent 0-69% EtOAc in heptane) (1.49 mg, 100% purity, 91% yield). MS (ESI) m/z: 367.1, 369.1 [M+H]+.

IB9: 3-(2-benzyloxyethyl)-6-bromo-quinazolin-4-one

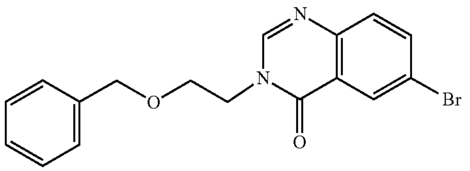 [SMILES: O=c1c2cc(Br)ccc2ncn1CCOCc1ccccc1]

Following the procedure described for Intermediate IB6, the title compound was obtained from 6-bromo-3H-quinazolin-4-one (500 mg, 2.22 mmol, Eq: 1.0) and 2-bromoethoxymethylbenzene (739 mg, 543 μL, 3.33 mmol, Eq: 1.5) as a white solid after flash chromatography (eluent 0-77% EtOAc in heptane) (738 mg, 100% purity, 93% yield). MS (ESI) m/z: 359.1, 361.1 [M+H]+.

IB10: tert-butyl 4-[2-(6-bromo-4-oxo-quinazolin-3-yl)ethyl]piperidine-1-carboxylate

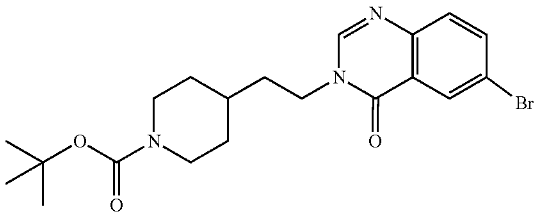 [SMILES: CC(C)(C)OC(=O)N1CCC(CCn2cnc3ccc(Br)cc3c2=O)CC1]

Following the procedure described for Intermediate IB6, the title compound was obtained from 6-bromo-3H-quinazolin-4-one (100 mg, 444 μmol, Eq: 1.0) and tert-butyl 4-(2-bromoethyl)piperidine-1-carboxylate (201 mg, 667 μmol, Eq: 1.5) as a white foam after flash chromatography (eluent 0-100% EtOAc in heptane) (171 mg, 100% purity, 88% yield). MS (ESI) m/z: 380.1, 382.1 [M+H–C4H8]+.

IB11: tert-butyl N-[3-(6-bromo-4-oxo-quinazolin-3-yl)propyl]carbamate

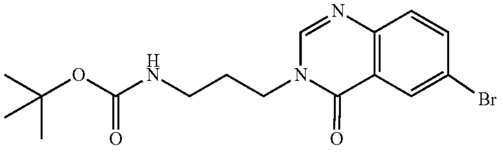 [SMILES: CC(C)(C)OC(=O)NCCCn1cnc2ccc(Br)cc2c1=O]

Following the procedure described for Intermediate IB6, the title compound was obtained from 6-bromo-3H-quinazolin-4-one (100 mg, 444 μmol, Eq: 1.0) and tert-butyl (3-bromopropyl)carbamate (165 mg, 667 μmol, Eq: 1.5) as a white foam after flash chromatography (eluent 0-100% EtOAc in heptane) (148 mg, 100% purity, 87% yield). MS (ESI) m/z: 382.4, 384.1 [M+H]+.

IB12: 6-bromo-3-(3-phenylpropyl)quinazolin-4-one

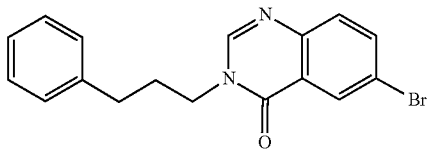 [SMILES: O=c1c2cc(Br)ccc2ncn1CCCc1ccccc1]

Following the procedure described for Intermediate IB6, the title compound was obtained from 6-bromo-3H-quinazolin-4-one (500 mg, 2.22 mmol, Eq: 1.0) and 3-bromopropylbenzene (677 mg, 517 μL, 3.33 mmol, Eq: 1.5) as a white solid after flash chromatography (eluent 0-74.5% EtOAc in heptane) (689 mg, 100% purity, 90% yield). MS (ESI) m/z: 343.1, 345.1 [M+H]+.

Intermediates C (ICs)

IC1: (3R)-3-fluoropyrrolidine-1-sulfonamide

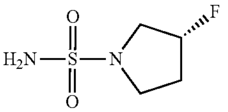

(R)-3-Fluoropyrrolidine hydrochloride (1.8 g, 14.3 mmol, Eq: 1.2) was added to a solution of sulfuric diamide (1.148 g, 11.9 mmol, Eq: 1.0) and triethylamine (2.42 g, 3.33 mL, 23.9 mmol, Eq: 2.0) in dioxane (10 mL). The reaction was stirred in a sealed tube at 115° C. for 15.5 h then cooled to rt and concentrated in vacuo. The residue was diluted with DCM, evaporated with silica gel to dryness and transferred to a column. Purification by flash chromatography (40 g silica, 80% EtOAc) gave the title compound as a white crystalline solid (1.82 g, 91% yield). MS (ESI) m/z: 169.1 [M+H]+.

IC2: pyrrolidine-1-sulfonamide

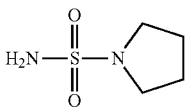

Pyrrolidine (1.78 g, 2.07 mL, 25 mmol, Eq: 1.2) was added to a solution of sulfuric diamide (2.0 g, 20.8 mmol, Eq: 1.0) in dioxane (20 mL). The reaction was stirred in a sealed tube at 115° C. for 15.5 h then cooled to rt and concentrated in vacuo. The residue was diluted with MeOH, evaporated with silica gel to dryness and transferred to a column. Purification by flash chromatography (40 g silica, 0-100% EtOAc in heptane) gave the title compound as a white solid (2.5 g, 80% yield). MS (ESI) m/z: 151.1 [M+H]+.

IC3: azetidine-1-sulfonamide

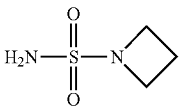

Azetidine hydrochloride (2.34 g, 25 mmol, Eq: 1.2) was added to a solution of sulfuric diamide (2 g, 20.8 mmol, Eq: 1.0) and triethylamine (4.21 g, 5.79 mL, 41.6 mmol, Eq: 2.0) in dioxane (17 mL). The reaction was stirred in a sealed tube at 115° C. for 20.25 h then cooled to rt and filtered.

The filtrate was concentrated in vacuo, diluted with DCM, evaporated with silica gel to dryness and transferred to a column. Purification by flash chromatography (40 g silica, 100% EtOAc) gave the title compound as a white solid (85 mg, 3% yield). MS (ESI) m/z: 137.0 [M+H]+.

IC4: piperidine-1-sulfonamide

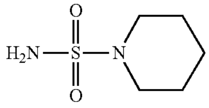

Piperidine (886 mg, 1.03 mL, 10.3 mmol, Eq: 1.0) was added to a solution of sulfuric diamide (1 g, 10.3 mmol, Eq: 1.0) in dioxane (10 mL). The reaction mixture was stirred in a sealed tube at 115° C. for 16 h, then concentrated in vacuo. The residue was diluted with MeOH, evaporated with silica gel to dryness and transferred to a column. Purification by flash chromatography (40 g silica, 0-100% EtOAc in heptane) gave the title compound as a white solid (965 mg, 57% yield). 1H NMR (300 MHz, DMSO-d6) δ ppm 1.37-1.49 (m, 2H) 1.50-1.65 (m, 4H) 2.81-3.01 (m, 4H) 6.65 (s, 2H).

IC5: [methyl(sulfamoyl)amino]cyclopropane

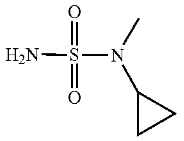

N-Methylcyclopropanamine oxalate (1.21 g, 7.49 mmol, Eq: 1.2) was added to a solution of sulfuric diamide (600 mg, 6.24 mmol, Eq: 1.0) and triethylamine (2.53 g, 3.48 mL, 25 mmol, Eq: 4.0) in dioxane (5 mL). The reaction mixture was stirred in a sealed tube for 16 h at 115° C., then concentrated in vacuo. The residue was diluted with DCM, evaporated with silica gel to dryness and transferred to a column. Purification by flash chromatography (40 g silica, 75% EtOAc in heptane) gave the title compound as a white crystalline solid (204 mg, 22% yield). 1H NMR (300 MHz, DMSO-d6) δ ppm 0.58-0.67 (m, 4H) 2.12-2.22 (m, 1H) 2.65 (s, 3H) 6.82 (s, 2H).

IC6: cyclopentanesulfonamide

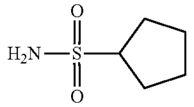

Cyclopentanesulfonyl chloride (675 mg, 619 μL, 4.0 mmol, Eq: 1.0) was added dropwise at rt to ammonium hydroxide solution (30-33% in water, 10.8 g, 12 mL, 92.5 mmol, Eq: 23.1). The reaction mixture was stirred overnight at rt. After 20.5 h, HCl (25% aq.) was added dropwise until the pH of the solution was 7. The reaction mixture was extracted 3× with EtOAc, the combined organic layers were washed 1× with brine, dried over Na2SO4, filtered and concentrated in vacuo. The residue was dried under high vacuum to give the title compound as a light brown solid (658 mg, 91% purity, 100% yield). 1H NMR (300 MHz, DMSO-d6) δ ppm 1.42-1.74 (m, 4H) 1.76-1.95 (m, 4H) 3.33-3.45 (m, 1H) 6.69 (s, 2H).

IC7: (RS)-butane-2-sulfonamide

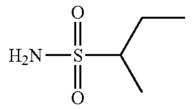

Following the procedure described for IC6, the title compound was obtained from butane-2-sulfonyl chloride (626 mg, 4 mmol) as a light yellow oil (397 mg, 73% yield). 1H NMR (300 MHz, CHLOROFORM-d) δ ppm 1.06 (t, J=7.5 Hz, 3H) 1.41 (d, J=6.9 Hz, 3H) 1.49-1.68 (m, 1H) 1.98-2.27 (m, 1H) 2.85-3.12 (m, 1H) 4.44 (br s, 2H).

IC8: cyclohexanesulfonamide

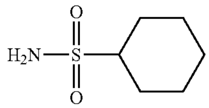

Following the procedure described for IC6, the title compound was obtained from cyclohexanesulfonyl chloride (568 mg, 2.8 mmol) as a white solid (371 mg, 81% yield). 1H NMR (300 MHz, DMSO-d6) δ ppm 1.14-1.41 (m, 5H) 1.55-1.69 (m, 1H) 1.72-1.86 (m, 2H) 2.06 (br d, J=10.7 Hz, 2H) 2.63-2.89 (m, 1H) 6.61 (s, 2H).

IC9: cyclobutanesulfonamide

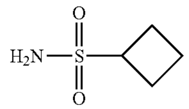

Following the procedure described for IC6, the title compound was obtained from cyclobutanesulfonyl chloride (462 mg, 2.98 mmol) as a white solid (309 mg, 77% yield). 1H NMR (300 MHz, DMSO-d6) δ ppm 1.79-1.97 (m, 2H) 2.14-2.35 (m, 4H) 3.56-3.83 (m, 1H) 6.71 (s, 2H).

Examples A

Example 1 tert-butyl 4-[6-[2-cyano-3-[[ethyl(methyl)sulfamoyl]amino]-6-fluoro-phenoxy]-4-oxo-quinazolin-3-yl]butanoate

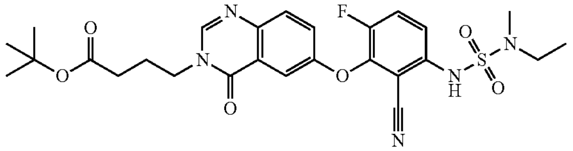 [SMILES: CCN(C)S(=O)(=O)Nc1ccc(F)c(Oc2ccc3ncn(CCCC(=O)OC(C)(C)C)c(=O)c3c2)c1C#N]

Ethyl-(methyl)sulfamoylamine (71 mg, 514 μmol, Eq: 2.1) was dissolved in NMP (2 mL). At 0° C. NaH (55% in mineral oil, 23.5 mg, 538 μmol, Eq: 2.2) was added, the cooling bath was removed and the reaction mixture was stirred at 50° C. for 30 min. The reaction mixture was cooled to 0° C., then a solution of intermediate IA9 [3,6-difluoro-2-((3-methyl-4-oxo-3,4-dihydroquinazolin-6-yl)oxy)benzonitrile] (108 mg, 245 μmol, Eq: 1.0) in NMP (1 mL) was added. The reaction mixture was stirred at 125° C. for 1 h. The reaction was cooled to rt, and the reaction mixture was taken up in 3.8 mL 0.1 M aq. NaOH, ice and EtOAc. The aq. layer was separated and extracted again with EtOAc. The organic layers were washed with sat. aq. NH4Cl. The aqueous layer was acidified with 2 M aq. HCl to pH 4 and extracted 2× with EtOAc. The combined organic layers were washed 3× with water, 1× with brine, then dried over Na2SO4, filtered and evaporated. The residue was diluted with DCM, evaporated with silica gel to dryness and transferred to a column. Purification by flash chromatography (0-100% EtOAc in heptane) gave the title compound as a white foam (39 mg, 100% purity, 28% yield). MS (ESI) m/z: 560.2 [M+H]+.

Example 2 tert-butyl 4-[2-[6-[2-cyano-6-fluoro-3-[[(3R)-3-fluoropyrrolidin-1-yl]sulfonylamino]phenoxy]-4-oxo-quinazolin-3-yl]ethyl]piperidine-1-carboxylate

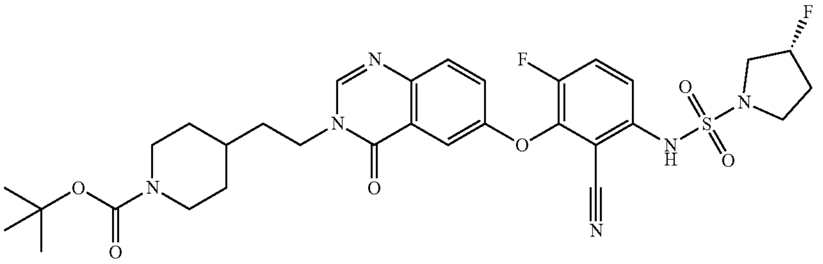

Intermediate IC1 (31.8 mg, 189 μmol, Eq: 2.1) was dissolved in DMF (500 μL). At rt, Cs2CO3 (64.6 mg, 198 μmol, Eq: 2.2) was added, and the reaction mixture was stirred at 50° C. for 30 min. The reaction mixture was cooled to rt and a solution of intermediate IA10 (46 mg, 90.1 μmol, Eq: 1.0) in DMF (1.1 mL) was added. The reaction mixture was stirred at 105° C. for 3 h, then concentrated in vacuo. The residue was taken up in DCM and washed with sat. aq. NH4Cl. The organic layer was dried over Na2SO4, filtrated and evaporated. The residue was diluted with DCM and transferred to a column. Purification by flash chromatography (40 g silica, with 0-100% EtOAc in DCM) gave the title compound as a white foam (18 mg, 99% purity) along with mixed fractions which were further purified by SFC to give further title compound as a white foam (17 mg, 98% purity, overall yield 59%). MS (ESI) m/z: 657.5 [M−H]−.

Example 3 tert-butyl 4-[2-[6-[2-cyano-3-[[ethyl(methyl)sulfamoyl]amino]-6-fluoro-phenoxy]-4-oxo-quinazolin-3-yl]ethyl]piperidine-1-carboxylate

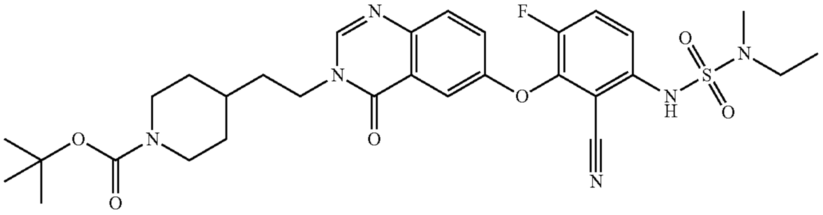

Following the procedure described for Example 1, the title compound was obtained from intermediate IA10 (85 mg, 166 μmol, Eq: 1.0) and [methyl(sulfamoyl)amino]ethane (48 mg, 350 μmol Eq: 2.1) as a white foam following additional purification by reversed phase HPLC (61 mg, 97% purity, 57% yield). MS (ESI) m/z: 627.2 [M−H]−.

Example 4 tert-butyl N-[3-[6-[2-cyano-6-fluoro-3-[[(3R)-3-fluoropyrrolidin-1-yl]sulfonylamino]phenoxy]-4-oxo-quinazolin-3-yl]propyl]carbamate

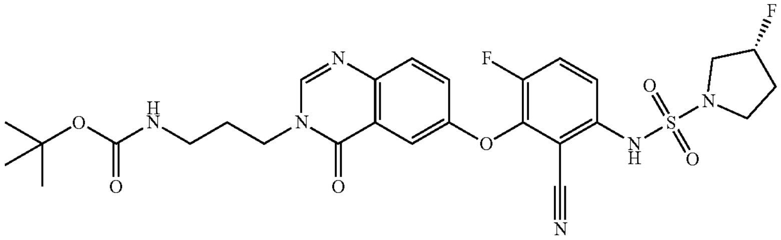 [SMILES: CC(C)(C)OC(=O)NCCCn1cnc2ccc(Oc3c(F)ccc(NS(=O)(=O)N4CC[C@@H](F)C4)c3C#N)cc2c1=O]

Following the procedure described for Example 2, the title compound was obtained from Intermediate IA11 (50 mg, 110 µmol, Eq: 1.0) and Intermediate IC1 (39 mg, 230 µmol, Eq: 2.1) as a white foam following SFC purification (36 mg, 100% purity, 54% yield). MS (ESI) m/z: 603.4 [M−H]−.

Example 5 tert-butyl N-[3-[6-[2-cyano-6-fluoro-3-(pyrrolidin-1-ylsulfonylamino)phenoxy]-4-oxo-quinazolin-3-yl]propyl]carbamate

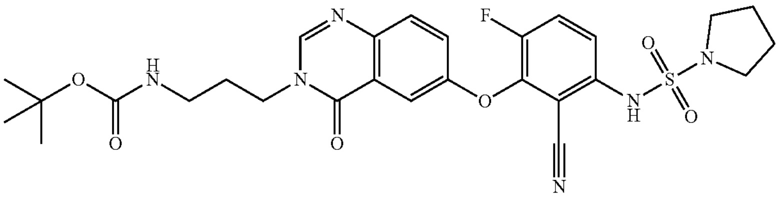 [SMILES: CC(C)(C)OC(=O)NCCCn1cnc2ccc(Oc3c(F)ccc(NS(=O)(=O)N4CCCC4)c3C#N)cc2c1=O]

Following the procedure described for Example 2, the title compound was obtained from Intermediate IA11 (55.7 mg, 122 µmol, Eq: 1.0) and Intermediate IC2 (38.5 mg, 256 µmol, Eq: 2.1) as a white foam following SFC purification (24 mg, 100% purity, 48% yield). MS (ESI) m/z: 585.4 [M−H]−.

Example 6 tert-butyl N-[3-[6-[2-cyano-3-[[ethyl(methyl)sulfamoyl]amino]-6-fluoro-phenoxy]-4-oxo-quinazolin-3-yl]propyl]carbamate

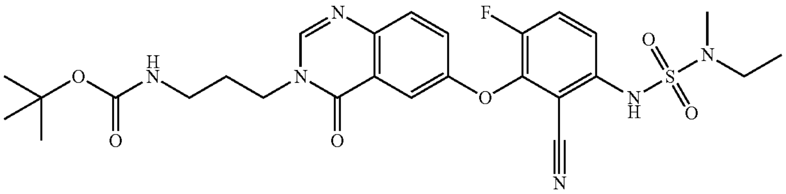 [SMILES: CCN(C)S(=O)(=O)Nc1ccc(F)c(Oc2ccc3ncn(CCCNC(=O)OC(C)(C)C)c(=O)c3c2)c1C#N]

Following the procedure described for Example 2, the title compound was obtained from Intermediate IA11 (53.81 mg, 118 µmol, Eq: 1.0) and [methyl(sulfamoyl)amino]ethane (36 mg, 248 µmol, Eq: 2.1) as a white foam following SFC purification (27.7 mg, 100% purity, 41% yield). MS (ESI) m/z: 573.5 [M−H]−.

Example 7 tert-butyl 4-[2-[6-[2-cyano-6-fluoro-3-(pyrrolidin-1-ylsulfonylamino)phenoxy]-4-oxo-quinazolin-3-yl]ethyl]piperidine-1-carboxylate

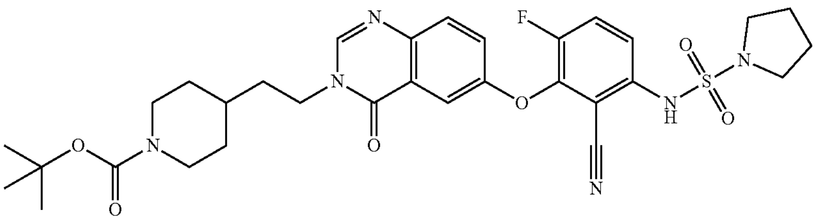 [SMILES: CC(C)(C)OC(=O)N1CCC(CCn2cnc3ccc(Oc4c(F)ccc(NS(=O)(=O)N5CCCC5)c4C#N)cc3c2=O)CC1]

Following the procedure described for Example 2, the title compound was obtained form Intermediate IA10 (79.5 mg, 156 μmol, Eq: 1.0) and Intermediate IC2 (49.1 mg, 327 μmol, Eq: 2.1) as a white foam following SFC purification (55 mg, 100% purity, 55% yield). MS (ESI) m/z: 639.5 [M–H]–.

Example 8 tert-butyl N-[3-[6-[2-cyano-3-(cyclopentylsulfonylamino)-6-fluoro-phenoxy]-4-oxo-quinazolin-3-yl]propyl]carbamate

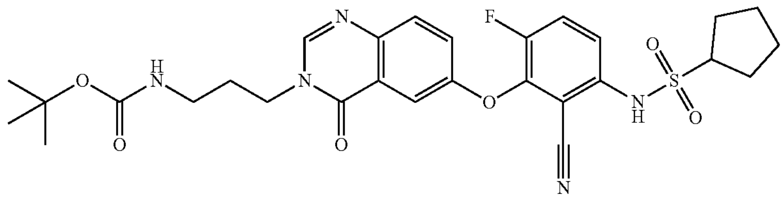

Following the procedure described for Example 2, the title compound was obtained from Intermediate IA11 (40 mg, 87.6 μmol, Eq: 1.0) and Intermediate IC6 (28.9 mg, 184 μmol, Eq: 2.1) as a white foam following SFC purification (34 mg, 97% purity, 64% yield). MS (ESI) m/z: 584.4 [M–H]–.

Example 9 tert-butyl N-[3-[6-[3-(azetidin-1-ylsulfonylamino)-2-cyano-6-fluoro-phenoxy]-4-oxo-quinazolin-3-yl]propyl]carbamate

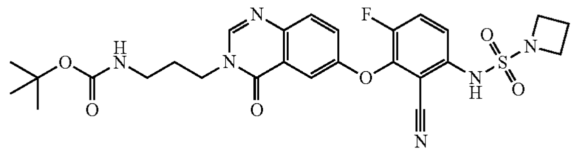 [SMILES: CC(C)(C)OC(=O)NCCCn1cnc2ccc(Oc3c(F)ccc(NS(=O)(=O)N4CCC4)c3C#N)cc2c1=O]

Following the procedure described for Example 2, the title compound was obtained from Intermediate IA11 (36 mg, 78.9 μmol, Eq: 1.0) and Intermediate IC3 (22.6 mg, 166 μmol, Eq: 2.1) as a white foam following SFC purification (25 mg, 100% purity, 55% yield). MS (ESI) m/z: 571.5 [M–H]–.

Example 10 tert-butyl 4-[2-[6-[2-cyano-6-fluoro-3-[[(3R)-3-fluoropyrrolidin-1-yl]sulfonylamino]phenoxy]-4-oxo-quinazolin-3-yl]ethyl]piperazine-1-carboxylate

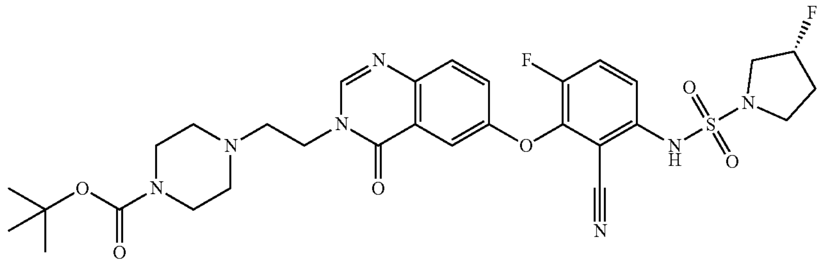 [SMILES: CC(C)(C)OC(=O)N1CCN(CCn2cnc3ccc(Oc4c(F)ccc(NS(=O)(=O)N5CC[C@@H](F)C5)c4C#N)cc3c2=O)CC1]

Following the procedure described for Example 2, the title compound was obtained from Intermediate IA12 (50 mg, 97.7 μmol, Eq: 1.0) and Intermediate IC1 (34.5 mg, 205 μmol, Eq: 2.1) as a white foam following SFC purification (39 mg, 100% purity, 61% yield). MS (ESI) m/z: 660.4 [M+H]+.

Example 11

N-[2-cyano-4-fluoro-3-[4-oxo-3-(3-phenylpropyl) quinazolin-6-yl]oxy-phenyl]cyclopentanesulfonamide

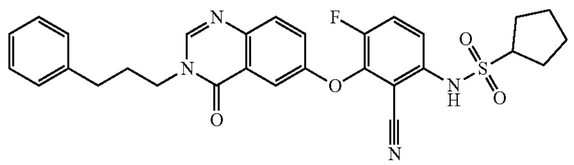 [SMILES: N#Cc1c(NS(=O)(=O)C2CCCC2)ccc(F)c1Oc1ccc2ncn(CCCc3ccccc3)c(=O)c2c1]

Following the procedure described for Example 2, the title compound was obtained from Intermediate IA13 (40 mg, 95.8 μmol, Eq: 1.0) and Intermediate IC6 (31.6 mg, 201 μmol, Eq: 2.1) as a white foam following SFC purification (18 mg, 100% purity, 34% yield). MS (ESI) m/z: 547.4 [M+H]+.

Example 12 tert-butyl N-[3-[6-[2-cyano-3-(cyclohexylsulfonylamino)-6-fluoro-phenoxy]-4-oxo-quinazolin-3-yl] propyl]carbamate

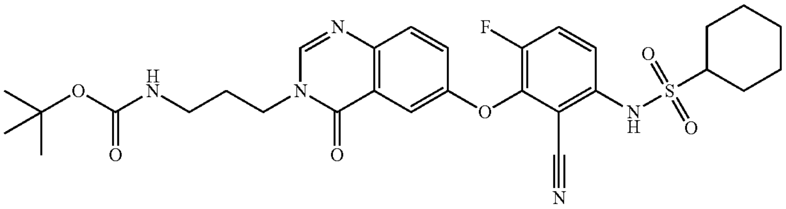 [SMILES: CC(C)(C)OC(=O)NCCCn1cnc2ccc(Oc3c(F)ccc(NS(=O)(=O)C4CCCCC4)c3C#N)cc2c1=O]

Following the procedure described for Example 2, the title compound was obtained from Intermediate IA11 (50 mg, 110 μmol, Eq: 1.0) and Intermediate IC8 (37.5 mg, 230 μmol, Eq: 2.1) as a white foam (46 mg, 100% purity, 70% yield). MS (ESI) m/z: 598.5 [M−H]−.

Example 13 tert-butyl N-[3-[6-[2-cyano-6-fluoro-3-(sec-butylsulfonylamino)phenoxy]-4-oxo-quinazolin-3-yl] propyl]carbamate

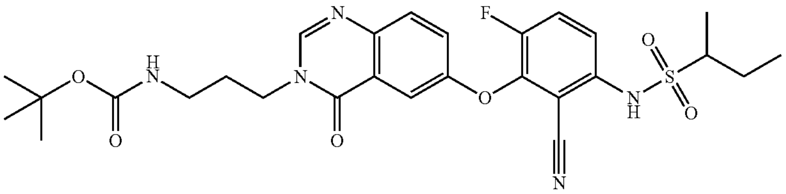 [SMILES: CCC(C)S(=O)(=O)Nc1ccc(F)c(Oc2ccc3ncn(CCCNC(=O)OC(C)(C)C)c(=O)c3c2)c1C#N]

Following the procedure described for Example 2, the title compound was obtained from Intermediate IA11 (50 mg, 110 μmol, Eq: 1.0) and Intermediate IC7 (31.6 mg, 230 μmol, Eq: 2.1) as a white foam (43 mg, 98% purity, 67% yield). MS (ESI) m/z: 572.5 [M−H]−.

Example 14 tert-butyl 4-[2-[6-[2-cyano-3-(cyclohexylsulfonylamino)-6-fluoro-phenoxy]-4-oxo-quinazolin-3-yl]ethyl]piperidine-1-carboxylate

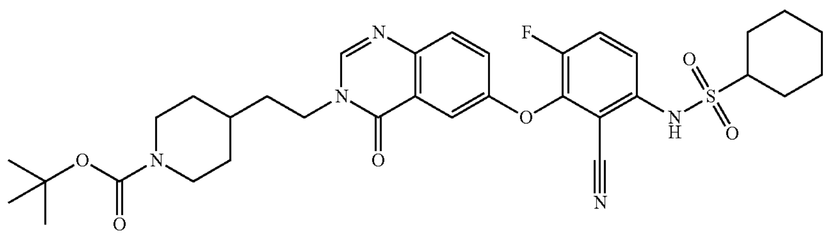 [SMILES: CC(C)(C)OC(=O)N1CCC(CCn2cnc3ccc(Oc4c(F)ccc(NS(=O)(=O)C5CCCCC5)c4C#N)cc3c2=O)CC1]

Following the procedure described for Example 2, the title compound was obtained from Intermediate IA10 (50 mg, 97.9 μmol, Eq: 1.0) and Intermediate IC8 (33.6 mg, 206 μmol, Eq: 2.1) as a white foam (45 mg, 100% purity, 70% yield). MS (ESI) m/z: 652.5 [M−H]−.

Example 15 tert-butyl 4-[2-[6-[2-cyano-6-fluoro-3-(sec-butylsulfonylamino)phenoxy]-4-oxo-quinazolin-3-yl]ethyl]piperidine-1-carboxylate

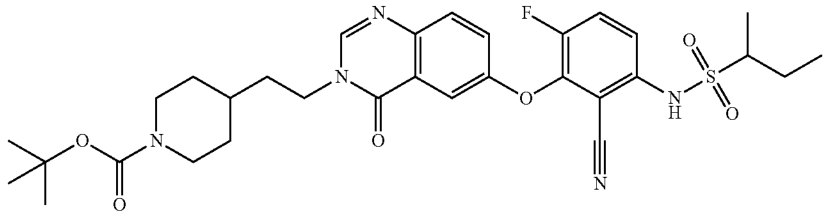

Following the procedure described for Example 2, the title compound was obtained from Intermediate IA10 (50 mg, 97.9 μmol, Eq: 1.0) and Intermediate IC7 (28.2 mg, 206 μmol, Eq: 2.1) as a white foam (45 mg, 100% purity, 73% yield). MS (ESI) m/z: 626.5 [M−H]−.

Example 16 tert-butyl 4-[2-[6-[2-cyano-6-fluoro-3-(pyrrolidin-1-ylsulfonylamino)phenoxy]-4-oxo-quinazolin-3-yl]ethyl]piperazine-1-carboxylate

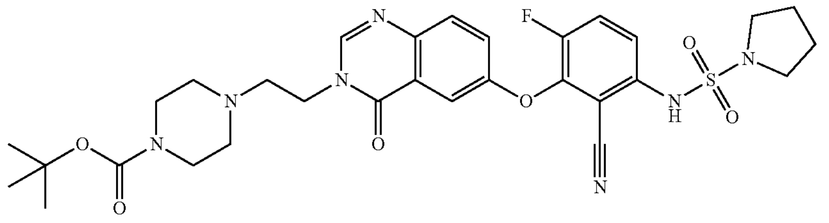

Following the procedure described for Example 2, the title compound was obtained from Intermediate IA12 (50 mg, 97.7 μmol, Eq: 1.0) and Intermediate IC2 (30.8 mg, 205 μmol, Eq: 2.1) as a white solid after SFC purification (33 mg, 100% purity, 53% yield). MS (ESI) m/z: 642.5 [M+H]+.

Example 17 tert-butyl 4-[2-[6-[2-cyano-3-(cyclopentylsulfonylamino)-6-fluoro-phenoxy]-4-oxo-quinazolin-3-yl]ethyl]piperidine-1-carboxylate

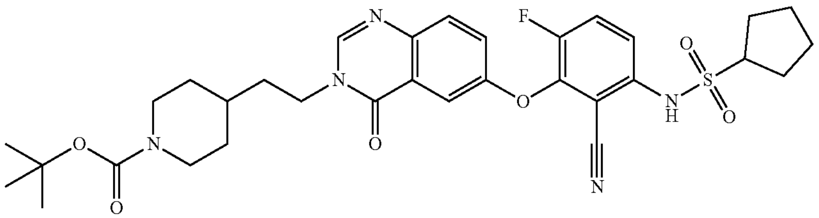 [SMILES: CC(C)(C)OC(=O)N1CCC(CCn2cnc3ccc(Oc4c(F)ccc(NS(=O)(=O)C5CCCC5)c4C#N)cc3c2=O)CC1]

Following the procedure described for Example 2, the title compound was obtained from Intermediate IA10 (50 mg, 97.9 μmol, Eq: 1.0) and Intermediate IC6 (30.7 mg, 206 μmol, Eq: 2.1) as a white foam after SFC purification (38 mg, 100% purity, 61% yield). MS (ESI) m/z: 638.6 [M−H]−.

Example 18 tert-butyl 4-[2-[6-[2-cyano-6-fluoro-3-(1-piperidylsulfonylamino)phenoxy]-4-oxo-quinazolin-3-yl]ethyl]piperidine-1-carboxylate

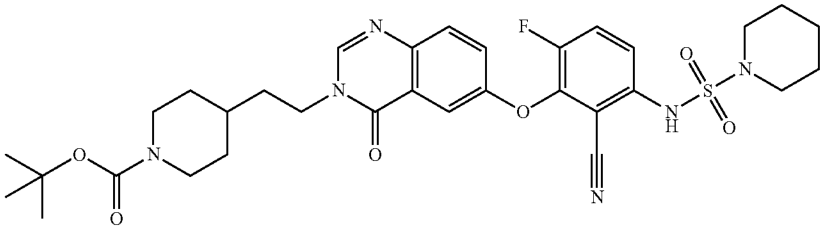 [SMILES: CC(C)(C)OC(=O)N1CCC(CCn2cnc3ccc(Oc4c(F)ccc(NS(=O)(=O)N5CCCCC5)c4C#N)cc3c2=O)CC1]

Following the procedure described for Example 2, the title compound was obtained from Intermediate IA10 (50 mg, 97.9 μmol, Eq: 1.0) and Intermediate IC4 (33.8 mg, 206 μmol, Eq: 2.1) as a white foam after SFC purification (38 mg, 100% purity, 60% yield). MS (ESI) m/z: 555.4 [M+H−Boc]+.

Example 19 tert-butyl N-[3-[6-[2-cyano-6-fluoro-3-(pyrrolidin-1-ylsulfonylamino)phenoxy]-4-oxo-quinazolin-3-yl]propyl]-N-methyl-carbamate

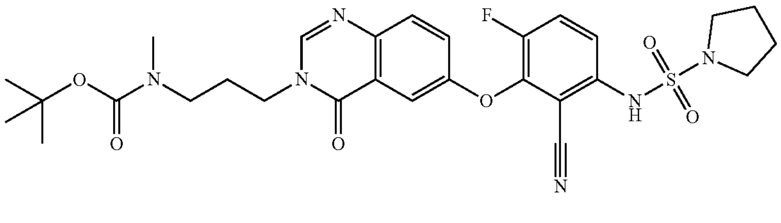 [SMILES: CN(CCCn1cnc2ccc(Oc3c(F)ccc(NS(=O)(=O)N4CCCC4)c3C#N)cc2c1=O)C(=O)OC(C)(C)C]

Following the procedure described for Example 2, the title compound was obtained from Intermediate IA14 (54.5 mg, 116 μmol, Eq: 1.0) and Intermediate IC2 (36.5 mg, 243 μmol, Eq: 2.1) as a white foam after SFC purification (37 mg, 100% purity, 53% yield). MS (ESI) m/z: 599.5 [M−H]−.

Example 20 tert-butyl N-[3-[6-[2-cyano-3-(cyclopentylsulfonylamino)-6-fluoro-phenoxy]-4-oxo-quinazolin-3-yl]propyl]-N-methyl-carbamate

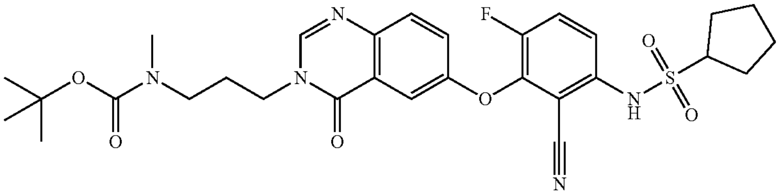 [SMILES: CN(CCCn1cnc2ccc(Oc3c(F)ccc(NS(=O)(=O)C4CCCC4)c3C#N)cc2c1=O)C(=O)OC(C)(C)C]

Following the procedure described for Example 2, the title compound was obtained from Intermediate IA14 (51 mg, 108 μmol, Eq: 1.0) and Intermediate IC6 (34 mg, 228 μmol, Eq: 2.1) as a white foam after SFC purification (45 mg, 100% purity, 69% yield). MS (ESI) m/z: 598.5 [M−H]−.

Example 21 tert-butyl 4-[2-[6-[2-cyano-3-(cyclobutylsulfonylamino)-6-fluoro-phenoxy]-4-oxo-quinazolin-3-yl]ethyl]piperidine-1-carboxylate

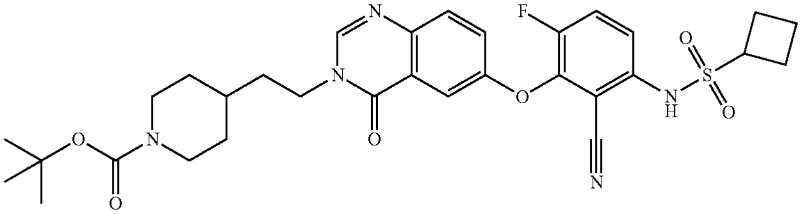 [SMILES: CC(C)(C)OC(=O)N1CCC(CCn2cnc3ccc(Oc4c(F)ccc(NS(=O)(=O)C5CCC5)c4C#N)cc3c2=O)CC1]

Following the procedure described for Example 2, the title compound was obtained from Intermediate IA10 (50 mg, 97.9 μmol, Eq: 1.0) and Intermediate IC9 (27.8 mg, 206 μmol, Eq: 2.1) as a white foam after SFC purification (38 mg, 100% purity, 62% yield). MS (ESI) m/z: 624.5 [M−H]−.

Example 22 tert-butyl 3-[2-[6-[2-cyano-3-(cyclopentylsulfonylamino)-6-fluoro-phenoxy]-4-oxo-quinazolin-3-yl]ethyl]piperidine-1-carboxylate

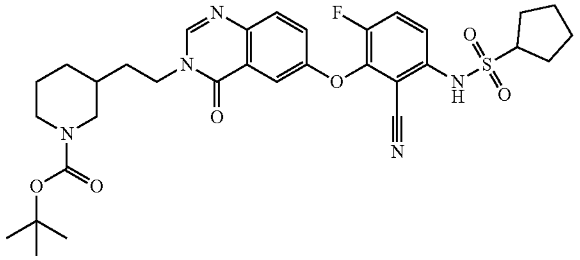 [SMILES: CC(C)(C)OC(=O)N1CCCC(CCn2cnc3ccc(Oc4c(F)ccc(NS(=O)(=O)C5CCCC5)c4C#N)cc3c2=O)C1]

Following the procedure described for Example 2, the title compound was obtained from Intermediate IA15 (50 mg, 97.9 μmol, Eq: 1.0) and Intermediate IC6 (30.7 mg, 206 μmol, Eq: 2.1) as a white foam after flash chromatography (eluent 0-100% EtOAc in DCM) (45 mg, 100% purity, 72% yield). MS (ESI) m/z: 638.6 [M−H]−.

Example 23 tert-butyl 3-[2-[6-[2-cyano-6-fluoro-3-(pyrrolidin-1-ylsulfonylamino)phenoxy]-4-oxo-quinazolin-3-yl]ethyl]piperidine-1-carboxylate

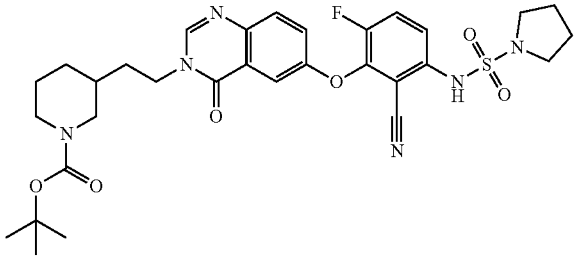 [SMILES: CC(C)(C)OC(=O)N1CCCC(CCn2cnc3ccc(Oc4c(F)ccc(NS(=O)(=O)N5CCCC5)c4C#N)cc3c2=O)C1]

Following the procedure described for Example 2, the title compound was obtained from Intermediate IA15 (55 mg, 108 μmol, Eq: 1.0) and Intermediate IC2 (34 mg, 226 μmol, Eq: 2.1) as a white foam after SFC (40.5 mg, 98% purity, 58% yield). MS (ESI) m/z: 639.5 [M−H]−.

Example 24

N-[3-[6-[2-cyano-3-(cyclopentyl sulfonylamino)-6-fluoro-phenoxy]-4-oxo-quinazolin-3-yl]propyl]-N-methyl-acetamide

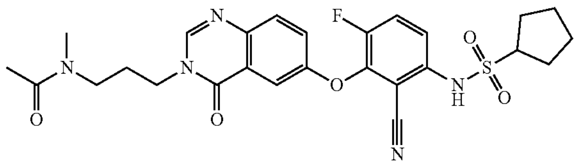 [SMILES: CC(=O)N(C)CCCn1cnc2ccc(Oc3c(F)ccc(NS(=O)(=O)C4CCCC4)c3C#N)cc2c1=O]

Step 1: N-[2-cyano-4-fluoro-3-[3-[3-(methylamino)propyl]-4-oxo-quinazolin-6-yl]oxy-phenyl]cyclopentanesulfonamide hydrochloride

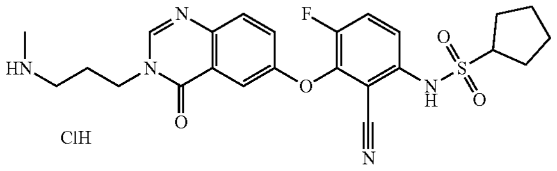 [SMILES: CNCCCn1cnc2ccc(Oc3c(F)ccc(NS(=O)(=O)C4CCCC4)c3C#N)cc2c1=O ; Cl]

Example 20 (30.8 mg, 51.4 μmol, Eq: 1.0) was dissolved in dioxane (210 μL). At rt, HCl (4 M in dioxane, 257 μL, 1.03 mmol, Eq: 20) was added. The reaction mixture was stirred at rt for 2 h 50 min, then concentrated in vacuo to give the title compound as a white solid (30.2 mg, 90% purity, 99% yield). MS (ESI) m/z: 498.5 [M−H]−.

Step 2: N-[3-[6-[2-cyano-3-(cyclopentylsulfonylamino)-6-fluoro-phenoxy]-4-oxo-quinazolin-3-yl]propyl]-N-methyl-acetamide

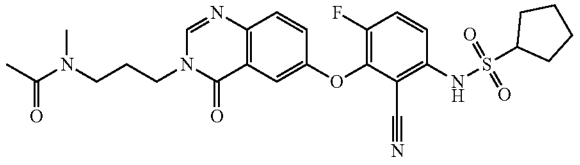 [SMILES: CC(=O)N(C)CCCn1cnc2ccc(Oc3c(F)ccc(NS(=O)(=O)C4CCCC4)c3C#N)cc2c1=O]

DIPEA (34.4 mg, 45.5 μL, 261 μmol, Eq: 5.55) was added to a stirred suspension of N-[2-cyano-4-fluoro-3-[3-[3-(methylamino)propyl]-4-oxo-quinazolin-6-yl]oxy-phenyl]cyclopentanesulfonamide hydrochloride (28 mg, 47 μmol, Eq: 1.0) in DMF (1.4 mL). The reaction mixture was cooled to 0° C. and acetic anhydride (7.73 mg, 7.16 μL, 75.7 μmol, Eq: 1.61) was added. The reaction mixture was stirred 40 min at 0° C. and then allowed to warm to rt. After 1 h 25 min, the reaction mixture was concentrated in vacuo. The residue was diluted with DCM, evaporated with silica gel to dryness and transferred to a column. Purification by flash chromatography (25 g silica, 0-9.2% MeOH in DCM) gave the title compound as a white foam (22 mg, 100% purity, 88% yield). MS (ESI) m/z: 542.4 [M+H]+.

Example 25 tert-butyl 4-[2-[6-[2-cyano-3-(cyclopentylsulfonylamino)-6-fluoro-phenoxy]-4-oxo-quinazolin-3-yl]ethyl]piperazine-1-carboxylate

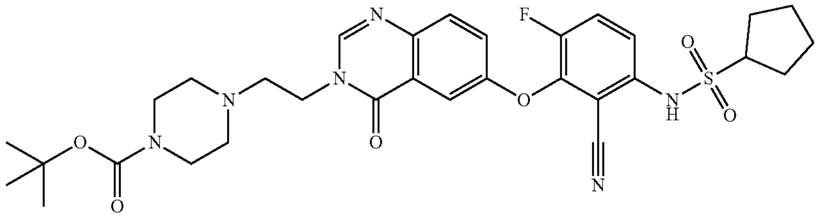

Following the procedure described for Example 2, the title compound was obtained from Intermediate IA12 (75 mg, 147 μmol, Eq: 1.0) and Intermediate IC6 (308 mg, 226 μmol, Eq: 2.1) as an off-white solid after SFC purification (53 mg, 100% purity, 56% yield). MS (ESI) m/z: 641.5 [M+H]+.

Example 26

N-[3-[6-[2-cyano-6-fluoro-3-(pyrrolidin-1-ylsulfonylamino)phenoxy]-4-oxo-quinazolin-3-yl]propyl]-N-methyl-acetamide

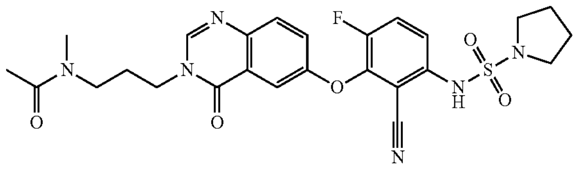 [SMILES: CC(=O)N(C)CCCn1cnc2ccc(Oc3c(F)ccc(NS(=O)(=O)N4CCCC4)c3C#N)cc2c1=O]

Following the procedure described for Example 24, the title compound was obtained from Example 19 as a white foam after SFC purification. MS (ESI) m/z: 543.4 [M+H]+.

Example 27 tert-butyl 4-[2-[6-[2-cyano-3-[[ethyl(methyl)sulfamoyl]amino]-6-fluoro-phenoxy]-4-oxo-quinazolin-3-yl]ethyl]piperazine-1-carboxylate

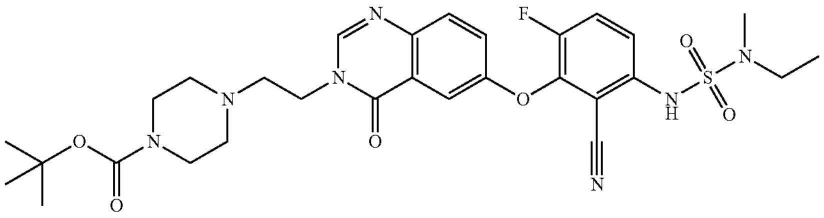 [SMILES: CCN(C)S(=O)(=O)Nc1ccc(F)c(Oc2ccc3ncn(CCN4CCN(C(=O)OC(C)(C)C)CC4)c(=O)c3c2)c1C#N]

Following the procedure described for Example 2, the title compound was obtained from Intermediate IA12 (51.6 mg, 101 μmol, Eq: 1.0) and [methyl(sulfamoyl)amino]ethane (29.3 mg, 212 μmol, Eq: 2.1) as a white foam after SFC purification (22.6 mg, 36% yield). MS (ESI) m/z: 630.5 [M+H]+.

Example 28 tert-butyl N-[[4-[3-[6-[2-cyano-3-(cyclopentylsulfonylamino)-6-fluoro-phenoxy]-4-oxo-quinazolin-3-yl]propyl]phenyl]methyl]-N-methyl-carbamate

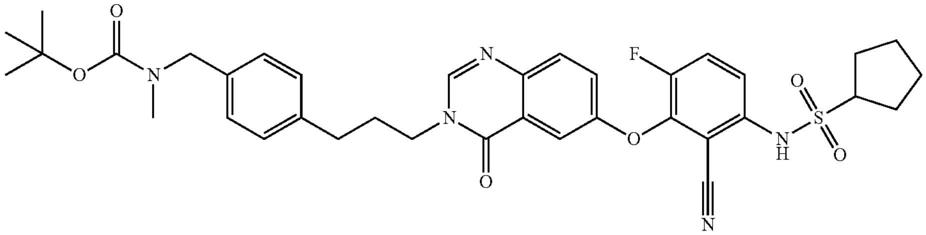 [SMILES: CN(Cc1ccc(CCCn2cnc3ccc(Oc4c(F)ccc(NS(=O)(=O)C5CCCC5)c4C#N)cc3c2=O)cc1)C(=O)OC(C)(C)C]

Following the procedure described for Example 2, the title compound was obtained from Intermediate IA16 (19.7 mg, 35.1 μmol, Eq: 1.0) and Intermediate IC6 (11.5 mg, 77.1 μmol, Eq: 2.1) as a white solid after flash chromatography (0-100% EtOAc in DCM) (1.7 mg, 100% purity, 7% yield). MS (ESI) m/z: 690.6 [M+H]+.

Example 29 tert-butyl 4-[2-[6-[2-cyano-6-fluoro-3-(sec-butylsulfonylamino)phenoxy]-4-oxo-quinazolin-3-yl]ethyl]piperazine-1-carboxylate

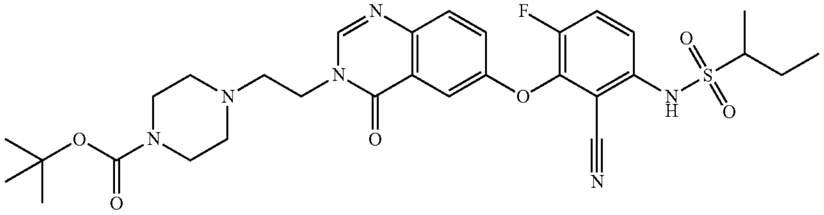 [SMILES: CCC(C)S(=O)(=O)Nc1ccc(F)c(Oc2ccc3ncn(CCN4CCN(C(=O)OC(C)(C)C)CC4)c(=O)c3c2)c1C#N]

Following the procedure described for Example 2, the title compound was obtained from Intermediate IA12 (38.5 mg, 75.2 μmol, Eq: 1.0) and Intermediate IC7 (21.7 mg, 158 μmol, Eq: 2.1) as a off-white foam after flash chromatography (eluent 0-10% MeOH in DCM) (34 mg, 96% purity, 72% yield). MS (ESI) m/z: 629.5 [M+H]+.

Example 30 tert-butyl N-[[4-[3-[6-[2-cyano-6-fluoro-3-(pyrrolidin-1-ylsulfonylamino)phenoxy]-4-oxo-quinazolin-3-yl]propyl]phenyl]methyl]-N-methyl-carbamate

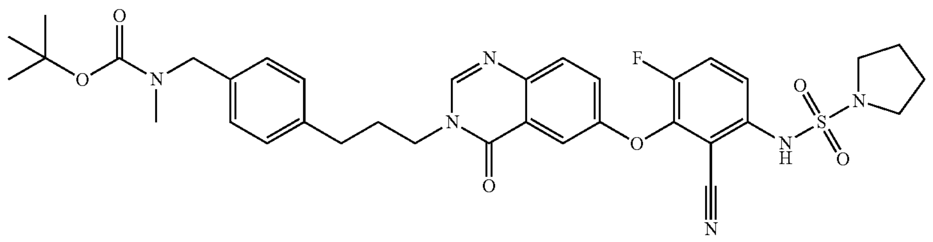 [SMILES: CN(Cc1ccc(CCCn2cnc3ccc(Oc4c(F)ccc(NS(=O)(=O)N5CCCC5)c4C#N)cc3c2=O)cc1)C(=O)OC(C)(C)C]

Following the procedure described for Example 2, the title compound was obtained from Intermediate IA16 (50 mg, 89.2 μmol, Eq: 1.0) and Intermediate IC2 (28.1 mg, 187 μmol, Eq: 2.1) as a white foam after SFC (35.5 mg, 100% purity, 58% yield). MS (ESI) m/z: 629.5 [M+H]+.

Example 31

2-[6-[2-cyano-3-[[ethyl(methyl)sulfamoyl]amino]anilino]-4-oxo-quinazolin-3-yl]-N-(2-methoxyethyl)acetamide

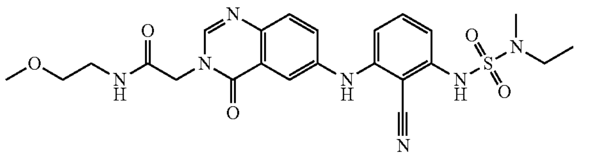 [SMILES: CCN(C)S(=O)(=O)Nc1cccc(Nc2ccc3ncn(CC(=O)NCCOC)c(=O)c3c2)c1C#N]

Intermediate IB5 (15.8 mg, 34.6 μmol, Eq: 1.0) was dissolved in DMF (455 μL), then DIPEA (26.8 mg, 35.6 μL, 208 μmol, Eq: 6.0) was added. At 0° C. HATU (14.5 mg, 38.1 μmol, Eq: 1.1) and 2-methoxyethan-1-amine (8.0 mg, 9.1 μL, 104 μmol, Eq: 3.0) were added and the reaction mixture was stirred at rt overnight. The reaction was concentrated in vacuo. The residue was diluted with DCM and transferred to a column. Purification by flash chromatography (12 g silica, 10% MeOH in DCM) followed by preparative reversed phase HPLC gave the title compound as an off-white solid (5.4 mg, 100% purity, 30% yield). MS (ESI) m/z: 514.3 [M+H]+.

Example 32 tert-butyl 4-[[6-[2-cyano-3-[[ethyl(methyl)sulfamoyl]amino]anilino]-4-oxo-quinazolin-3-yl]methyl]piperidine-1-carboxylate

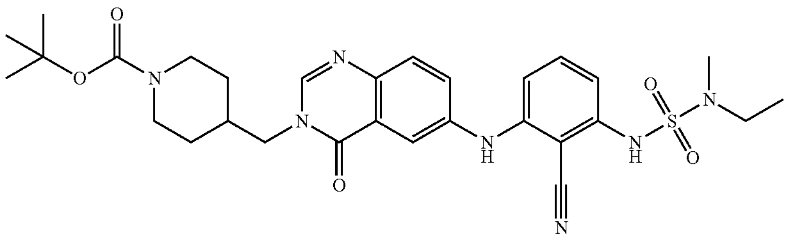 [SMILES: CCN(C)S(=O)(=O)Nc1cccc(Nc2ccc3ncn(CC4CCN(C(=O)OC(C)(C)C)CC4)c(=O)c3c2)c1C#N]

Under argon in a microwave vial, Intermediate IB6 (94 mg, 223 μmol, Eq: 1.0) and Intermediate IB1 (56.6 mg, 223 μmol, Eq: 1.0) were dissolved in dioxane (6 mL) then Cs2CO3 (220 mg, 668 μmol Eq: 3.0) was added. The reaction mixture was flushed with argon, then BippyPhos (6.97 mg, 13.4 μmol, Eq: 0.06) and tris(dibenzylideneacetone)dipalladium (0) chloroform adduct (7.05 mg, 6.68 μmol, Eq: 0.03) were added. The reaction was flushed with argon again, and the vial was closed. The reaction mixture was stirred at 110° C. for 2.5 h. The reaction mixture was taken up in EtOAc and ice, washed 1× with water and 2× with 2 M aq. NaOH. The aqueous layer was back-extracted 2× with EtOAc. The organic layers were combined, washed with brine, dried over Na2SO4 and concentrated in vacuo. The residue was diluted with EtOAc and transferred to a column. Purification by flash chromatography (40 g silica, 0-100% EtOAc in heptane) gave the title compound as an off-white foam (76 mg, 90% purity, 51% yield). MS (ESI) m/z: 494.4 [M+H]+.

Example 33

3-[(1-acetyl-4-piperidyl)methyl]-6-[2-cyano-3-[[ethyl(methyl)sulfamoyl]amino]anilino]-4-oxo-quinazoline

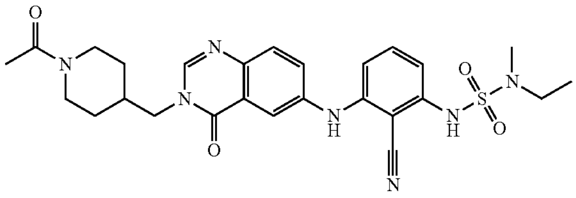 [SMILES: CCN(C)S(=O)(=O)Nc1cccc(Nc2ccc3ncn(CC4CCN(C(C)=O)CC4)c(=O)c3c2)c1C#N]

Step 1: 6-[2-cyano-3-[[ethyl(methyl)sulfamoyl]amino]anilino]-4-oxo-3-(4-piperidylmethyl)quinazoline hydrochloride

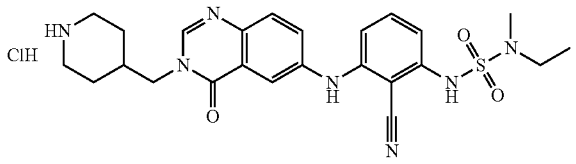 [SMILES: Cl ; CCN(C)S(=O)(=O)Nc1cccc(Nc2ccc3ncn(CC4CCNCC4)c(=O)c3c2)c1C#N]

Example 32 (17.9 mg, 30 μmol, Eq: 1.0) was dissolved in DCM (100 μL). At rt, HCl (4 M in dioxane, 37.6 μL, 150 μmol, Eq: 5.0) was added, followed by additional DCM (200 μL). The reaction mixture was stirred at rt for 20 h 15 min, then additional DCM (200 μL) and HCl (4 M in dioxane, 37.6 μL, 150 μmol, Eq: 5.0) was added. After 4.5 h, the reaction mixture was concentrated in vacuo to give the title compound as an off-white solid (18 mg, 90% purity, 100% yield). MS (ESI) m/z: 494.3 [M−H]−.

Step 2: 3-[(1-acetyl-4-piperidyl)methyl]-6-[2-cyano-3-[[ethyl(methyl)sulfamoyl]amino]anilino]-4-oxo-quinazoline

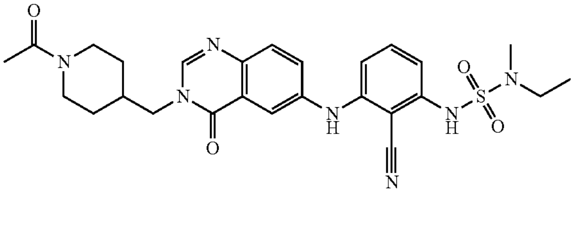 [SMILES: CCN(C)S(=O)(=O)Nc1cccc(Nc2ccc3ncn(CC4CCN(C(C)=O)CC4)c(=O)c3c2)c1C#N]

DIPEA (19.8 mg, 26.2 μL, 150 μmol, Eq: 5.0) was added to a stirred suspension of 6-[2-cyano-3-[[ethyl(methyl)sulfamoyl]amino]anilino]-4-oxo-3-(4-piperidylmethyl)quinazoline hydrochloride (16 mg, 30.1 μmol, Eq: 1.0) in DMF (800 μL). The reaction mixture was cooled to 0° C. and acetic anhydride (4.45 mg, 4.12 μL, 43.6 μmol, Eq: 1.45) was added. The reaction mixture was stirred for 40 min at 0° C. and then allowed to warm to rt. After 1 h 15 min, the reaction was concentrated in vacuo. The residue was diluted with DCM, evaporated with silica gel to dryness and transferred to a column. Purification by flash chromatography (Isco CombiFlash Companion, SILICYCLE FLH-R10017B-ISO40 Silia Sep TM, HP 40 g, with 0% to 9.2% MeOH in DCM) gave the title compound as a white foam (8.2 mg, 100% purity, 51% yield). MS (ESI) m/z: 536.3 [M+H]+.

Example 34 tert-butyl N-[2-[2-[2-[6-[2-cyano-3-[[ethyl(methyl)sulfamoyl]amino]anilino]-4-oxo-quinazolin-3-yl]ethoxy]ethoxy]ethyl]carbamate

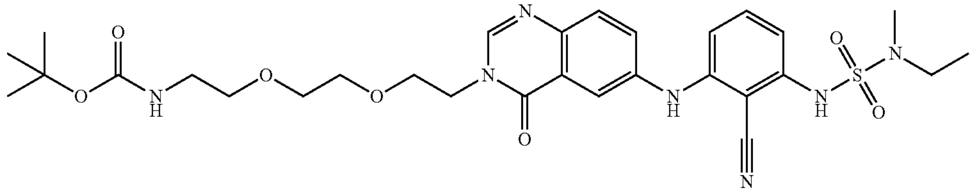 [SMILES: CCN(C)S(=O)(=O)Nc1cccc(Nc2ccc3ncn(CCOCCOCCNC(=O)OC(C)(C)C)c(=O)c3c2)c1C#N]

Following the procedure described for Example 32, the title compound was obtained from Intermediate IB7 (35 mg, 76.7 μmol, Eq: 1.0) and Intermediate D31 (19.5 mg, 76.7 μmol, Eq: 1.0) as a white foam after preparative reversed phase HPLC purification (18 mg, 100% purity, 37% yield). MS (ESI) m/z: 630.5 [M+H]+.

Example 35 tert-butyl 4-[6-[2-cyano-3-[[(3R)-3-fluoropyrrolidin-1-yl]sulfonylamino]anilino]-4-oxo-quinazolin-3-yl] butanoate

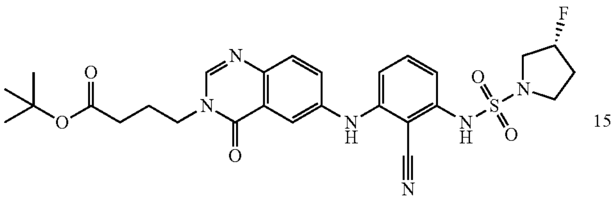

Following the procedure described for Example 32, the title compound was obtained from Intermediate IB8 (200 mg, 545 μmol, Eq: 1.0) and Intermediate IB2 (163 mg, 572 μmol, Eq: 1.05) as a light yellow foam after flash chromatography (0-90% EtOAc in heptane) (234 mg, 95% purity, 72% yield). MS (ESI) m/z: 571.3 [M+H]+.

Example 36

(3R)—N-[3-[[3-(2-benzyloxyethyl)-4-oxo-quinazolin-6-yl]amino]-2-cyano-phenyl]-3-fluoro-pyrrolidine-1-sulfonamide

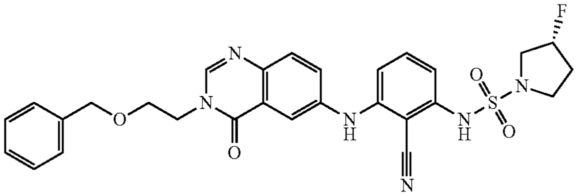 [SMILES: N#Cc1c(Nc2ccc3ncn(CCOCc4ccccc4)c(=O)c3c2)cccc1NS(=O)(=O)N1CC[C@@H](F)C1]

Following the procedure described for Example 32, the title compound was obtained from Intermediate IB9 (30 mg, 84 μmol, Eq: 1.0) and Intermediate IB2 (25 mg, 88 μmol, Eq: 1.05) as an off-white foam after flash chromatography (0-90% EtOAc in DCM) (26 mg, 98% purity, 55% yield). MS (ESI) m/z: 563.3 [M+H]+.

Example 37 tert-butyl 4-[2-[6-[2-cyano-3-[[(3R)-3-fluoropyrrolidin-1-yl]sulfonylamino]anilino]-4-oxo-quinazolin-3-yl]ethyl]piperidine-1-carboxylate

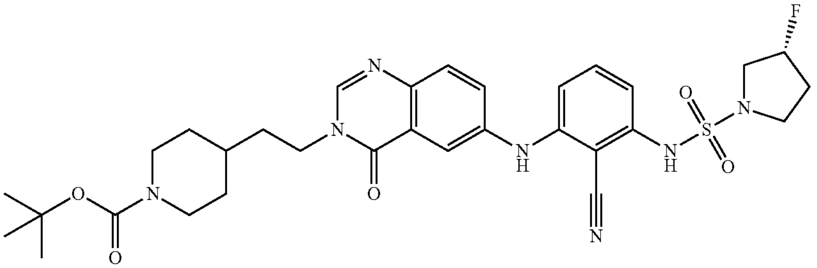 [SMILES: CC(C)(C)OC(=O)N1CCC(CCn2cnc3ccc(Nc4cccc(NS(=O)(=O)N5CC[C@@H](F)C5)c4C#N)cc3c2=O)CC1]

Following the procedure described for Example 32, the title compound was obtained from Intermediate D310 (30 mg, 69 μmol, Eq: 1.0) and Intermediate IB2 (20.5 mg, 72.2 μmol, Eq: 1.05) as an off-white foam after flash chromatography (0-100% EtOAc in DCM) (26 mg, 100% purity, 59% yield). MS (ESI) m/z: 638.4 [M−H]−.

Example 38

3-[2-[2-(2-aminoethoxy)ethoxy]ethyl]-6-[2-cyano-3-[[ethyl(methyl)sulfamoyl]amino]anilino]-4-oxo-quinazoline hydrochloride

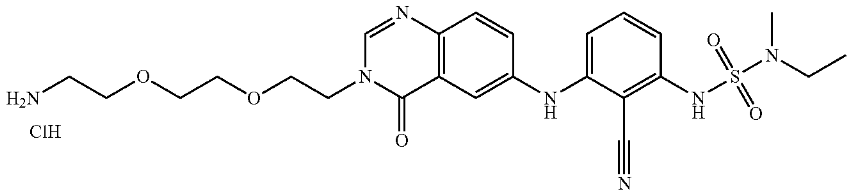 [SMILES: CCN(C)S(=O)(=O)Nc1cccc(Nc2ccc3ncn(CCOCCOCCN)c(=O)c3c2)c1C#N ; Cl]

Example 34 (13.3 mg, 21.1 μmol, Eq: 1.0) was dissolved in dioxane (200 μL). At rt, HCl (4 M in dioxane, 26.4 μL, 106 μmol, Eq: 5.0) was added. The reaction mixture was stirred at rt for 141.5 h, then concentrated in vacuo to give the title compound as a light yellow solid (12 mg, 100% purity, 100% yield). MS (ESI) m/z: 528.3 [M−H]−.

Example 39

4-[6-[2-cyano-3-[[(3R)-3-fluoropyrrolidin-1-yl]sulfonylamino]anilino]-4-oxo-quinazolin-3-yl]butanoic acid

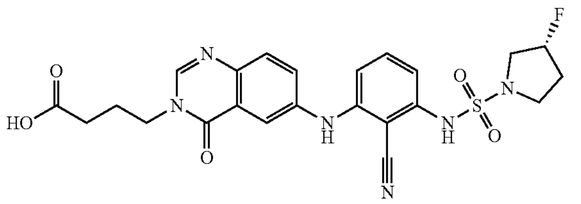 [SMILES: N#Cc1c(Nc2ccc3ncn(CCCC(=O)O)c(=O)c3c2)cccc1NS(=O)(=O)N1CC[C@@H](F)C1]

Example 35 (226 mg, 376 μmol, Eq: 1.0) was suspended in DCM (6 mL) and then trifluoroacetic acid (1.35 g, 910 μL, 11.9 mmol, Eq: 31.6) was added at rt. The reaction mixture was stirred at rt for 17 h, then concentrated in vacuo to give the title compound as a light yellow solid (258 mg, 90% purity, 98% yield). MS (ESI) m/z: 515.2 [M+H]+.

Example 40 tert-butyl 4-[4-[6-[2-cyano-3-[[(3R)-3-fluoropyrrolidin-1-yl]sulfonylamino]anilino]-4-oxo-quinazolin-3-yl]butanoyl]piperazine-1-carboxylate

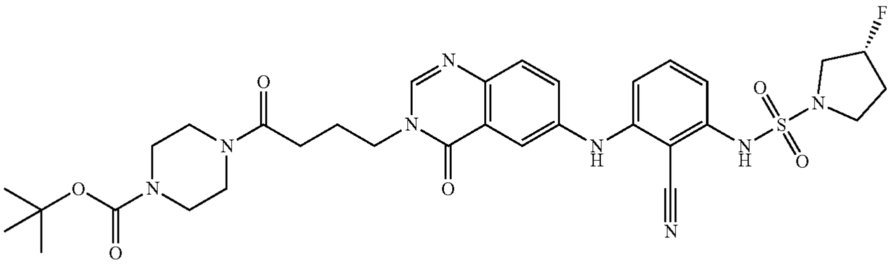 [SMILES: CC(C)(C)OC(=O)N1CCN(C(=O)CCCn2cnc3ccc(Nc4cccc(NS(=O)(=O)N5CC[C@@H](F)C5)c4C#N)cc3c2=O)CC1]

To a stirred solution of Example 39 (30 mg, 43 μmol, Eq: 1.0) in EtOAc (700 μL) at rt was added 4-methylmorpholine (47.8 mg, 52 μL, 473 μmol, Eq: 11) and tert-butyl piperazine-1-carboxylate (8 mg, 43 μmol, Eq: 1.0). The reaction mixture was stirred at rt for 10 min, then n-propylphosphonic acid anhydride (T3P, 54.7 mg, 51.1 μL, 85.9 μmol, Eq: 2.0) was added. The reaction mixture was stirred at rt for 5 h 38 min, then diluted with EtOAc and 5 mL water. The phases were separated, and the aqueous phase was extracted 2× with further EtOAc. The combined organic phases were washed with 5 mL brine, dried, filtered and concentrated in vacuo. The residue was diluted with DCM and transferred to a column. Purification by flash chromatography (40 g silica, 0-11.5% MeOH in DCM) gave the title compound as an off-white solid (19 mg, 100% purity, 65% yield). MS (ESI) m/z: 681.5 [M−H]−.

Example 41 tert-butyl 4-[4-[6-[2-cyano-3-[[(3R)-3-fluoropyrrolidin-1-yl]sulfonylamino]anilino]-4-oxo-quinazolin-3-yl]butanoylamino]piperidine-1-carboxylate)

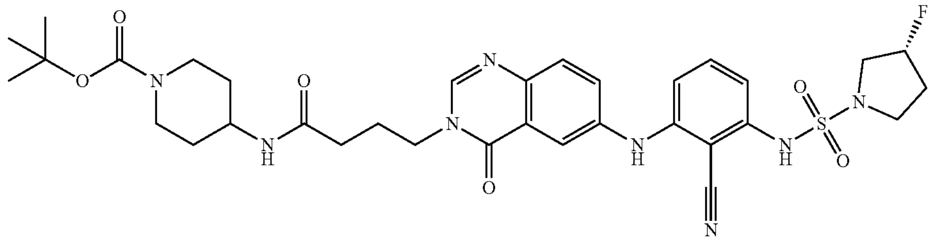 [SMILES: CC(C)(C)OC(=O)N1CCC(NC(=O)CCCn2cnc3ccc(Nc4cccc(NS(=O)(=O)N5CC[C@@H](F)C5)c4C#N)cc3c2=O)CC1]

To a stirred solution of Example 39 (30 mg, 43 μmol, Eq: 1.0) in EtOAc (700 μL) was added 4-methylmorpholine (47.8 mg, 52 μL, 473 μmol, Eq: 11) and tert-butyl 4-aminopiperidine-1-carboxylate (9.46 mg, 47.3 μcool, Eq: 1.1). The reaction mixture was stirred at rt for 10 min, then n-propylphosphonic acid anhydride (T3P, 54.7 mg, 51.1 μL, 85.9 μmol, Eq: 2.0) was added. The reaction mixture was stirred at rt for 15 h 40 min, then DMF (700 μL) and HATU (16.3 mg, 43 μmol, Eq: 1.0) were added. The reaction mixture was stirred at rt for 30 min, then concentrated in vacuo. The residue was diluted with EtOAc and 5 mL water. The phases were separated, and the aqueous phase was extracted 2× with EtOAc. The combined organic phases were washed with 5 mL brine, dried, filtered and concentrated in vacuo. The residue was diluted with DCM and transferred to a column. Purification by flash chromatography (40 g silica, 0-8% MeOH in DCM) gave the title compound as a white solid (19 mg, 100% purity, 64% yield). MS (ESI) m/z: 695.5 [M−H]−.

Example 42 tert-butyl 4-[6-[2-cyano-3-[[cyclopropyl(methyl) sulfamoyl]amino]anilino]-4-oxo-quinazolin-3-yl] butanoate

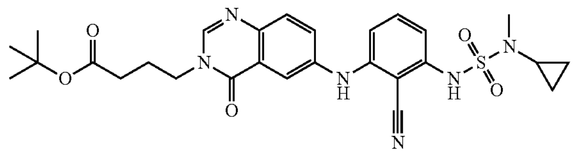 [SMILES: CN(C1CC1)S(=O)(=O)Nc1cccc(Nc2ccc3ncn(CCCC(=O)OC(C)(C)C)c(=O)c3c2)c1C#N]

Following the procedure described for Example 32, the title compound was obtained from Intermediate IB8 (30 mg, 82 μmol, Eq: 1.0) and Intermediate IB3 (22.8 mg, 85.8 μmol, Eq: 1.05) as a light yellow foam after flash chromatography (0-90% EtOAc in DCM) (13.5 mg, 30% yield). MS (ESI) m/z: 553.3 [M+H]+.

Example 43 tert-butyl N-[3-[6-[2-cyano-3-[[(3R)-3-fluoropyrrolidin-1-yl]sulfonylamino]anilino]-4-oxo-quinazolin-3-yl]propyl]carbamate

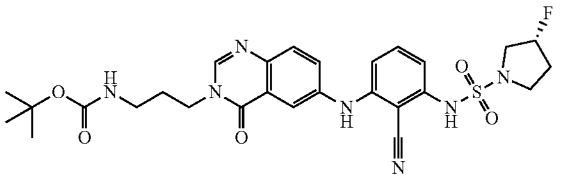 [SMILES: CC(C)(C)OC(=O)NCCCn1cnc2ccc(Nc3cccc(NS(=O)(=O)N4CC[C@@H](F)C4)c3C#N)cc2c1=O]

Following the procedure described for Example 32, the title compound was obtained from Intermediate D311 (30 mg, 78.5 μmol, Eq: 1.0) and Intermediate IB2 (23.4 mg, 82.4 μmol, Eq: 1.05) as a light yellow solid after flash chromatography (0-65% EtOAc in DCM) (30 mg, 100% purity, 65% yield). MS (ESI) m/z: 584.2 [M−H]−.

Example 44

(3R)—N-[2-cyano-3-[[4-oxo-3-(3-phenylpropyl) quinazolin-6-yl]amino]phenyl]-3-fluoro-pyrrolidine-1-sulfonamide

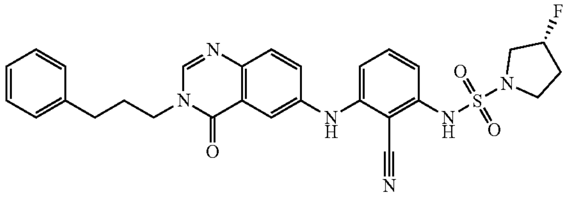 [SMILES: N#Cc1c(Nc2ccc3ncn(CCCc4ccccc4)c(=O)c3c2)cccc1NS(=O)(=O)N1CC[C@@H](F)C1]

Following the procedure described for Example 32, the title compound was obtained from Intermediate IB12 (40 mg, 117 μmol, Eq: 1.0) and Intermediate IB2 (34.8 mg, 122 μmol, Eq: 1.05) as a light yellow foam after flash chromatography (0-100% EtOAc in heptane) (35 mg, 100% purity, 55% yield). MS (ESI) m/z: 547.3 [M+H]+.

Example 45 tert-butyl N-[2-[4-[6-[2-cyano-3-[[(3R)-3-fluoropyrrolidin-1-yl]sulfonylamino]anilino]-4-oxo-quinazolin-3-yl]butanoylamino]ethyl]-N-methyl-carbamate

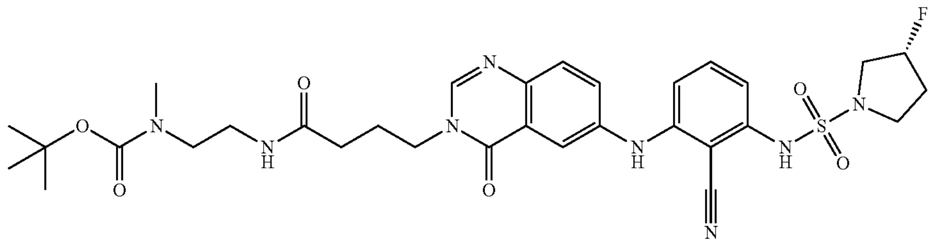 [SMILES: CN(CCNC(=O)CCCn1cnc2ccc(Nc3cccc(NS(=O)(=O)N4CC[C@@H](F)C4)c3C#N)cc2c1=O)C(=O)OC(C)(C)C]

Example 39 (40 mg, 63.6 μmol, Eq: 1.0) was dissolved in DMF (2 mL), then DIPEA (24.7 mg, 33.3 μL, 191 μmol, Eq: 3.0) was added. At 0° C., HATU (26.6 mg, 70 μmol, Eq: 1.1) was added. After 15 min tert-butyl N-(2-aminoethyl)-N-methyl-carbamate (16.6 mg, 17.1 μL, 95.5 μmol, Eq: 1.5) was added and the reaction mixture was stirred overnight at rt. After 16 h, the reaction mixture was concentrated in vacuo. The residue was diluted with DCM and transferred to a column. Purification by flash chromatography (40 g silica, 0-11.5% MeOH in DCM) gave the title compound as a white foam (29 mg, 99% purity, 68% yield). MS (ESI) m/z: 669.5 [M−H]−.

Example 46 tert-butyl 4-[2-[6-[2-cyano-3-(pyrrolidin-1-ylsulfonylamino)anilino]-4-oxo-quinazolin-3-yl]ethyl]piperidine-1-carboxylate

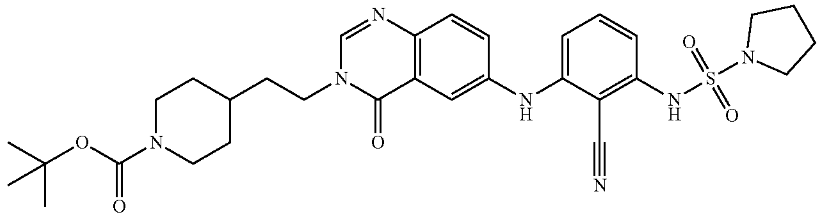 [SMILES: CC(C)(C)OC(=O)N1CCC(CCn2cnc3ccc(Nc4cccc(NS(=O)(=O)N5CCCC5)c4C#N)cc3c2=O)CC1]

Following the procedure described for Example 32, the title compound was obtained from Intermediate D310 (30 mg, 68.8 μmol, Eq: 1.0) and Intermediate IB4 (19.2 mg, 72.2 μmol, Eq: 1.05) as a light yellow foam after flash chromatography (0-100% EtOAc in heptane) (18.5 mg, 100% purity, 43% yield). MS (ESI) m/z: 620.5 [M+H]+.

Example 47

Materials

Cell Lines

A375 is a cellular cancer model expressing V600E mutated BRAF and HCT116 a cellular cancer model expressing WT BRAF. First generation BRAF inhibitors such as e.g. dabrafenib induce a paradox effect on tumour cells in that they inhibit the growth of V600E mutated BRAF cells (such as e.g. A375), while they activate growth in WT BRAF cells (such as e.g. HCT 116). ERK 1,2 phosphorylation (terminal member of the phosphorylation cascade of the MAPK pathway) is hereafter reported as main readout for the activation status of the MAPK pathway. DMEM no-phenol red medium supplemented with L-glutamine was purchased from (Thermo Fisher Scientific). Fetal bovine serum (FBS) was purchased from VWR. Advanced ERK phospho-T202/Y204 kit—10,000 tests was purchased from Cisbio cat #64AERPEH. A375 (catalog #CRL-1619) and HCT116 (catalog #CCL-247) cells were originally obtained from American type Culture Collection (ATCC) and banked by the Roche repository. 384-Well microplates utilized were purchased from Greiner Bio-One, 384-well, (With Lid, HiBase, Low volume cat 784-080).

HTRF Assay for P-ERK Determination in A375 or HCT116 Cells

Prior to the assay, A375 and HCT116 cell lines are maintained in DMEM no-phenol red medium supplemented with 10% fetal bovine serum (FBS). Following compound treatment, P-ERK levels are determined by measuring FRET fluorescence signal induced by selective binding of 2 antibodies provided in the mentioned kit (Cisbio cat #64AERPEH) on ERK protein when phosphorylated at Thr202/Tyr204. Briefly, 8000 cells/well in 12 μl media/well are plated in the 384-well plate and left overnight in the incubator (at 37° C. with 5% CO2-humidified atmosphere), the following day the plate is treated in duplicate with test compounds, dabrafenib and PLX8394 (the latter two as controls) at the following final drug concentrations: 10 μM-3 μM 1 μM-0.3 μM-0.1 μM-0.03 μM-0, 01 μM-0.003 μM-0.001 μM, all wells are subjected to DMSO normalization and drug incubation occurs for 1 hour. Then, 4111 of a 4× lysis buffer supplied with the kit are added to the wells, the plate is then centrifuged for 30 second (3000 rpm) and incubated on a plate shaker for 1 h at rt.

At the end of the incubation 4 μL/well of advanced P-ERK antibody solution (prepared according to manufacturer's instruction) followed by 4 μL/well of criptate P-ERK antibody solution (prepared according to manufacturer's instruction) (Cisbio cat #64AERPEH) are added to test wells.

In order to allow proper data normalization control wells non drug treated reported in the following table are always included in each plate (according to manufacturer's instruction):

p-ERK HTRF well compositions (μl):

| neg ctrl | pos ctrl | neut ctrl | cpd | blank | |
|---|---|---|---|---|---|
| — | — | 12 | 12 | 12 | Cells |
| 12 | — | — | — | — | Media |
| — | — | — | <0.05 | — | Cpd |
| — | 16 | — | — | — | control lysate (ready-to-use) |
| 4 | — | 4 | 4 | 4 | 4x lysis buffer |
| 4 | 4 | 4 | 4 | — | Advanced p-ERK antibody solution |
| — | — | — | — | 4 | Advanced p-ERK1/2 Cryptate antibody solut. |
| 20 | 20 | 20 | 20 | 20 | Total volume in Well |

The plate is then centrifuged at 3000 rpm for 30 second, sealed to prevent evaporation and incubated overnight in the dark at room temperature.

The plate is then analyzed and fluorescence emission value collected through a Pherastast FSX (BMG Labtech) apparatus at 665 and 620 nM.

The obtained fluorescence values are processed according to the formula Ratio=Signal(620 nm)/Signal(625 nm)*10000 then the average of the ratio on the blank is subtracted to all values.

Data are normalized in the case of A375 cells (BRAF inhibition) considering the average of the ratio (blank subtracted) derived by DMSO only treated cells as 100% and by considering the average of the ratio (blank subtracted) derived by 10 μM Dabrafenib treated cells as 0%. Mean of the normalized points are fitted with sigmoidal curve and IC50 determined.

Data are normalized in the case of HCT116 cells (BRAF activation) considering the average of the ratio (blank subtracted) derived by DMSO only treated cells as 0% and by considering the average of the ratio (blank subtracted) derived by Dabrafenib treated cells at the concentration which provides the highest signal as 100%. Individual points are fitted with either sigmoidal or bell shape curves. The EC50 is the concentration at which activation equal to 50% of the maximum activation achieved by Dabrafenib is obtained. The results are shown below in Table 1.

TABLE 1

| Example | Chemical Name | KD [BRAF (V600E)] (μM) | KD [BRAF (wt)] (μM) | IC50 (A375) (μM) | EC50 (HCT-116) (μM) |
|---|---|---|---|---|---|
| 1 | tert-butyl 4-[6-[2-cyano-3-[[ethyl(methyl)sulfamoyl]amino]-6-fluoro-phenoxy]-4-oxo-quinazolin-3-yl]butanoate | 0.02671 | 0.01529 | 0.01979 | 2.35586 |
| 2 | tert-butyl 4-[2-[6-[2-cyano-6-fluoro-3-[[(3R)-3-fluoropyrrolidin-1-yl]sulfonylamino]phenoxy]-4-oxo-quinazolin-3-yl]ethyl]piperidine-1-carboxylate | 0.02142 | 0.01893 | 0.03030 | 2.24525 |
| 3 | tert-butyl 4-[2-[6-[2-cyano-3-[[ethyl(methyl)sulfamoyl]amino]-6-fluoro-phenoxy]-4-oxo-quinazolin-3-yl]ethyl]piperidine-1-carboxylate | 0.16202 | 0.07826 | 0.04100 | 6.39887 |
| 4 | tert-butyl N-[3-[6-[2-cyano-6-fluoro-3-[[(3R)-3-fluoropyrrolidin-1-yl]sulfonylamino]phenoxy]-4-oxo-quinazolin-3-yl]propyl]carbamate | 0.00275 | 0.00109 | 0.07350 | 7.08236 |
| 5 | tert-butyl N-[3-[6-[2-cyano-6-fluoro-3-(pyrrolidin-1-ylsulfonylamino)phenoxy]-4-oxo-quinazolin-3-yl]propyl]carbamate | 0.00282 | 0.00135 | 0.01810 | 1.19140 |
| 6 | tert-butyl N-[3-[6-[2-cyano-3-[[ethyl(methyl)sulfamoyl]amino]-6-fluoro-phenoxy]-4-oxo-quinazolin-3-yl]propyl]carbamate | 0.01938 | 0.00636 | 0.04158 | ≥10.000 |
| 7 | tert-butyl 4-[2-[6-[2-cyano-6-fluoro-3-(pyrrolidin-1-ylsulfonylamino)phenoxy]-4-oxo-quinazolin-3-yl]ethyl]piperidine-1-carboxylate | 0.02083 | 0.01223 | 0.05199 | 2.10334 |
| 8 | tert-butyl N-[3-[6-[2-cyano-3-(cyclopentylsulfonylamino)-6-fluoro-phenoxy]-4-oxo-quinazolin-3-yl]propyl]carbamate | 0.00783 | 0.00486 | 0.03388 | 2.42962 |

TABLE 1-continued

| Example | Chemical Name | KD [BRAF (V600E)] (μM) | KD [BRAF (wt)] (μM) | IC50 (A375) (μM) | EC50 (HCT-116) (μM) |
|---|---|---|---|---|---|
| 9 | tert-butyl N-[3-[6-[3-(azetidin-1-ylsulfonylamino)-2-cyano-6-fluoro-phenoxy]-4-oxo-quinazolin-3-yl]propyl]carbamate | 0.00097 | 0.00069 | 0.02892 | 0.62364 |
| 10 | tert-butyl 4-[2-[6-[2-cyano-6-fluoro-3-[[(3R)-3-fluoropyrrolidin-1-yl]sulfonylamino]phenoxy]-4-oxo-quinazolin-3-yl]ethyl]piperazine-1-carboxylate | 0.00482 | 0.00351 | 0.03671 | 1.53111 |
| 11 | N-[2-cyano-4-fluoro-3-[4-oxo-3-(3-phenylpropyl)quinazolin-6-yl]oxy-phenyl]cyclopentanesulfonamide | 0.05051 | 0.02438 | 0.05249 | 0.90783 |
| 12 | tert-butyl N-[3-[6-[2-cyano-3-(cyclohexylsulfonylamino)-6-fluoro-phenoxy]-4-oxo-quinazolin-3-yl]propyl]carbamate | 0.05923 | 0.02755 | 0.05590 | 4.92909 |
| 13 | tert-butyl N-[3-[6-[2-cyano-6-fluoro-3-(sec-butylsulfonylamino)phenoxy]-4-oxo-quinazolin-3-yl]propyl]carbamate | 0.01929 | 0.01207 | 0.03630 | 2.82105 |
| 14 | tert-butyl 4-[2-[6-[2-cyano-3-(cyclohexylsulfonylamino)-6-fluoro-phenoxy]-4-oxo-quinazolin-3-yl]ethyl]piperidine-1-carboxylate | 0.11420 | 0.05428 | 0.25423 | 4.84568 |
| 15 | tert-butyl 4-[2-[6-[2-cyano-6-fluoro-3-(sec-butylsulfonylamino)phenoxy]-4-oxo-quinazolin-3-yl]ethyl]piperidine-1-carboxylate | 0.09352 | 0.05043 | 0.07886 | 4.03883 |
| 16 | tert-butyl 4-[2-[6-[2-cyano-6-fluoro-3-(pyrrolidin-1-ylsulfonylamino)phenoxy]-4-oxo-quinazolin-3-yl]ethyl]piperazine-1-carboxylate | 0.00216 | 0.00161 | 0.01101 | 0.24034 |
| 17 | tert-butyl 4-[2-[6-[2-cyano-3-(cyclopentylsulfonylamino)-6-fluoro-phenoxy]-4-oxo-quinazolin-3-yl]ethyl]piperidine-1-carboxylate | 0.02462 | 0.01234 | 0.05710 | 1.14376 |
| 18 | tert-butyl 4-[2-[6-[2-cyano-6-fluoro-3-(1-piperidylsulfonylamino)phenoxy]-4-oxo-quinazolin-3-yl]ethyl]piperidine-1-carboxylate | 0.05747 | 0.04543 | 0.15805 | 1.45534 |
| 19 | tert-butyl N-[3-[6-[2-cyano-6-fluoro-3-(pyrrolidin-1-ylsulfonylamino)phenoxy]-4-oxo-quinazolin-3-yl]propyl]-N-methyl-carbamate | 0.00231 | 0.00093 | 0.10304 | ≥10.000 |
| 20 | tert-butyl N-[3-[6-[2-cyano-3-(cyclopentylsulfonylamino)-6-fluoro-phenoxy]-4-oxo-quinazolin-3-yl]propyl]-N-methyl-carbamate | 0.00920 | 0.00334 | 0.43600 | ≥10.000 |
| 21 | tert-butyl 4-[2-[6-[2-cyano-3-(cyclobutylsulfonylamino)-6-fluoro-phenoxy]-4-oxo-quinazolin-3-yl]ethyl]piperidine-1-carboxylate | 0.06717 | 0.01167 | 0.08685 | ≥10.000 |

TABLE 1-continued

| Example | Chemical Name | KD [BRAF (V600E)] (μM) | KD [BRAF (wt)] (μM) | IC50 (A375) (μM) | EC50 (HCT-116) (μM) |
|---|---|---|---|---|---|
| 22 | tert-butyl 3-[2-[6-[2-cyano-3-(cyclopentylsulfonylamino)-6-fluoro-phenoxy]-4-oxo-quinazolin-3-yl]ethyl]piperidine-1-carboxylate | 0.02889 | 0.02788 | 0.15488 | ≥10.000 |
| 23 | tert-butyl 3-[2-[6-[2-cyano-6-fluoro-3-(pyrrolidin-1-ylsulfonylamino)phenoxy]-4-oxo-quinazolin-3-yl]ethyl]piperidine-1-carboxylate | 0.01020 | 0.00923 | 0.04974 | 2.29858 |
| 24 | N-[3-[6-[2-cyano-3-(cyclopentylsulfonylamino)-6-fluoro-phenoxy]-4-oxo-quinazolin-3-yl]propyl]-N-methyl-acetamide | 0.00076 | 0.00042 | 0.05040 | ≥10.0000 |
| 25 | tert-butyl 4-[2-[6-[2-cyano-3-(cyclopentylsulfonylamino)-6-fluoro-phenoxy]-4-oxo-quinazolin-3-yl]ethyl]piperazine-1-carboxylate | 0.00706 | 0.00414 | 0.00763 | 0.80193 |
| 26 | N-[3-[6-[2-cyano-6-fluoro-3-(pyrrolidin-1-ylsulfonylamino)phenoxy]-4-oxo-quinazolin-3-yl]propyl]-N-methyl-acetamide | 0.00055 | 0.00032 | 0.02053 | 4.25631 |
| 27 | tert-butyl 4-[2-[6-[2-cyano-3-[[ethyl(methyl)sulfamoyl]amino]-6-fluoro-phenoxy]-4-oxo-quinazolin-3-yl]ethyl]piperazine-1-carboxylate | 0.02841 | 0.01632 | 0.00699 | 6.85533 |
| 28 | tert-butyl N-[[4-[3-[6-[2-cyano-3-(cyclopentylsulfonylamino)-6-fluoro-phenoxy]-4-oxo-quinazolin-3-yl]propyl]phenyl]methyl]-N-methyl-carbamate | 0.03373 | 0.01957 | 0.14401 | 0.83583 |
| 29 | tert-butyl 4-[2-[6-[2-cyano-6-fluoro-3-(sec-butylsulfonylamino)phenoxy]-4-oxo-quinazolin-3-yl]ethyl]piperazine-1-carboxylate | 0.01919 | 0.00743 | 0.01810 | 3.66951 |
| 30 | tert-butyl N-[[4-[3-[6-[2-cyano-6-fluoro-3-(pyrrolidin-1-ylsulfonylamino)phenoxy]-4-oxo-quinazolin-3-yl]propyl]phenyl]methyl]-N-methyl-carbamate | 0.01215 | 0.00615 | 0.05245 | 0.45531 |
| 31 | 2-[6-[2-cyano-3-[[ethyl(methyl)sulfamoyl]amino]anilino]-4-oxo-quinazolin-3-yl]-N-(2-methoxyethyl)acetamide | 0.40302 | 0.13681 | ≥10.000 | ≥10.000 |
| 32 | tert-butyl 4-[[6-[2-cyano-3-[[ethyl(methyl)sulfamoyl]amino]anilino]-4-oxo-quinazolin-3-yl]methyl]piperidine-1-carboxylate | 0.81285 | 0.21007 | 0.42767 | ≥10.000 |
| 33 | 3-[(1-acetyl-4-piperidyl)methyl]-6-[2-cyano-3-[[ethyl(methyl)sulfamoyl]amino]anilino]-4-oxo-quinazoline | 0.09288 | 0.04562 | 0.57635 | ≥10.000 |
| 34 | tert-butyl N-[2-[2-[2-[6-[2-cyano-3-[[ethyl(methyl)sulfamoyl]amino]anilino]-4-oxo-quinazolin-3-yl]ethoxy]ethoxy]ethyl]carbamate | 0.24697 | 0.09193 | 0.28674 | ≥10.000 |

TABLE 1-continued

| Example | Chemical Name | KD [BRAF (V600E)] (μM) | KD [BRAF (wt)] (μM) | IC50 (A375) (μM) | EC50 (HCT-116) (μM) |
|---|---|---|---|---|---|
| 35 | tert-butyl 4-[6-[2-cyano-3-[[(3R)-3-fluoropyrrolidin-1-yl]sulfonylamino]anilino]-4-oxo-quinazolin-3-yl]butanoate | 0.02094 | 0.00792 | 0.01291 | 7.21795 |
| 36 | (3R)-N-[3-[[3-(2-benzyloxyethyl)-4-oxo-quinazolin-6-yl]amino]-2-cyano-phenyl]-3-fluoro-pyrrolidine-1-sulfonamide | 0.27258 | 0.13057 | 0.11433 | ≥10.000 |
| 37 | tert-butyl 4-[2-[6-[2-cyano-3-[[(3R)-3-fluoropyrrolidin-1-yl]sulfonylamino]anilino]-4-oxo-quinazolin-3-yl]ethyl]piperidine-1-carboxylate | 0.04366 | 0.02083 | 0.08063 | 4.46583 |
| 38 | 3-[2-[2-(2-aminoethoxy)ethoxy]ethyl]-6-[2-cyano-3-[[ethyl(methyl)sulfamoyl]amino]anilino]-4-oxo-quinazoline | 0.44300 | 0.17395 | 5.73972 | ≥10.000 |
| 39 | 4-[6-[2-cyano-3-[[(3R)-3-fluoropyrrolidin-1-yl]sulfonylamino]anilino]-4-oxo-quinazolin-3-yl]butanoic acid | 0.04829 | 0.01158 | ≥10.000 | ≥10.000 |
| 40 | tert-butyl 4-[4-[6-[2-cyano-3-[[(3R)-3-fluoropyrrolidin-1-yl]sulfonylamino]anilino]-4-oxo-quinazolin-3-yl]butanoyl]piperazine-1-carboxylate | 0.00788 | 0.00371 | 0.33419 | ≥10.000 |
| 41 | tert-butyl 4-[4-[6-[2-cyano-3-[[(3R)-3-fluoropyrrolidin-1-yl]sulfonylamino]anilino]-4-oxo-quinazolin-3-yl]butanoylamino]piperidine-1-carboxylate | 0.00929 | 0.00619 | 1.50969 | ≥10.000 |
| 42 | tert-butyl 4-[6-[2-cyano-3-[[cyclopropyl(methyl)sulfamoyl]amino]anilino]-4-oxo-quinazolin-3-yl]butanoate | 0.20278 | 0.07920 | 0.16219 | 6.20176 |
| 43 | tert-butyl N-[3-[6-[2-cyano-3-[[(3R)-3-fluoropyrrolidin-1-yl]sulfonylamino]anilino]-4-oxo-quinazolin-3-yl]propyl]carbamate | 0.00718 | 0.00447 | 0.07459 | 5.60934 |
| 44 | (3R)-N-[2-cyano-3-[[4-oxo-3-(3-phenylpropyl)quinazolin-6-yl]amino]phenyl]-3-fluoro-pyrrolidine-1-sulfonamide | 0.02563 | 0.01510 | 0.01820 | 2.06703 |
| 45 | tert-butyl N-[2-[4-[6-[2-cyano-3-[[(3R)-3-fluoropyrrolidin-1-yl]sulfonylamino]anilino]-4-oxo-quinazolin-3-yl]butanoylamino]ethyl]-N-methyl-carbamate | 0.00834 | 0.00341 | 0.81443 | ≥10.000 |
| 46 | tert-butyl 4-[2-[6-[2-cyano-3-(pyrrolidin-1-ylsulfonylamino)anilino]-4-oxo-quinazolin-3-yl]ethyl]piperidine-1-carboxylate | 0.07347 | 0.02118 | 0.02060 | 2.53754 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

We claim:

1. A compound of formula (I)

(I)

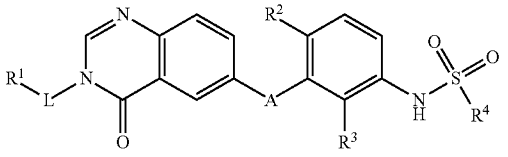

wherein

A is —O— or —NH—;

L is $-(CH_2)n-$, with n=1, 2, 3 or 4;

$R^1$ is alkoxycarbonyl, alkoxycarbonylheterocycloalkyl, alkoxycarbonylamino, phenyl, alkoxycarbonyl(alkylamino), alkylcarbonyl(alkylamino), alkoxycarbonyl (alkylamino)alkylphenyl, alkoxyalkylaminocarbonyl, alkylcarbonylheterocycloalkyl, alkoxycarbonylaminoalkoxyalkoxy, phenylalkoxy, aminoalkoxyalkoxy, hydroxycarbonyl, alkoxycarbonylheterocycloalkylcarbonyl, alkoxycarbonylheterocycloalkylaminocarbonyl or alkoxycarbonyl(alkylamino)alkylaminocarbonyl;

$R^2$ and $R^3$ are independently selected from the group consisting of hydrogen, fluorine and cyano;

$R^4$ is dialkylamino, (cycloalkyl)(alkyl)amino, haloheterocycloalkyl, heterocycloalkyl, cycloalkyl or alkyl;

or a pharmaceutically acceptable salt thereof.

2. The compound of claim 1, wherein $R^1$ is alkoxycarbonyl, alkoxycarbonylpiperidinyl, alkoxycarbonylpiperazinyl, alkoxycarbonylamino, alkoxycarbonyl(alkylamino), alkylcarbonyl(alkylamino), alkoxycarbonyl(alkylamino)alkylphenyl, alkoxyalkylaminocarbonyl, alkylcarbonylpiperidinyl, alkoxycarbonylaminoalkoxyalkoxy, phenylalkoxy, aminoalkoxyalkoxy, hydroxycarbonyl, alkoxycarbonylpiperidinylaminocarbonyl, alkoxycarbonylpiperazinylcarbonyl, or alkoxycarbonyl(alkylamino)alkylaminocarbonyl.

3. The compound of claim 1, wherein $R^1$ is alkoxycarbonylheterocycloalkyl, alkoxycarbonylamino, alkoxycarbonyl (alkylamino), alkylcarbonyl(alkylamino), alkoxycarbonylaminoalkoxyalkoxy, alkoxycarbonylheterocycloalkylcarbonyl, alkoxycarbonylheterocycloalkylaminocarbonyl or alkoxycarbonyl(alkylamino)alkylaminocarbonyl.

4. The compound of claim 1, wherein $R^1$ is tert-butyloxycarbonyl, tert-butyloxycarbonylpiperidinyl, tert-butyloxycarbonylpiperidinyl, tert-butyloxycarbonylpiperazinyl, tert-butyloxycarbonylamino, tert-butyloxycarbonyl(methylamino), methylcarbonyl(methylamino), tert-butyloxycarbonyl(methylamino)methylphenyl, methoxyethylaminocarbonyl, methylcarbonylpiperidinyl, tert-butyloxycarbonylaminoethoxyethoxy, phenylmethyloxy, aminoethoxyethoxy, hydroxycarbonyl, tert-butyloxycarbonylpiperazinylcarbonyl, tert-butyloxycarbonylpiperidinylaminocarbonyl or tert-butyloxycarbonyl(methylamino)ethylaminocarbonyl.

5. The compound of claim 1, wherein $R^1$ is tert-butyloxycarbonylpiperazinyl, tert-butyloxycarbonylamino, tert-butyloxycarbonyl(methylamino), methylcarbonyl(methylamino), tert-butyloxycarbonylaminoethoxyethoxy, tert-butyloxycarbonylpiperazinylcarbonyl, tert-butyloxycarbonylpiperidinylaminocarbonyl or tert-butyloxycarbonyl(methylamino)ethylaminocarbonyl.

6. The compound of claim 1, wherein $R^2$ is hydrogen or fluorine, and wherein $R^3$ is cyano.

7. The compound of claim 1, wherein $R^4$ is dialkylamino, haloheterocycloalkyl, heterocycloalkyl or cycloalkyl.

8. The compound of claim 1, wherein $R^4$ is ethyl(methylamino), (cyclopropyl)(methyl)amino, fluoropyrrolidinyl, pyrrolidinyl, cyclobutyl, cyclopentyl, cyclohexyl, azetidinyl, butyl or piperidinyl.

9. The compound of claim 1, wherein $R^4$ is ethyl(methylamino), fluoropyrrolidinyl, pyrrolidinyl, azetidinyl or cyclopentyl.

10. The compound of claim 1, wherein A is —O—.

11. The compound of claim 1, wherein L is $—(CH_2)n-$, with n=1, 2 or 3.

12. The compound of claim 1, wherein the compound is selected from

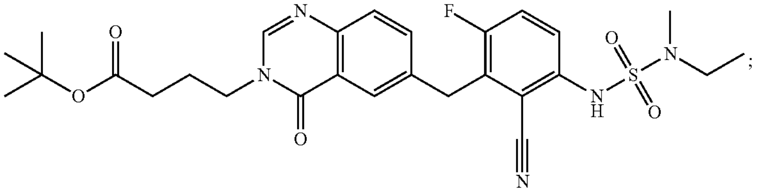
;

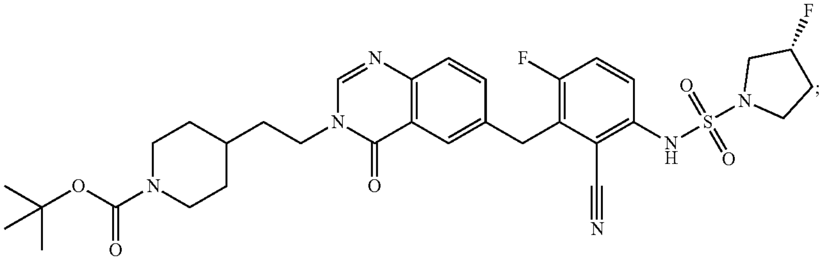
;

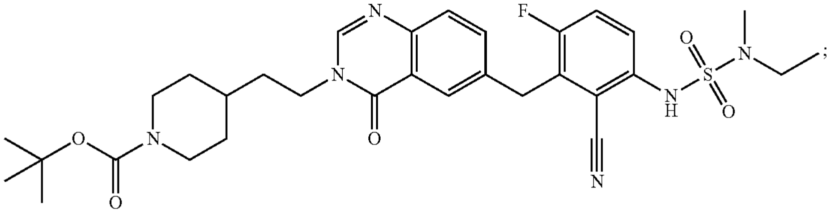
;

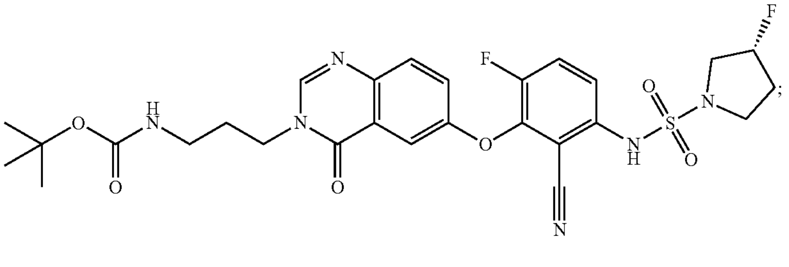
;

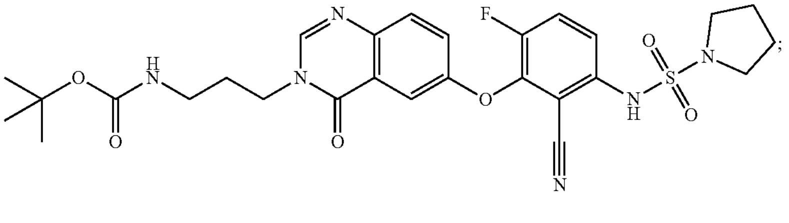
;

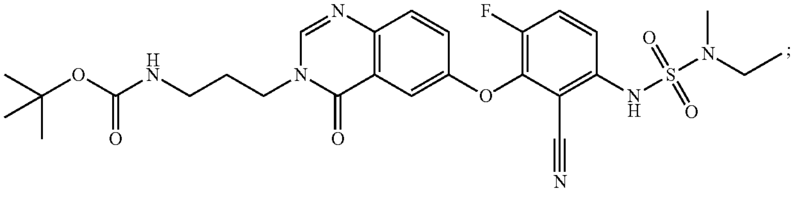
;

-continued
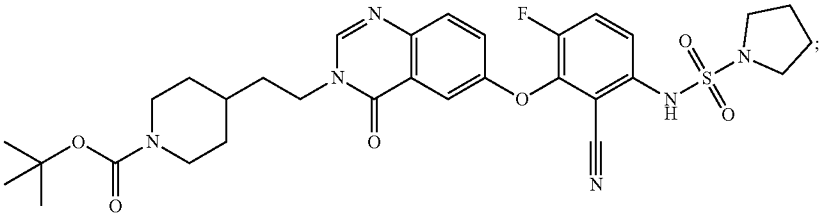
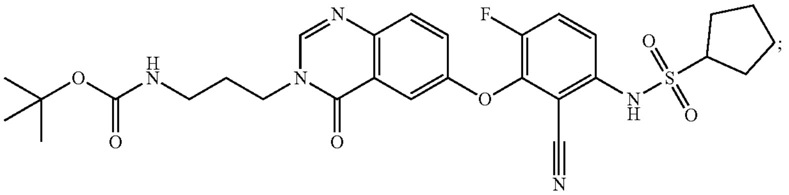
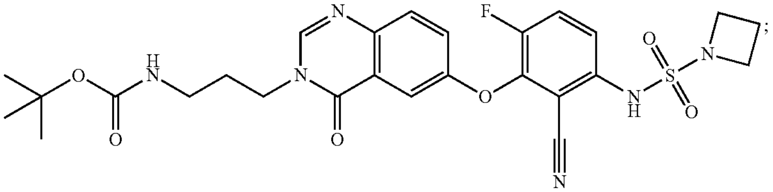
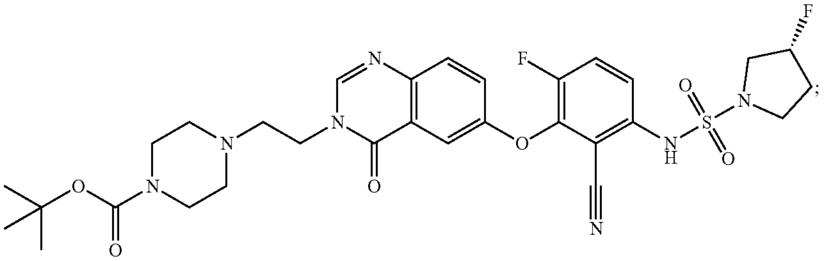
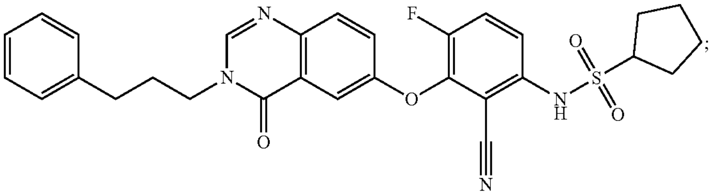
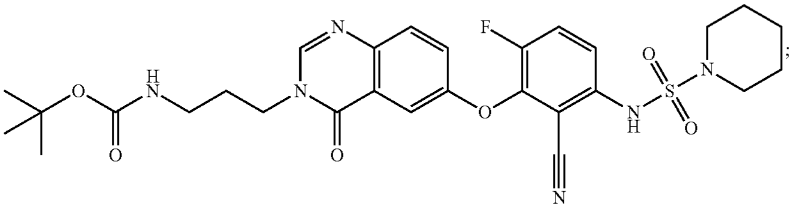
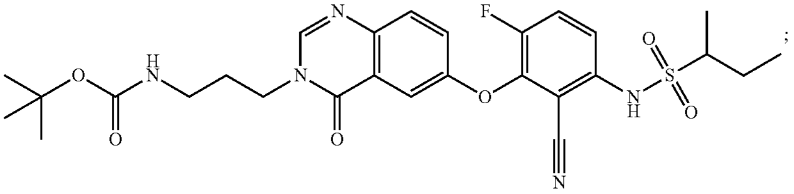
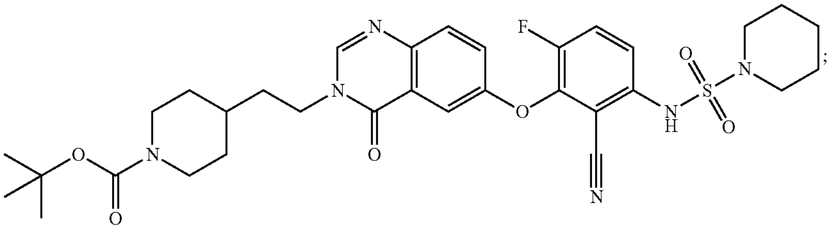

-continued
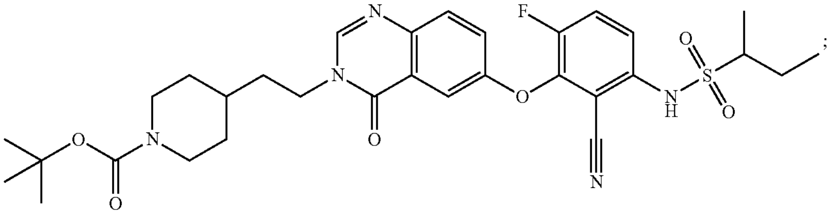
;
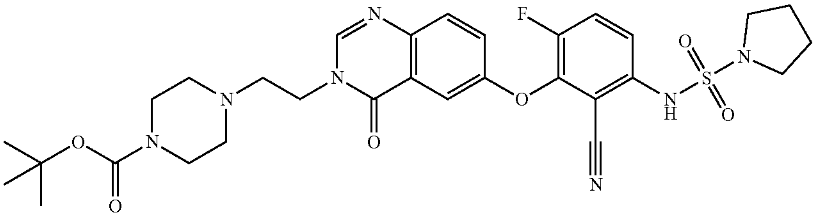
;
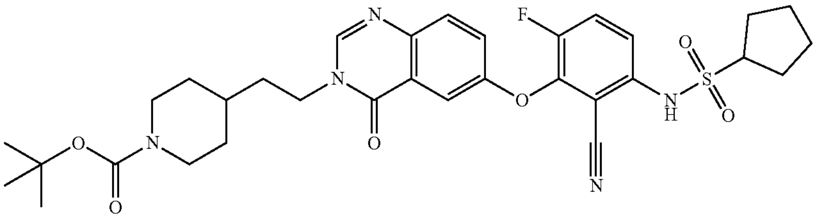
;
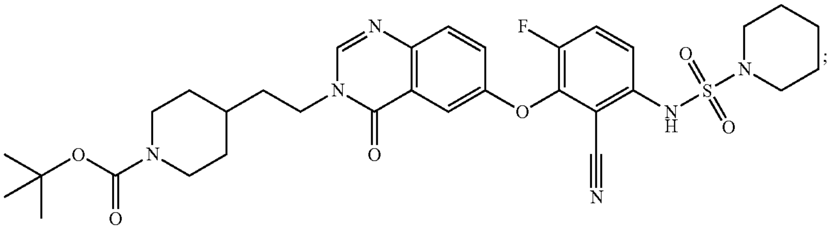
;
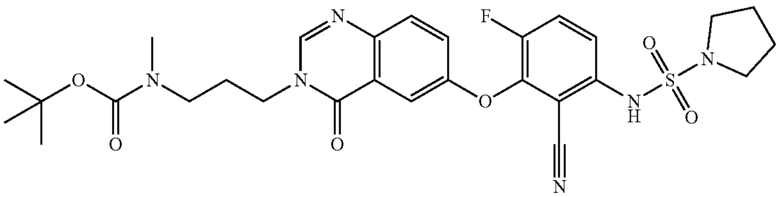
;
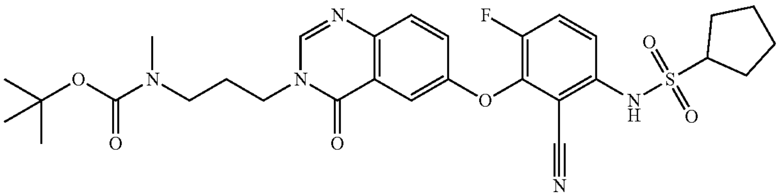
;
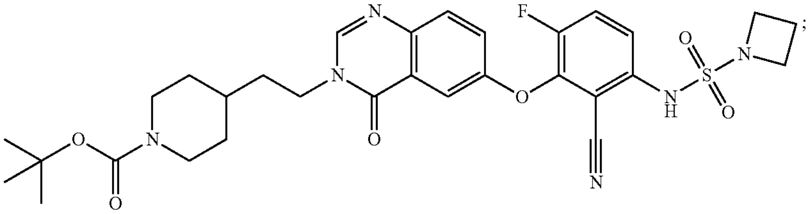
;

-continued
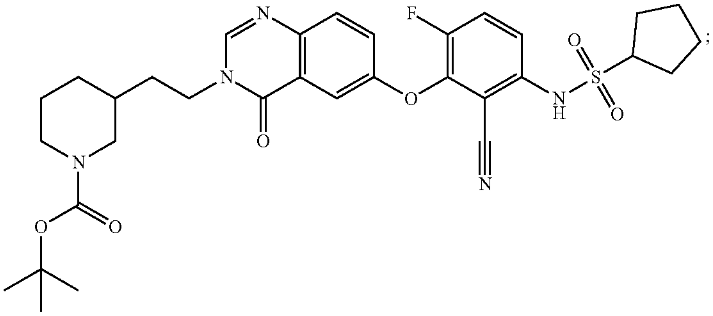
;
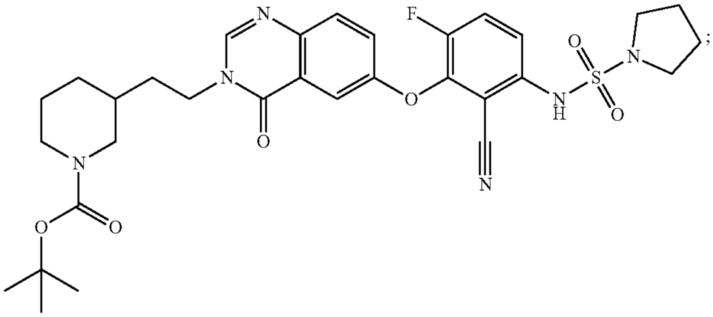
;
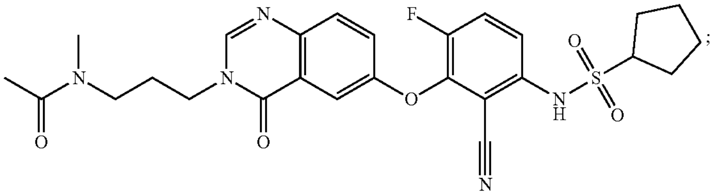
;
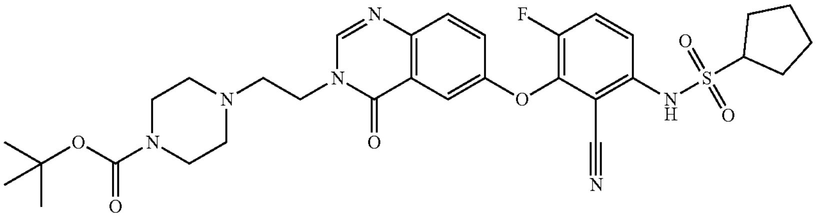
;
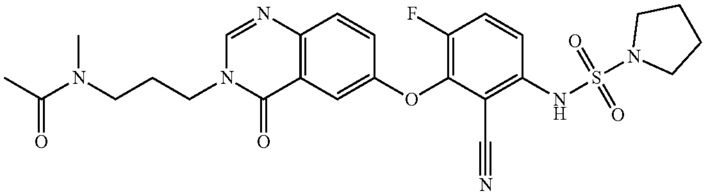
;
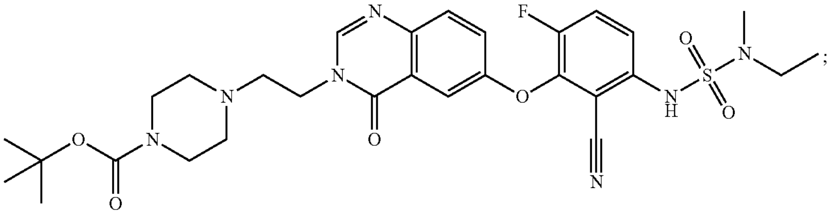
;
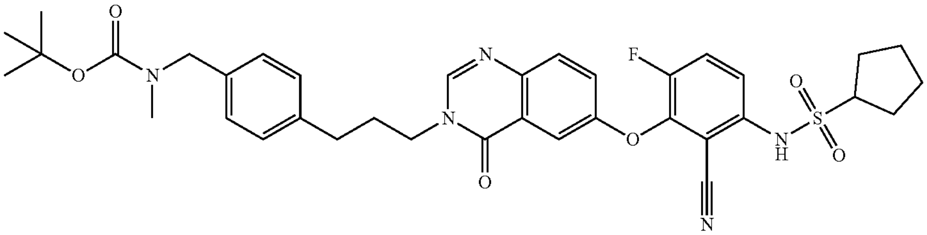
;

-continued
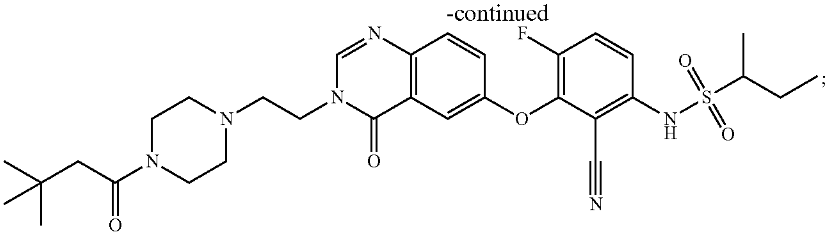
;
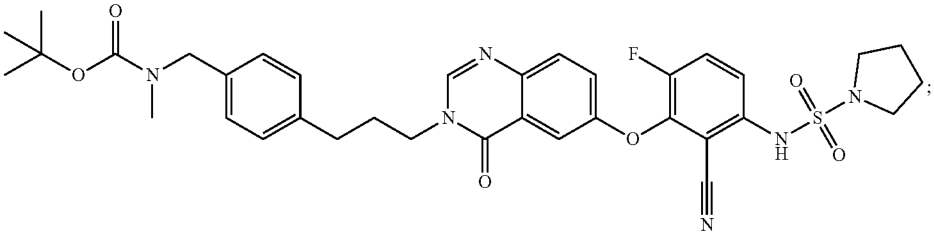
;
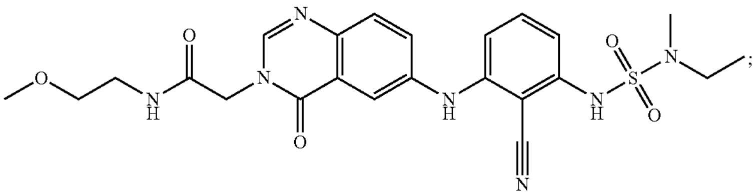
;
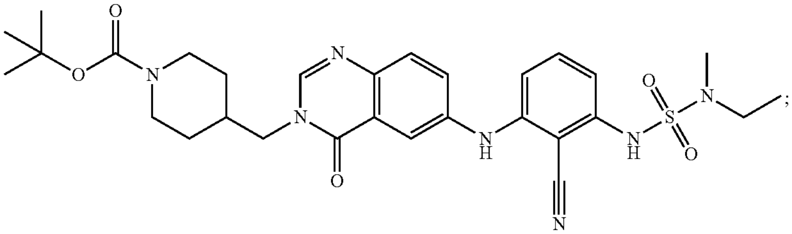
;
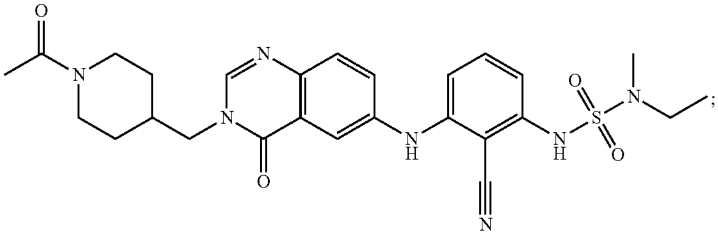
;
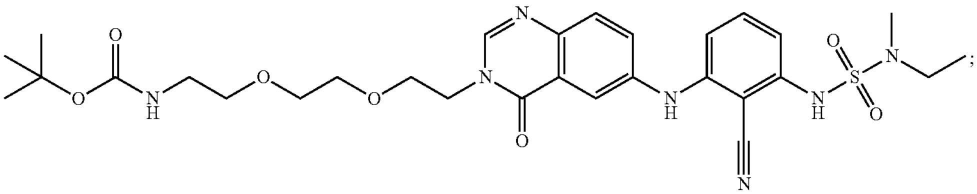
;
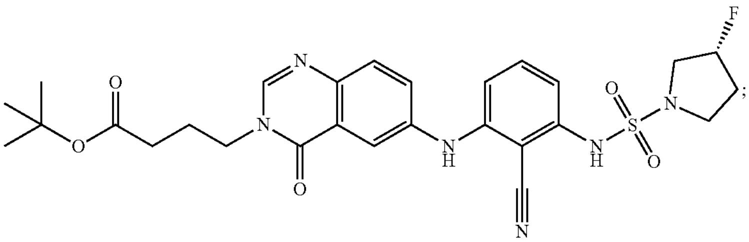
;

-continued
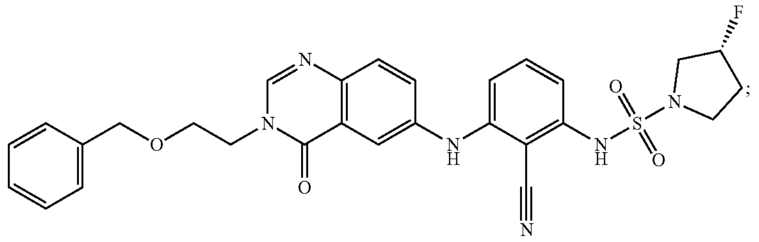
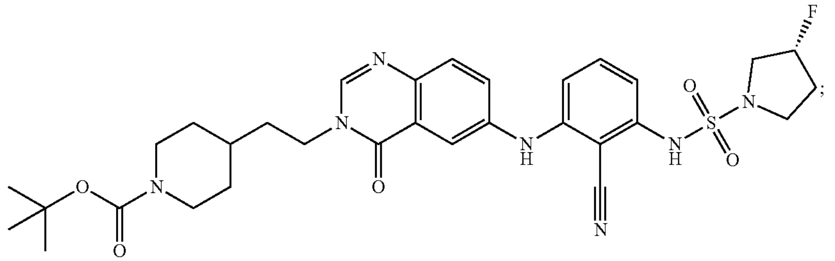
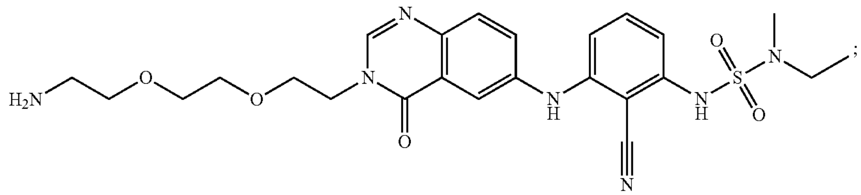
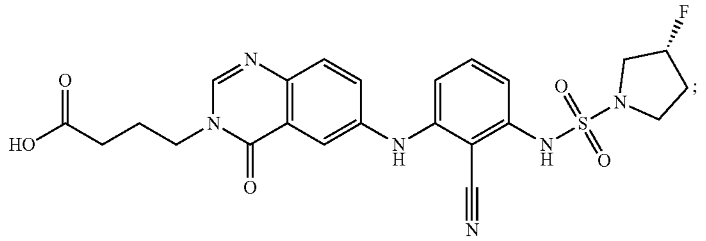
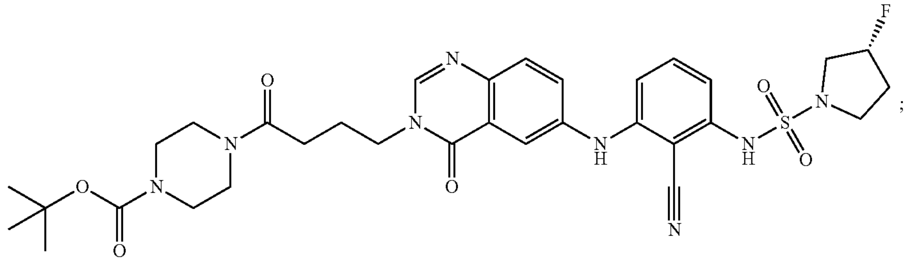
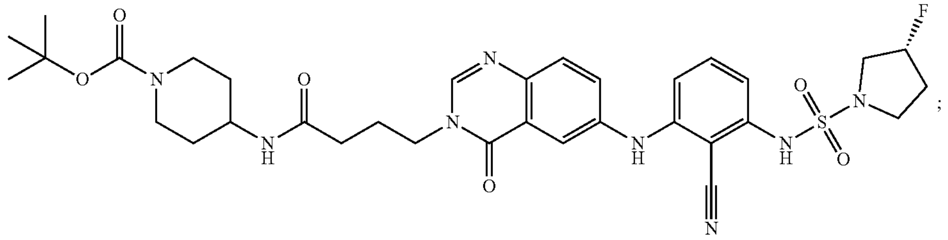
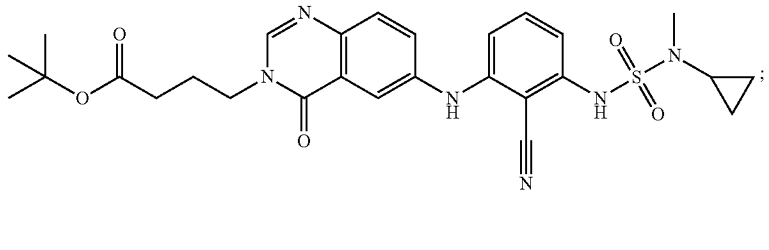

-continued
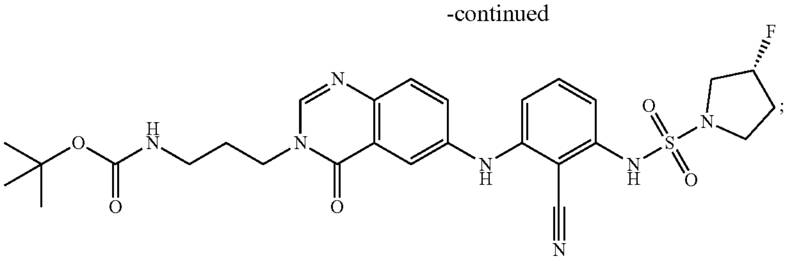
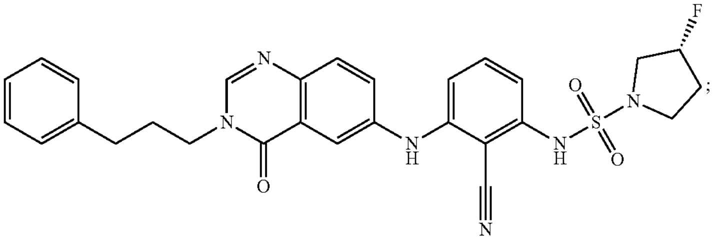
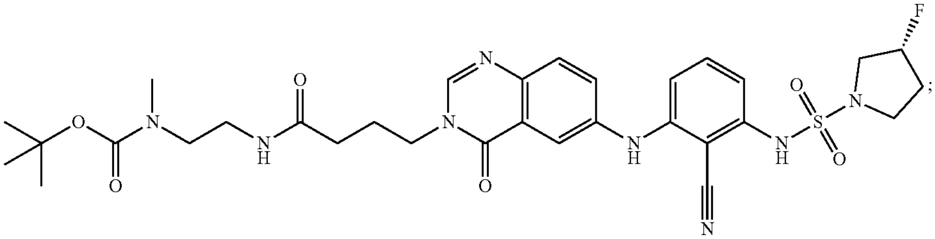
and
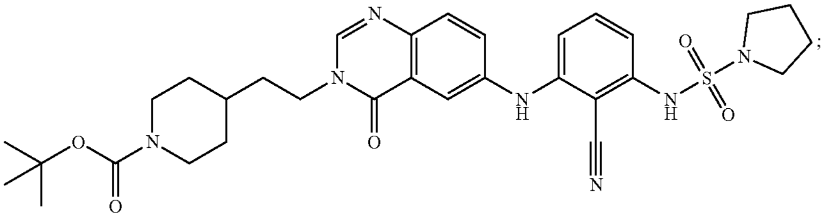
or a pharmaceutically acceptable salt thereof.
13. The compound of claim 1, wherein the compound is selected from
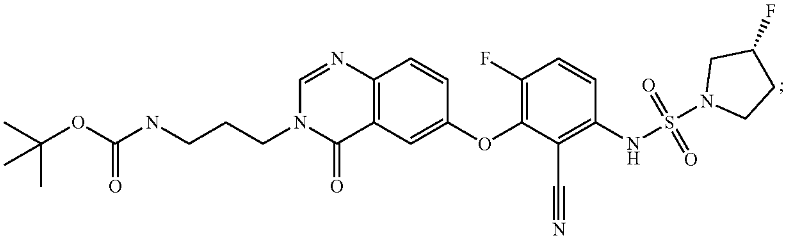
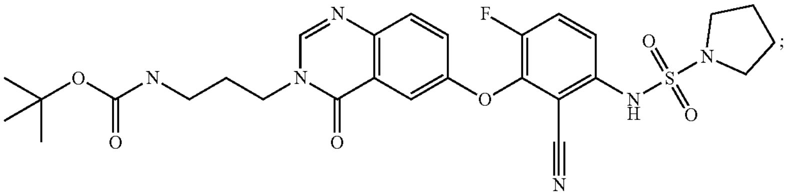

-continued
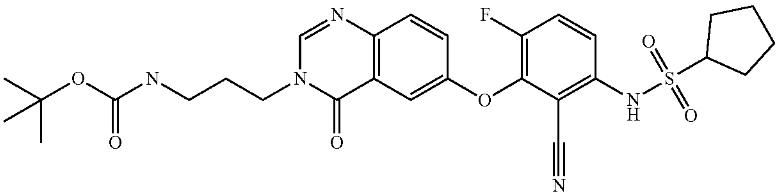
;
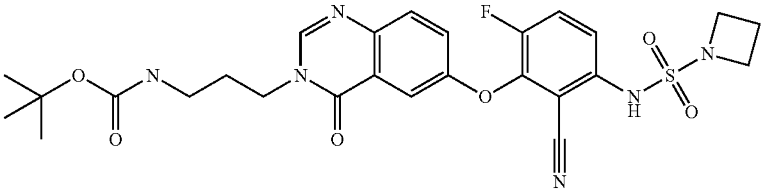
;
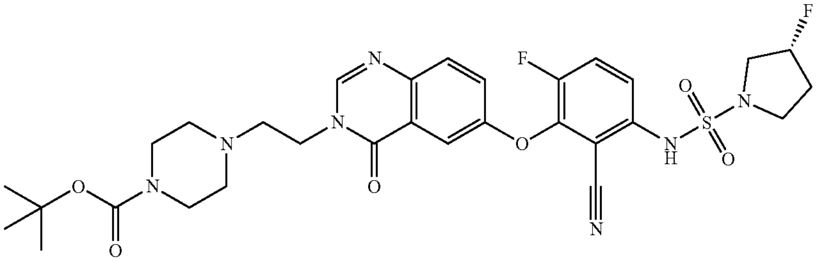
;
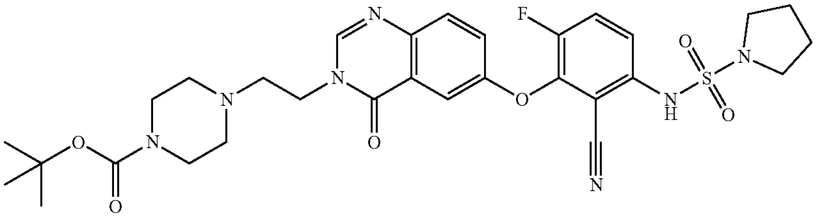
;
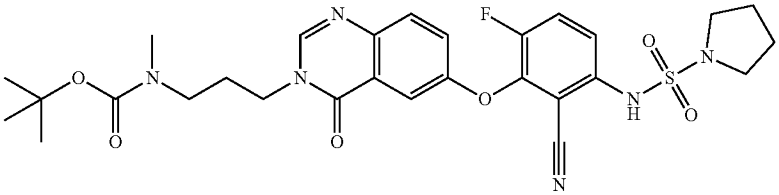
;
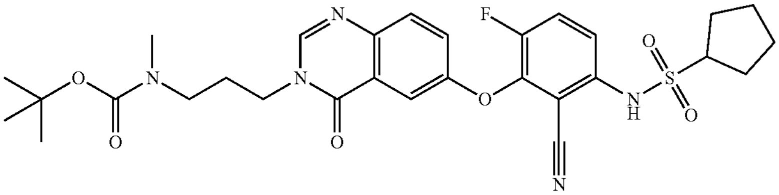
;
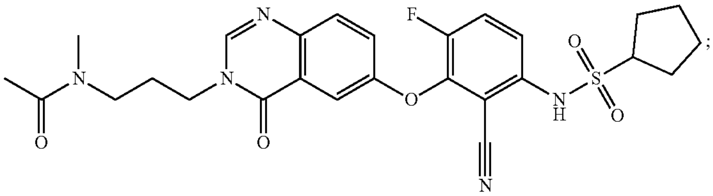
;
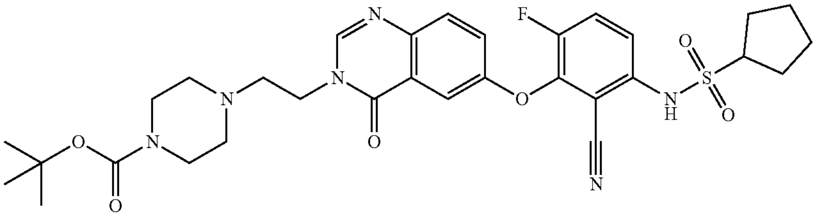
;

-continued
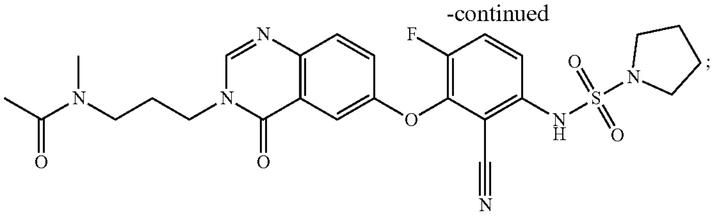;
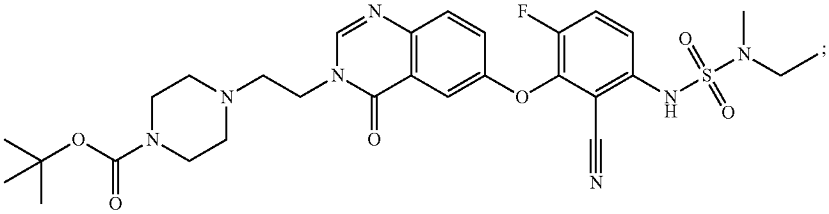;
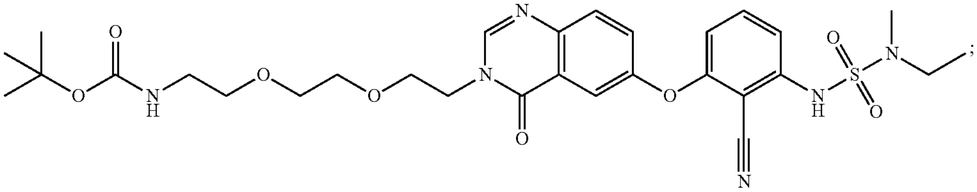;
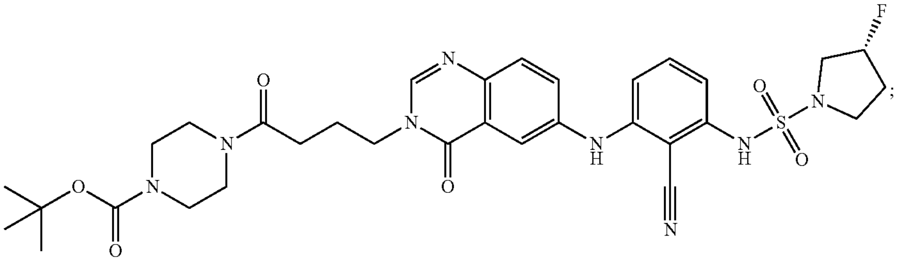;
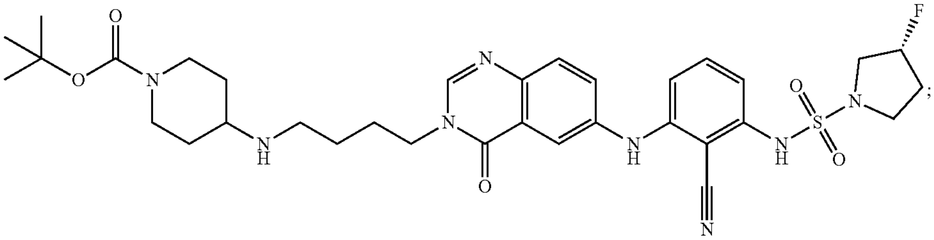;
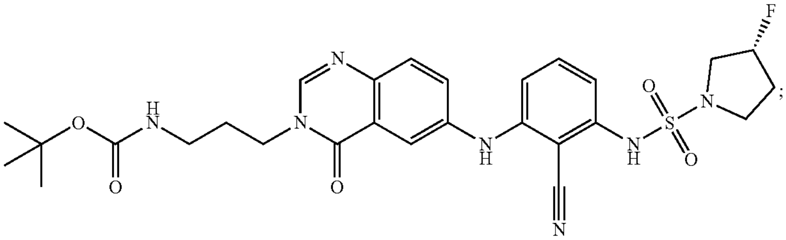; and
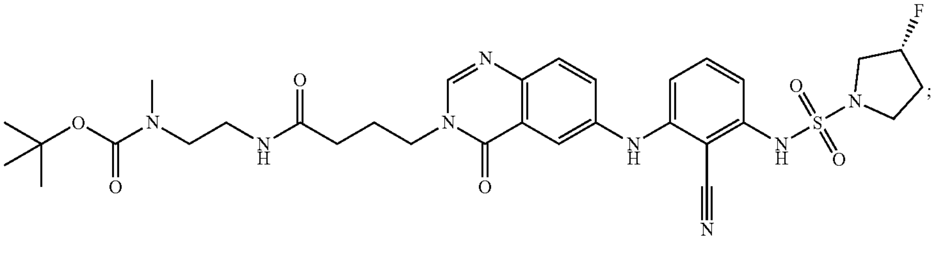;
or a pharmaceutically acceptable salt thereof.

14. A process for the preparation of a compound of formula (I) or a pharmaceutically acceptable salt thereof, comprising one of the following steps:

(a) the reaction of a compound of formula (A1)

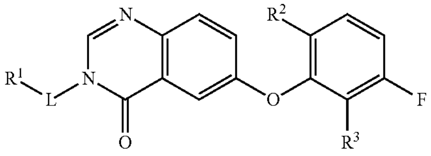

(A1)

with a compound of formula (A2)

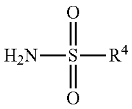

(A2)

in the presence of a base;

(b) the reaction of a compound of formula (B1)

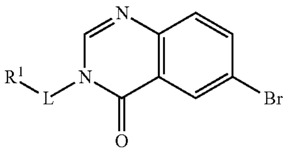

(B1)

with a compound of formula (B2)

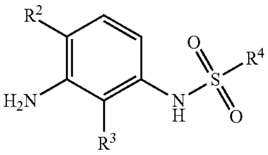

(B2)

in the presence of a base, a palladium catalyst and a suitable ligand; or (c) the reaction of a compound of formula (C1)

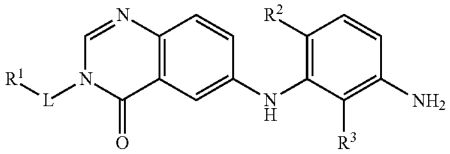

(C1)

with a compound of formula (C2)

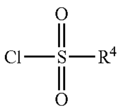

(C2)

in the presence of a base;

wherein

A is —O— or —NH—;

L is —$(CH_2)$n-, with n=1, 2, 3 or 4;

$R^1$ is alkoxycarbonyl, alkoxycarbonylheterocycloalkyl, alkoxycarbonylamino, phenyl, alkoxycarbonyl(alkylamino), alkylcarbonyl(alkylamino), alkoxycarbonyl (alkylamino)alkylphenyl, alkoxyalkylaminocarbonyl, alkylcarbonylheterocycloalkyl, alkoxycarbonylaminoalkoxyalkoxy, phenylalkoxy, aminoalkoxyalkoxy, hydroxycarbonyl, alkoxycarbonylheterocycloalkylcarbonyl, alkoxycarbonylheterocycloalkylaminocarbonyl or alkoxycarbonyl(alkylamino)alkylaminocarbonyl;

$R^2$ and $R^3$ are independently selected from the group consisting of hydrogen, fluorine and cyano; and $R^4$ is dialkylamino, (cycloalkyl)(alkyl)amino, haloheterocycloalkyl, heterocycloalkyl, cycloalkyl or alkyl.

15. A pharmaceutical composition comprising a compound of claim 1 or a pharmaceutically acceptable salt thereof and a therapeutically inert carrier.

16. A method for the treatment of cancer comprising administering an effective amount of a compound of claim 1 or a pharmaceutically acceptable salt thereof to a patient in need thereof.

17. The method of claim 16, wherein the cancer is melanoma.

18. The method of claim 16, wherein the cancer is non-small cell lung cancer.

* * * * *